(12) United States Patent
Otwinowski et al.

(10) Patent No.: US 10,870,882 B2
(45) Date of Patent: *Dec. 22, 2020

(54) METHOD FOR ACCURATE SEQUENCING OF DNA

(71) Applicant: Board of Regents, The University of Texas System, Dallas, TX (US)

(72) Inventors: Zbyszek Otwinowski, Dallas, TX (US); Dominika Borek, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 76 days.

This patent is subject to a terminal disclaimer.

(21) Appl. No.: 15/978,208

(22) Filed: May 14, 2018

(65) Prior Publication Data

US 2018/0282802 A1    Oct. 4, 2018

Related U.S. Application Data

(63) Continuation of application No. 14/550,517, filed on Nov. 21, 2014, now Pat. No. 9,970,054, which is a continuation of application No. PCT/US2013/042949, filed on May 28, 2013.

(60) Provisional application No. 61/654,069, filed on May 31, 2012.

(51) Int. Cl.
*C12Q 1/6869* (2018.01)
*C12Q 1/6844* (2018.01)

(52) U.S. Cl.
CPC ......... *C12Q 1/6869* (2013.01); *C12Q 1/6844* (2013.01)

(58) Field of Classification Search
CPC ............................ C12Q 1/6869; C12Q 1/6844
See application file for complete search history.

(56) References Cited

U.S. PATENT DOCUMENTS

| | | | |
|---|---|---|---|
| 5,747,298 A | 5/1998 | Hong | |
| 6,087,099 A | 7/2000 | Gupte | |
| 9,970,054 B2 | 5/2018 | Otwinoski | |
| 2003/0199007 A1 | 10/2003 | Pestka | |
| 2007/0172839 A1 | 7/2007 | Smith | |
| 2009/0298075 A1* | 12/2009 | Travers | C12Q 1/6869 435/6.12 |
| 2012/0046177 A1* | 2/2012 | Huang | C12Q 1/6869 506/2 |
| 2012/0115736 A1 | 5/2012 | Bjornson | |

FOREIGN PATENT DOCUMENTS

| | | | |
|---|---|---|---|
| WO | 2009120372 | 10/2009 | |
| WO | 2010064040 | 6/2010 | |
| WO | 2011037990 | 3/2011 | |
| WO | WO-2011037990 A1 * | 3/2011 | ........... C12Q 1/6874 |
| WO | WO-2013123442 A1 * | 8/2013 | ........... C12Q 1/6869 |
| WO | 2013181170 | 12/2013 | |

OTHER PUBLICATIONS

Aird, D.et al., Analyzing and minimizing PCR amplification bias in Illumina sequencing libraries, Genome Biol, 12:R18(2011).
Alon, S. et al., Barcoding bias in high-throughput multiplex sequencing of miRNA, Genome Research, 21 (9)1506-1511 (2011).
Bentley, D. et al., Accurate whole human genome sequencing using reversible terminator chemistry, Nature, 456 (7218):53-59 (2008).
Bordoni, R. et al., Evaluation of human gene variant detection in amplicon pools by the GS-FLX parallel Pyrosequencer, BMC Genomics, 9(1):464 (2008).
Bravo, H.C. and Irizarry, R.A., Model-based quality assessment and base- calling for second-generation sequencing data, Biometrics, 66:665-674 (2010).
Harris, TD. et al. Single-molecule DNA sequencing of a viral genome. Science, vol. 320, p. 106-109, 2008.
Hoeijmakers, W.A.M. et al., Linear amplification for deep sequencing, Nature Protocols, 6(7):1026-1036 (2011).
International Search Report for PCT/US13/42949 (Method for Accurate Sequencing of DNA, filed May 28, 2013) issued by ISA/KR, 4 pages (Aug. 21, 2018).
Kinde, I. et al., Detection and quantification of rare mutations with massively parallel sequencing, Proc Natl Acad Sci U S A, 108(23):9530-9535 (2011).
Kircher, M. et al., Double indexing overcomes inaccuracies in multiplex sequencing on the Illumina platform, Nucleic Acids Research, 40(1):e3 (2012).
Kozarewa, I. et al., Amplification-free Illumina sequencing-library preparation facilitates improved mapping and assembly of (G+C)-biased genomes, Nat Methods, 6:291-295 (2009).
McKenna, A. et al., The Genome Analysis Toolkit: a MapReduce frameworkor analyzing next-generation DNA sequencing data, Genome Res, 20:1297-303 (2010).
Menges, F. et al., TotalReCaller: improved accuracy and performance via integrated alignment and base-calling, Bioinformatics, 27:2330-2337 (2011).

(Continued)

*Primary Examiner* — Young J Kim
(74) *Attorney, Agent, or Firm* — Richard Aron Osman

(57) ABSTRACT

DNA is sequenced by (a) independently sequencing first and second strands of a dsDNA to obtain corresponding first and second sequences; and (b) combining the first and second sequences to generate a consensus sequence of the dsDNA. By independently sequencing first and second strands the error probability of the consensus sequence approximates a multiplication of those of the first and second sequences.

19 Claims, 9 Drawing Sheets

Specification includes a Sequence Listing.

(56) References Cited

OTHER PUBLICATIONS

Meyer, M. and Kircher, M., Illumina sequencing library preparation for highly multiplexed target capture and sequencing, Cold Spring Harbor Protocols, 2010(6):1-10 (2010).
Pugachev, K.V. et al., Heterogeneous nature of the genome of the ARILVAX yellow fever 17D vaccine revealed by consensus sequencing, Vaccine, 29(7-8):996-999 (2002).
Schmitt, M.W. et al., Detection of ultra-rare mutations by next-generation sequencing, PNAS, 109(36)14508-14513 (2012).
Stamoulis, C. and Betensky, R.A., A novel signal processing approach for the detection of copy number variations in the human genome, Bioinformatics, 27:2338-2345 (2011).
The 1000 Genomes Project Consortium, A map of human genome variation from population-scale sequencing, Nature 467(7319):1061-1073 (2010).
Voss, H. et al., Efficient low redundancy large-scale DNA sequencing at EMBL, Journal of Biotechnology, 41 (2):121-129 (1995).
Written Opinion for PCT/US13/42949 (Method for Accurate Sequencing of DNA, filed May 28, 2013) issued by ISA/KR, 3 pages (dated Aug. 21, 2018).
Yao, E. et al., A general method for nested RT-PCR amplification and sequencing the complete HCV genetype 1 open reading frame, Virology Journal, 2(1):88 (2005).

* cited by examiner

SEQUENCE LISTING

```
<160> NUMBER OF SEQ ID NOS: 4

<210> SEQ ID NO 1
<211> LENGTH: 98
<212> TYPE: DNA
<213> ORGANISM: Artificial Sequence
<220> FEATURE:
<223> OTHER INFORMATION: Synthetic; Sequencing Adapter

<400> SEQUENCE: 1
atttgctctc tcggcgttaa aagtggcggg tgcgctggtg ctggtggtat tgctggggcg      60
ctatgtcacg cgtccggcgc tgcgttttgt agcccgct                             98

<210> SEQ ID NO 2
<211> LENGTH: 34
<212> TYPE: DNA
<213> ORGANISM: Artificial Sequence
<220> FEATURE:
<223> OTHER INFORMATION: Synthetic; Sequencing Adapter

<400> SEQUENCE: 2
agatcggaag agcacacgtc tgaactccag tcac                                 34

<210> SEQ ID NO 3
<211> LENGTH: 58
<212> TYPE: DNA
<213> ORGANISM: Artificial Sequence
<220> FEATURE:
<223> OTHER INFORMATION: Synthetic; Sequencing Adapter

<400> SEQUENCE: 3
aatgatacgg cgaccaccga gatctacact ctttccctac acgacgctct tccgatct       58

<210> SEQ ID NO 4
<211> LENGTH: 45
<212> TYPE: DNA
<213> ORGANISM: Artificial Sequence
<220> FEATURE:
<223> OTHER INFORMATION: Synthetic; Sequencing Adapter
<220> FEATURE:
<221> NAME/KEY: VARIANT
<222> LOCATION: (42)
<223> OTHER INFORMATION: Synthetic; n is a, c, t or g.
<220> FEATURE:
<221> NAME/KEY: VARIANT
<222> LOCATION: (43)
<223> OTHER INFORMATION: Synthetic; n is a, c, t or g.
<220> FEATURE:
<221> NAME/KEY: VARIANT
<222> LOCATION: (44)
<223> OTHER INFORMATION: Synthetic; n is a, c, t or g.
<220> FEATURE:
<221> NAME/KEY: VARIANT
<222> LOCATION: (45)
<223> OTHER INFORMATION: Synthetic; n is a, c, t or g.

<400> SEQUENCE: 4
cactgacctc aagtctgcac acgagaaggc tagayyyrrr rnnnn                     45
```

METHOD FOR ACCURATE SEQUENCING OF DNA

This application is a continuation of Ser. No. 14/550,517, filed Nov. 21, 2014, which is a continuation of PCT/US13/042949; which claims priority to 61/654,069, filed May 31, 2012.

INTRODUCTION

Uncorrected lesions in DNA lead to somatic mutations, which accumulate over the life of organism. The accumulation of somatic mutations contributes to dispersive cellular processes such as aging and the onset, development, and evolution of malignancies. The understanding of the exact nature of this contribution requires precise quantification of the levels of somatic mutations and the rates of accumulation, together with precise mapping of the mutational spectra. However, the pattern of somatic mutations is different in each cell, and the high fidelity of DNA replication and repair results in a very low number of somatic mutations per single cell. For humans, the number of somatic mutations accumulated across the life span of the particular cell is in the range of 100-10,000, depending on the number of cell divisions, the metabolic load and environmental insults. This makes the quantification of somatic mutations across a cellular population a very challenging task, which until now has either relied on phenotypic selection of mutations or was limited to special types of mutations; in microsatellites, at the restriction sites or those amplified in clonal populations. It is not clear how those indirect or fragmentary measurements affected the conclusions. The lack of well-defined baselines for somatic mutation levels due to those difficulties, and discrepancies between results, has led to standing controversies and problems with interpretations of the mechanisms involved in aging and cancer.

We disclose a genome-wide, unbiased method to precisely determine the level of somatic mutations by direct sequencing. We apply a novel experimental design that provides built-in validation, and combine it with statistical analysis that efficiently identifies rare events such as somatic mutations in the background created by the combination of: single nucleotide polymorphisms, sequence changes introduced during DNA sample processing, pre-mutation changes in DNA bases that would otherwise be corrected by the DNA repair machinery, and sequencing errors. We achieve less than 1 error per 1,000,000,000 (billion) sequenced base pairs. We use this approach to determine the patterns of somatic mutations in several types of human tissue obtained from human organs with different age. This invention enables the establishment of baselines of somatic mutations for humans and also determine the tissue-specific spectra of somatic mutations and the rates of mutation accumulation associated with them, such as mutation patterns associated with frequent cellular replications, with metabolic load, and with interactions with environment.

Relevant Literature: Kircher et al., 2011, Nucleic Acids Res. Advance Access, 1-18; US 2007/0172839; Schmitt, Sep. 4, 2012, PNAS (USA) 109 (36)14508-14513, published before pint, Aug. 1, 2012, doi: 10.1073/pnas.1208715109, Detection of ultra-rare mutations by next-generation sequencing.

SUMMARY OF THE INVENTION

The invention provides materials and methods for sequencing DNA. We colloquially refer to some embodiments of subject methods as "Twin-Seq".

In one aspect the invention is a method for sequencing DNA comprising steps: (a) independently sequencing first and second strands of a dsDNA to obtain corresponding first and second sequences; and (b) combining the first and second sequences to generate a consensus sequence of the dsDNA. By independently sequencing first and second strands the error probability of the consensus sequence approximates a multiplication of those of the first and second sequences.

The first and second sequences may derive from single molecule reads or composite reads of clonal amplification products of the first and second strands.

In a particular embodiment the sequencing step (a) comprises: (i) amplifying the dsDNA to obtain multiple copies of the first and second strands; (ii) sequencing the copies to obtain copy sequences, wherein each of the copy sequences is optionally a composite sequences generated from multiple reads of each copy; and (ii) combining the copy sequences to obtain first and second strand consensus sequences that are the first and second sequences.

Generally, uses sequencing reads long enough to cover the whole length of dsDNA insert and/or sequencing reads that have the same quality information about both ends of the insert (paired-end sequencing). In the case of paired-end sequencing the same quality means the quality of readout and the length of both reads. Therefore, Illumina sequencing is well-adapted to Twin-seq, and SOLID less so, unless the second read in paired-end sequencing is improved.

Suitable sequencing methodologies generally comprise: library preparation, sequencing process, and type of readout (detection). Twin-seq accommodates a wide variety of readout types (e.g. electronic or fluorescent), and protocols (e.g. single-molecule or polonies, specific chemistry during amplification); however, the length of the sequencing reads and ability to do paired-end sequencing if length is limited is important.

Accordingly, the sequencing of the subject methods may be performed by any compatible methodology, including: a. massively parallel signature sequencing (Lynx MPSS; b. polony sequencing; c. parallelized pyrosequencing (454 Life Sciences); d. reversible dye terminator-based sequencing (Solexa); e. ligation-based sequencing (SOLiD, ABI); f. ion-semiconductor sequencing; g. DNA nanoball sequencing; h. extension-based single molecule sequencing (Helicose); i. single molecule real time sequencing (RNAP); j. nanopore sequencing; k. FRET-donor-polymerase-based sequencing (VisiGen Biotechnologies); and l. hybridization sequencing.

In a more particular embodiment, the subject methods further comprise the steps of: (i) PCR amplifying a dsDNA fragment having a sequence flanked by Y-adapters to produce asymmetrical, amplified dsDNA; (ii) denaturing the amplified dsDNA and attaching and then bridge amplifying resultant amplified ssDNA at discrete locations of a flow cell to produce polonies; (iii) reading the sequences of the polonies; and (iv) identifying same-sized complementary sequences, which provide the first and second sequences corresponding to the first and second strands of the dsDNA.

Asymmetry is provided by Y-adapters, however we can also add barcodes and/or randomization to increase analysis confidence that two different reads obtained from sequencing were part of the same dsDNA fragment/insert before PCR, and not two different fragments. Additionally or alternatively we can also employ different adapters produced with two consecutive ligations, which ligations could be separated by fragmentation and amplification steps. In a sample that has a low complexity, for example mitochondrial DNA or exome-selected DNA, several reads can have the same sequence and length. However, thanks to clonal amplification, if they are indeed originating from the same dsDNA fragment, they should have the same sequence of randomized barcode. This aspect differentiating coincidences from clonally amplified sequences is particularly important for validation.

In particular embodiments the subject methods further comprise the step of identifying one or more correspondences between the first and second sequences and a genomic DNA sequence, which may be effected by mapping the first and second sequences to a genomic DNA sequence; by metagenomic analysis; by relating one or more mutations of the genomic DNA sequence to the first and/or second sequence; etc.

The invention includes all combinations of recited particular embodiments as if each combination had been laboriously recited.

DETAILED DESCRIPTION OF PARTICULAR EMBODIMENTS

Figure 1A:
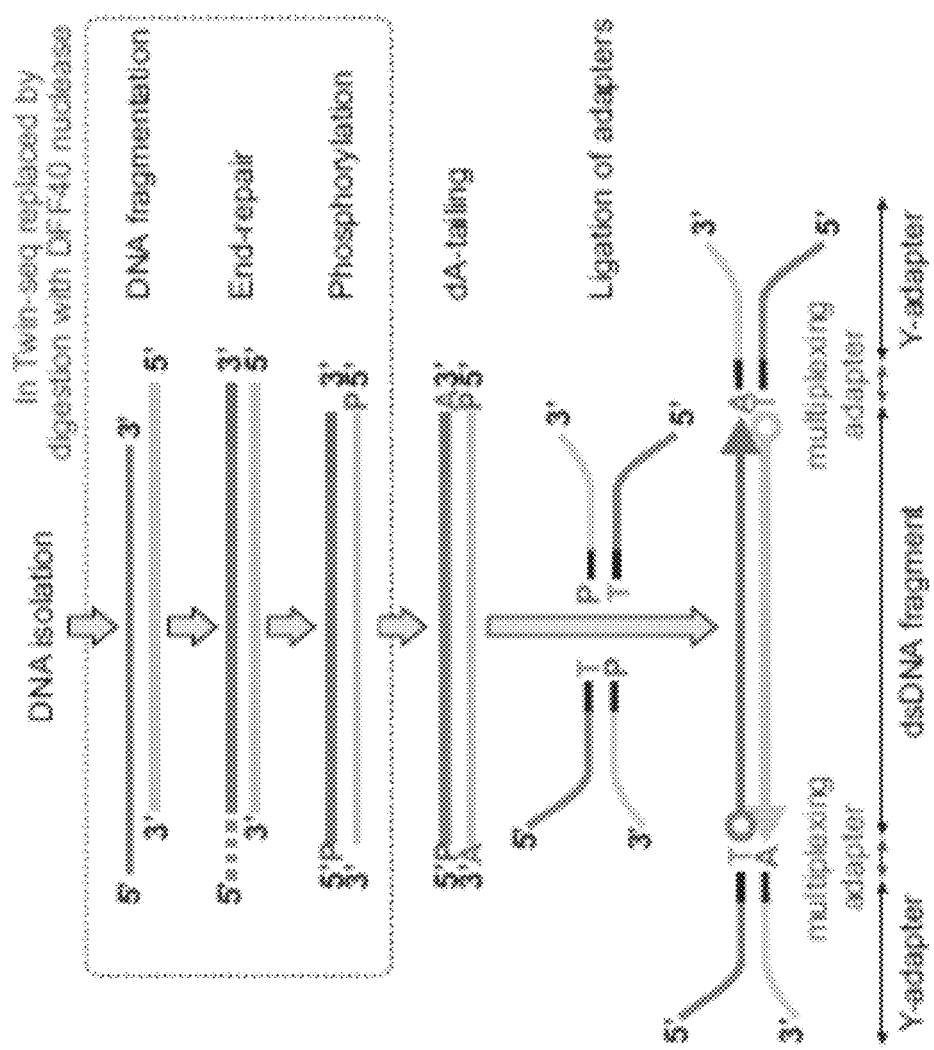
FIG. 1A. Preparation of the sequencing library in Twin-seq method in comparison to the standard Illumina library preparation.

One aspect of the invention employs a combination of methods to obtain highly accurate results of high-throughput sequencing utilizing clonally amplified templates (reviewed in, Metzker, M. L. (2010). "Sequencing technologies—the next generation." Nature Reviews Genetics 11(1): 31-46), such as that obtained with the Illumina platform (Bentley, D. R., S. Balasubramanian, et al. (2008) "Accurate whole human genome sequencing using reversible terminator chemistry." Nature 456(7218): 53-59.). The invention allows for differentiation, with very high certainty, between the correct DNA sequences, which have been present in the DNA in the cell, and the erroneous DNA sequences, which are generated when: (1) any of the steps in sequencing procedure introduces a change or a modification into the original DNA sequence, or (2) due to other instrumental or software issues. The error-generating events take place, among others, during experimental isolation of the DNA, during preparation of the isolated DNA for sequencing, and during the sequencing process itself. The sequencing technologies use a complex instrumentation and multi-step chemical processes, and every part of the sequencing technology may separately contribute to the accumulation of errors and damage in the DNA molecules.

Current methods of analyzing redundant, i.e. high coverage, sequencing data suffer from repetitive patterns of sequencing errors and lack of adequate validation to differentiate them from desired biological signal; those shortcomings are addressed by the Twin-seq approach. In respect of sequence certainty of a single DNA molecule, the Twin-seq method achieves the error level several orders of magnitude lower than other methods. In individual sequencing reads, the sequencing errors are very frequent and the difficulties with separating them from the true changes in DNA sequence, for instance DNA mutations or nucleotide polymorphisms, affect many fields in basic science, medicine, and industry. The Twin-seq design has a built-in validation that allows for a clear separation of real changes in DNA sequence from the DNA damage, sequencing errors and other effects that can result in changes mimicking a DNA sequence change at the source. The advantage of the Twin-seq method is that the validation is based on internal consistency of each experimental data set, so the reliability of sequencing data can be robustly ascertained, which is of particular significance when the quality of the result is subject to certification or regulation.

The very precise sequencing obtained with Twin-seq approach provide numerous applications:
  treatments personalized according to the individual genomic differences, either inherited or acquired (e.g., personalized medicine in any context)
  diagnostic tests for genetic disorders:
  finding mutations common to the whole organism, including prenatal tests,
  tests to quantify levels of mitochondrial heteroplasmy (e.g., prenatal diagnosis of mitochondrial and other disorders)
  diagnostic tests to estimate the progress of diseases characterized by genomic instabilities (e.g., a precise diagnosis of cancer development or the origin and progress of metastasis)
  development and validation of large-scale correlative analyses, which identify genomic variants associated with complex diseases (e.g., single nucleotide polymorphisms discovery and characterization)
  detection of patterns of somatic mutations correlated with complex diseases and aging
  precise testing and quantification of mutagenic potential of chemical substances and materials used in all kinds of industries (e.g., food, cosmetics, therapeutics, environmental)
  quantification of somatic mutations associated with particular exposures in the past, e.g. radioactivity, medical procedures and industrial exposures
  reliable and sensitive forensic tests for mitochondrial and genomic DNA The Twin-seq method can be used to replace the widely used Ames test and its derivatives, and due to its built-in internal validation may become the inherent part of:
  laboratory testing procedures performed on human-derived materials that are regulated by the Clinical Laboratory Improvement Amendments (CLIA) in the US and by similar regulations in other countries,
  laboratory testing procedures performed on: food, drugs, medical devices, vaccines, blood & biologics, animals, cosmetics, radiation-emitting products, tobacco products, regulated by the Food and Drug Administration (FDA) in US and similar agencies in other countries, laboratory testing procedures performed on substances and living organisms, and regulated by other federal agencies in the US, e.g. Environmental Protection Agency, and similar agencies in other countries, radiological exposure regulations.

The Twin-seq method utilizes the following unusual features, which decrease the error level and provide highly reliable information about the type and sources of sequencing errors:

a) Independence of the Strands of Duplex DNA with Respect to the Accumulation of Chemical Damage and Consequent Sequencing Errors The ligation of the so called Y sequencing adapters allows for the identification of the original strands in DNA sequencing; it is used in RNA sequencing, where it has no consequences for reliability analysis, since RNA has only one strand. It has not been noticed that, when sequencing double-stranded DNA, it is possible to achieve full independence of chemical errors from the two initial, complementary DNA strands. Either by fully sequencing the original DNA strands, or by paired-end sequencing of the same length from both ends of the sequenced fragments, data from both original strands can be combined for statistical analysis. By eliminating the DNA repair step, in Twin-seq procedure each strand of the duplex accumulates sequencing errors and chemical damage independently of its partner. Independence of errors for the two strands allows for multiplying probabilities of sequencing errors associated with each strand, and leads to error levels several orders of magnitude lower than achieved by other in vitro clonal amplification sequencing methods. The essential condition to apply this feature is preserving double-stranded character of the dsDNA fragments before ligation of the sequencing adapters.

b) Modification of Protocol for the Sequencing Library Preparation

The library preparation protocols contain multiple steps that may introduce damage to DNA template, such as depurination, deamidation, or oxidative damage to bases. These modifications may increase error levels in sequencing, and some of them may result in correlated patterns of errors that mimic mutational changes. In pilot experiments, we identified the main reasons of the problems: fragmentation of DNA at the beginning of library preparation and oxidative damage that is introduced at every step of the procedure. Therefore, in the Twin-seq procedure we prefer to use the following modifications:

DNA fragmentation by sonication is replaced by DNA digestion with dsDNA-specific nuclease, for instance: shrimp and DFF40 nucleases, which leave DNA ends blunt, so they do not need repairing or a fill-in step. This modification in the protocol removes the correlated changes in the complementary positions on both strands of the duplex. In standard protocol, DNA fragmentation by mechanical, enzymatic or other means creates single-stranded extensions that are subsequently blunted by the action of T4 polymerase and exonuclease. However, single-stranded extensions are more prone to the oxidative damage than dsDNA. The damage of a particular base in the single-stranded extension changes the template that T4 polymerase uses for generating double-stranded, blunt ends, which is the next step of the preparation of sequencing library. T4 polymerase encounters a damaged base in the template and introduces its partner—a complementary base. However, the damage may change the pattern of the preferred hydrogen bonds, which results in the stabilization of interactions with an incorrect nucleotide in the complementary position. After blunt-ending and ligation of Y-adapters, this error is further amplified in PCR, and may result in a false mutation call.

In each step of the process we add to chemicals or solutions used for standard library preparation one or two chemical compounds: sodium iodide and/or sodium nitrate. We add them in micromolar to milimolar concentration range, depending on the type and the state of a sample from which DNA is isolated. Previously, in unrelated, crystallographic studies, we identified these two chemicals as efficient scavengers of hydrated electrons and oxygen radicals. This reduces the oxidative damage to DNA, resulting in better control of the sequencing errors. Other scavenging substances can also be used for this purpose. Previously, this approach to reduce the oxidative damage in in vitro steps of library preparation has not been used in sequencing.

All DNA purification steps are performed in temperatures below 45° C. to prevent the denaturation of short, AT-rich, fragments. Denaturation of dsDNA fragments in a complex mixture results in ssDNA fragments that cannot anneal back with its complementary sequences. It decreases the efficiency of the procedure before ligation, because the ssDNA fragments cannot be ligated to double-stranded adaptors efficiently.

c) Ligating dsDNA Fragments to Barcoded, Randomized Y-Type Adapters

Ligation of dsDNA fragments (inserts) to the defined Y-type adapters is a part of the standard sequencing library preparation. The partially single-stranded nature of Y adapters, when ligated to the original, unamplified double-stranded DNA molecule, allows, after obtaining sequencing reads, for the identification of complementary strands originating from the same dsDNA fragment. Since this identification relies on similarities between short DNA sequences, there is a possibility of accidental sequence coincidences of different DNA fragments that happen to have very similar or identical sequences. In the case of identical sequences, the inability to identify their origin from the same or different fragment does not create much of an issue; however, a problem arises when very similar fragments from different DNA pieces appear in sequencing results. Such coincidences of fragments having the same length and sequence are much more likely, and so problematic, in the case of samples originating from small genomes, e.g. mitochondrial, or in samples enriched in specific sequences, e.g. exome sequences, or when sequencing repetitive regions. To distinguish such coincidences, the sequencing adapters are randomized in particular positions that are later read out during sequencing. Even for inserts with (almost) identical sequences, the differences in the randomized parts of the adapter can be used to distinguish the original DNA fragments. In terms of technology of sequencing, randomization uses an approach similar to barcoding that allows for distinguishing multiple sequencing experiments in a combined pool of DNA, an approach called multiplexing. Randomization and barcoding can be used together in adjacent positions of the adapter. There are two places in the adapter to introduce randomization and the barcode, and depending on the type of the experiment, they can be used at the same time. While randomization is not essential for some applications of the Twin-seq method, in all cases it provides a useful addition to the validation procedure.

Different type of barcoding was used to allow multiplexing of sequencing reaction, the digital counting or RNA copies, and randomized adapters were used to identify the molecules in complex mixtures. In our procedure, we introduce barcoded/randomized sequences in one-step ligation procedure, whereas in other approaches applying randomization for clonal validation purposes they were introduced by multi-step PCR that prevented discrimination of complementary strands forming original dsDNA fragment.

d) Clonal Amplification of DNA Fragments Ligated into Y-Type Adapters.

The clonal amplification of DNA fragments ligated into Y-type adapters provides a built-in validation through quantification of distinct error sources present in particular experimental conditions and results in highly confident estimates of errors levels and their types, which in turn leads to calling mutations with high certainty.

The clonal amplification of DNA fragments in our approach is achieved by limiting the amount of the DNA template before the PCR amplification. The PCR amplification selects for properly ligated DNA fragments, i.e. fragments that have Y-adapter ligated on both ends, with the right amount of the template, for Twin-seq typically in low pictograms, which is orders of magnitude less than in the standard approach.

The number of PCR steps is precisely calculated to avoid depletion of nucleotide substrate for polymerization. This minimizes misincorporation of nucleotides, uneven amplification jumping PCR and other consequences of mispriming and other artifacts like rolling-circle amplification.

The amount of template used for PCR is in the range of picograms, whereas the amount of single-stranded oligos used in PCR amplification is many orders of magnitude higher. The single-stranded oligos used by Illumina are long and their sequences are designed to be non-complementary, which should be sufficient to obtain the desired PCR product. However, due to very high concentration of oligos in comparison with the very low concentration of template, even imperfect complementarity between two oligonucleotides used as PCR primers, results in amplification of the so-called primer-dimer product and affecting so amplification of proper template. Therefore, we modified the standard Illumina PCR amplification procedure to solve this problem. In our protocol the amplification is performed using HotStart tubes (Molecular BioProducts), however with the modifications of the protocol advised by Molecular BioProducts. After mixing the particular PCR reaction components without template and without PCR oligos, we divide solution into two parts. The first part of solution is placed in the HotStart tube and the template and the first PCR primer (PE1) is added, then the tube is placed in 95° C. to melt solid wax attached on the wall of the tube. After wax is melted, we take tube out, cool it down so wax solidifies over the first part of the PCR reaction, and add to the tube, as the upper layer, another part of the PCR solution with the second PCR primer (PE2). This assembly undergoes the PCR amplification using standard PCR conditions with the number of PCR cycles adjusted to the amount of the PCR template. This procedure prevents the formation of primer-dimers between two long PCR primers. We are not concerned with the mispriming originating from premature termination, because the fragments in the sequencing libraries are relatively short. The mispriming leading to primer-dimers is due to the products of annealing between PE1 and PE2 during ramping up of the temperature, therefore PE1 and PE2 have to be initially separated. the products of annealing between PE1 and PE2, therefore PE1 and PE2 have to be separated.

Careful adjustments of PCR conditions in Twin-seq procedure allow for low level of PCR errors, which are independent for both original strands of DNA. Unlike other procedures, there is no need for high scale of clonal amplification to differentiate PCR errors by their uneven presence in the clonal cluster. Lack of requirement for a high level of PCR clonal amplification results in the high efficiency of the Twin-seq procedure.

e) Applying a Second Round of Base-Calling Performed on Clonal Clusters by Averaging of Fluorescence Signal at the Level of Clonal Cluster.

The sequencing instrument outputs electronic signal that undergoes multiple stages of analysis. After the identification of the signal arising from a single DNA fragment, e.g., fluorescence from a polony cluster in Illumina, converting the measured value into DNA sequence is called base-calling. The current implementations of this algorithmic process are far from perfect and its improvements are another important component of Twin-seq.

In sequencing by synthesis, e.g. Solexa/Illumina method, the readout is one base position in each sequencing cycle. This procedure depends on the synchronization of the synthesis to advance by one base position in all places across the sequencing flow cell. However, the synthesis is performed enzymatically and its completeness depends on the local properties of DNA sequences that may prevent the advancement along the DNA strand in all the copies making a particular polony cluster. Such desynchronization of the DNA synthesis is called a phasing error. This problem is highly significant for Solexa/Illumina approach. Several calculation methods were proposed and implemented to improve upon the standard Illumina base-calling.

The base-calling in Twin-seq differs in at least three points from the previously introduced approaches: (1) improved base-calling is performed as a second round of the base-calling; (2) base-calling is performed on the fluorescence intensities averaged over all the reads in the clonal cluster; (3) genome-wide mapping of the phasing error can also be employed. The base-calling performed the second time can be limited to regions that are identified in the first round of analysis as problematic, making it much faster compared to the repeating the procedure on the whole data set. These genomic regions are identified either in a priori analysis of the genome, when the reference genome is known, or by analysis of the consistency of fluorescence intensities within all the reads in a particular clonal cluster. It is known that for some genome sequences, for instance those containing inverted repeats, there are systematic base-calling errors. We can create, for a particular genome and a particular sequencing chemistry, a map of problematic genome locations that will require a second round of the base-calling.

The clonal amplification of the sequencing reads in Twin-seq approach allows for the averaging of fluorescence intensities within the reads in the clonal cluster. As all such reads have the same sequence, the patterns of systematic effects related to phasing will be the same. The process of base-calling in the presence of yet-to-be-determined phasing error involves non-linear calculations that are greatly stabilized by error reductions resulting from the averaging of multiple signals. Such calculations also provide a phasing error estimate that can be used to perform base-calling in other clusters overlapping the same sequence, but having lower-quality data.

An important part of base calling of merged intensities is to distinguish random variations in the signal from the presence of non-random variations (e.g. coincidences containing mutations) in putative clonal clusters. This can be accomplished by clustering/SVD/ICA analysis at the level of raw signal, e.g. fluorescence intensities. Such clustering analysis can prevent false negatives resulting from averaging out mutations with non-mutation data.

f) Analyzing Differences in Sequence within a Group of Reads Forming a Particular Clonal Cluster without Mapping them to the Reference Genome In the Twin-seq approach, the sequencing reads that belong to a particular clonal cluster are analyzed with respect to their internal consistency without using the genomic sequence as a reference point.

In standard approaches analyzing the changes in sequences, the sequencing reads are first mapped to the reference genome, then sometimes re-aligned, and then analyzed for consistency with the reference genome sequence. However, due to inadequacies of reference genome assemblies as well as shortcomings of re-aligning procedures these standard approaches result in problems with calling sequence differences. In repetitive regions, which contain multiple copies of very similar sequences, similar sequences can be inappropriately mapped to the same location, particularly when alternative locations are missing from the available genome assembly. The Twin-seq approach, where inconsistencies in the sequence are analyzed within a clonal cluster based on the internal consistency between sequences largely addresses this problem. If a DNA sequence is fully consistent within all reads in one clonal cluster, it means that this is the original sequence of a dsDNA fragment that led to this clonal cluster. This sequence may differ in a few positions from a group of sequencing reads that belong to another clonal cluster with sequence very similar to the original dsDNA fragment. However, based on the internal consistency between the reads in the clonal cluster, we know that these two fragments cannot represent the same original sequence and should be treated, e.g. mapped and analyzed, separately. This feature of Twin-seq has also a great impact on the genome-assembly algorithms.

g) Mutation Calling can be Performed at the Level of Clonal Cluster by Comparison with Reference Genome In standard approaches, the calling for mutations is performed by comparing multiple sequencing reads originating from different fragments in DNA library with the reference genome. The current statistical criteria used for deciding how many reads have to contain the change in the sequence to call a genomic position mutated are quite arbitrary. The rare mutations and mutations in repetitive regions, where an allele is multiplied and only one repeat is mutated, cannot be reliably identified by this approach. In Twin-seq, the internal consistency of sequences in the clonal cluster can be used to call mutations. For instance, if all clonally amplified reads in the clonal cluster contain the sequence change in comparison with the reference genome, it means that the original dsDNA fragment contained this change as well. Even when many more fragments mapping to this genomic location will not contain this change, it simply means that this mutation was a rare somatic mutation or, in the case of repetitive regions, happened in one of many repeats. We can still identify it and analyze it further.

h) Differentiation of the Chemical Damage from Mutations and Amplification Errors.

The next unique feature is Twin-seq's ability to differentiate the changes in the sequence from the chemical damage and amplification errors introduced earlier.

A single-nucleotide polymorphism or a mutation, in a diploid or polyploid genome, have specific signature in the Twin-seq method—there have to be one or more clonal clusters of sequencing reads that contain a sequence change consistently across all the reads in the cluster. In the standard approaches this information is not available, because each sequencing read represents a different duplex.

The amplification errors have a distinct signature as well. First, the PCR errors will be independent for both strands of the duplex, with the probability of a coincident error happening on both strands in the same place being below $10^{-10}$. Therefore, in the internal consistency analysis, we observe the effects of a PCR error only in sequencing reads arising from one strand of the duplex. The pattern of PCR errors in this group of reads will follow an ABC distribution. Depending on the PCR cycle, in which the error happened, we will observe a specific binomial distribution of sequencing reads containing the changed base. In standard approaches, we cannot analyze it because each sequencing read represents a separate duplex, whereas in Safe-seq approach we could use internal consistency but only within one strand of the duplex, therefore we cannot differentiate PCR errors from other sequence changes reliably.

The chemical damage to DNA has a distinct signature as well: the undamaged strand gives rise to a group of clonal reads with unchanged sequences, whereas the damaged strand of a particular duplex leads to a group of clonal reads with a characteristic pattern of sequence substitutions. The group of unchanged reads is compared in our analysis with the group of reads containing substitutions. The pattern of substitutions represents preferences of DNA polymerases used in sequencing, each of them have specific probability of introducing incorrect base against the damaged base. Therefore, based on the information that reads from only one strand have a sequence changed, and also that the consistency between sequencing reads for that strand should follow a distribution specific for a particular polymerase, allows for attributing to each observed sequence change an appropriate source: mutation, single-nucleotide polymorphism, chemical damage or PCR amplification errors.

This feature allows for determining not only mutations but also patterns of DNA damage, as well as characterizing the specificity of the enzyme used in DNA amplification.

The Twin-seq has numerous features that differentiate it from prior technologies:
- different approach to fragmenting DNA during the library preparation to preserve double-strandedness of DNA fragments in the process;
- using scavengers of hydrated electrons and free radicals during the library preparation to minimize the damage to DNA template;
- recovering information about the directionality of a sequencing read and comparing the sequences of two reads representing the two strands of the original duplex, so the error level is decreased;
- introducing clonal amplification by a single-step procedure to prevent the loss of information about double-strandedness;
- using all those features to monitor and control the level of sequencing errors;
- data analysis that allows for a very extensive validation of results quality and leads to a segregation of contributors to sequencing errors according to their sources;
- elimination of so-called unknown errors, due to the validation based on the internal consistency within a clonal cluster of sequencing reads describing physical/chemical processes rather than error correlates. This leads to unprecedented confidence in sequencing results;
- identifying the amplification of all sequencing biases to gain certainty that all mutations/DNA changes have been discovered;
- potential for validation of experimental procedures to separate the source of amplification biases from other biases introducing uneven coverage. This is particularly important for CLIA-type standards to certify the achieved level of completeness when performing genome-wide testing for mutations.

The Twin-seq approach allows for achieving highly reliable NGS sequencing results with very low level of errors. Both error level and certifiable reliability do not have precedent in any other approach. Due to clear separation of error sources from mutational signals, it is also possible to analyze mutagenic substances or other agents damaging DNA.

The current, high level of errors, in combination with difficult validation, interferes with using NGS methods in medical diagnostics, the development of personalized medicine, discovery of mutational patterns related to environmental exposure, various diseases, and to aging. Uncertainty about the reliability of NGS-derived results is responsible for slow introduction of next-generation sequencing in regulated environments, even though NGS methods provide more comprehensive information, and are becoming less resource-consuming than traditional approaches to mapping mutations.

Advantages Over Current Technologies.

Current sequencing technologies suffer from very high level of sequencing errors and lack of clear criteria to validate the calls for mutation, and differentiate them from sequencing errors.

The next generation sequencing technologies are very promising in respect of providing information about whole genomes, however without the full control over errors introduced either when DNA is isolated and stored, or during sequencing protocols and sequencing process, these methods cannot be fully utilized. The even bigger problem is uncertainty of sequencing results, and related to it, lack of trust in sequencing results.

This is because the error level for sequencing can be statistically estimated; however most of the real-life applications of sequencing require answer whether a particular change indentified in DNA sequence is the real mutation or rather arose from sequencing errors. Currently, this answer is achieved by counting the reads that cover particular genomic position and assuming that specific number of changes means mutation, which is followed by validation using the Sanger method. The Sanger method is currently a validation standard, which is however highly impractical in respect to whole genome research, and also have rather low sensitivity which precludes some of the applications.

The thresholds for the decisions whether a sequence change observed in next-generation sequencing results is a mutation are arbitrary, and until now there were no method to decide if the observed change may be a result of systematic problem in sequencing, because signatures of systematic problems could not be analyzed with the standard sequencing approach.

Twin-seq addresses both problems. The low level of errors is achieved by multi-step procedure that controls the process from the DNA isolation to data analysis step. The low level of errors allows for use of the next-generation sequencing in context previously unavailable to genome-wide studies, for instance studies of somatic mutations, genomic heterogeneity in cancer or mitochondrial disorders are possible.

The built-in validation arising from clonal amplification of DNA fragments in combination with low-level of errors due to utilizing sequence information from both strands of dsDNA fragment provides clear rules of differentiating the sequencing errors from mutations, single nucleotide polymorphisms, and changes arising due to damage to DNA. Twin-seq not only identifies errors reliably but in many cases, for instance in case of base-calling, allows for correcting them or at least provides information about the source of the problem, for instance the levels of DNA damage. For many applications, just identification of errors is sufficient as it leads to reliable results. In regulatory environment, the reliability of the results is often equally important as achieving the low levels of sequencing error, for instance when the results decide about diagnosing disorder or lead to decision about the type of treatment.

EXAMPLES

Example 1. NIH Grant

There are many processes that introduce lesions into DNA. These lesions, when uncorrected, lead to somatic mutations. In the normal cellular state, the fidelity of DNA replication and repair is extremely high, thus the number of somatic mutations per cell is very low. However, over the life of an organism somatic mutations slowly accumulate, which results in modulation and alteration of all cellular functions. Learning how this happens is central to our understanding of many processes, e.g. immune defense [1-3], aging [4-S], and the onset and evolution of cancers [9-11]. Despite the importance of somatic mutations, our knowledge of them is derived from indirect or fragmentary measurements, causing standing controversies and problems with interpretations of the mechanisms involved in aging and cancer. The low levels of somatic mutations and their dispersive nature are the main reasons why the studies carried out so far have relied on either a phenotypic selection of mutations or were limited to special types of mutations: in microsatellites, at restriction sites or in cellular populations, for example in tumor tissues, where selection leads to somatic mutations being locally amplified. Error-free DNA sequencing conducted at a sufficient scale could overcome these limitations and generate comprehensive information about the levels and patterns of somatic mutations. Current, massive parallel sequencing methods generate data at a reasonable cost, but their error level is far above the expected level of the mutations, which in humans is estimated to be in the range of 100-10,000 somatic mutations accumulated per cell, depending on the number of cell divisions, metabolic load and environmental stress.

We have developed and validate an unbiased, genome-wide method to determine somatic mutations by direct sequencing. First we increase data reliability by combining the multiple reads resulting from the PCR clonal amplification. In the second step, which gave our method the name Twin-seq, we compare consensus sequences obtained independently from the two complementary strands present in the original DNA fragment.

Our experimental design results in well-defined statistical independence between groups of sequencing reads, with a robust, safe and efficient estimation of data reliability. The hierarchy of Twin-seq analysis differentiates somatic mutations from other phenomena, such as: single nucleotide polymorphisms, changes introduced during DNA sample processing, pre-mutation changes such as in vivo chemical damage to DNA bases, and base-calling errors. An additional advantage is that the approach requires only a minimal amount of sample per data point. We achieved less than 1 error per 1,000,000,000 (billion) sequenced base pairs. Such an error level makes it is possible to authoritatively map somatic mutations directly and without any prior selection which could introduce bias.

Our invention provides a comprehensive quantification of the level and types of somatic mutations accumulated during the human lifetime in different tissues. The accumulation of somatic mutations has been assessed as a critical factor contributing to aging, cancer development and many other disorders. However, biases, incompleteness of data, and inconsistencies between the results hinder our understanding of the impact of somatic mutations. We address this challenge by using a novel and innovative approach which determines somatic mutations directly by high-throughput sequencing. It combines several advances in sample preparation and data analysis to achieve an unprecedented accuracy of 1 error per billion base pairs. The results have high transformative impact on the understanding of aging, cancer processes, and other diseases where somatic mutations have been implicated. The method is ideally suited to address mutator phenotypes and the somatic evolution of cancer. It also maps and quantifies the effects of DNA damage, so that we can correlate its level with the level of somatic mutations. Another area of transformative impact is the issue of environmental and iatrogenic factors driving the accumulation of somatic mutations, and consequently, the diseases. Here, the robustness, comprehensiveness and internal validation of the method are especially valuable.

We have been interested in the biological role of the structures of nucleic acids for a long time [12-18], and had been planning to use massive parallel sequencing to test some of our hypotheses [19]. We conducted initial experiments to investigate the performance of this technique. First, we analyzed raw images from the Illumina sequencer with in-house data analysis tools and found that the signal-to-noise ratio was much too high to explain the observed level of sequencing errors. It indicated that sequencing errors arise from systematic, and so potentially correctable, chemical and physical effects. The preliminary results confirmed that the sources of systematic effects can be identified and corrected, either during data analysis or by modifying experimental protocols. Our experiments revealed that we can identify somatic mutations with very high accuracy: we extrapolated that we can achieve the error level below 1 per a billion base pairs for a multi-read consensus sequence generated from a single DNA fragment.

A breakthrough aspect of our Twin-Seq method is the change in the experiment that provides fully independent sequencing information for each of the two complementary strands of the dsDNA fragment used to prepare a sequencing library. We also added a series of other improvements to reduce experimental errors and introduced validation tests that differentiate the sources of systematic effects, including DNA chemical damage. We based this design on our previous experience in radiation chemistry [20, 21], nucleic acid structures [12-18], and in advanced methods of analyzing data with complex patterns of uncertainties [22-26]; knowledge that we acquired in the field of crystallography, which encompasses a number of molecular biology and biophysics techniques. We performed a thorough investigation of the methods used to determine somatic mutations [27-30] and became convinced that none of the current approaches is equally comprehensive or has a comparable sensitivity.

High-throughput sequencing has already attracted interest as a potential method for identifying somatic mutations. The article describing the most sensitive sequencing experiment stated that the authors could not determine which fraction of the observed sequence changes arose from somatic mutations and which from possible false positives [30]. Our expected error level of $10^{-9}$ is sufficient to eliminate the gap in knowledge resulting from the ambiguities and incompleteness of the current data with respect to the level of somatic mutations.

A novel, comprehensive and highly sensitive method to determine somatic mutations constitutes a breakthrough that can transform a number of important areas. For instance, somatic mutations have been implicated not only in aging and cancer [4, 5, 31], but also in heart disease [32], autoimmune diseases [33], and other disorders [34]. For cancer, the obvious implication will be in diagnostics, and possibly also in treatment, where identification of mutator phenotypes may lead to the design of individualized treatments based on the principle of synthetic lethality. In the understanding of aging and cancer, the central issue is knowing the number and type of somatic mutations that can drive these processes. At the moment, the baseline level of somatic mutations in different tissues is highly uncertain [35]. The relative contributions of DNA damage and somatic mutation in aging is unknown [36]. This realization directed our choice of the subject matter.

Our approach combines experimental advances with novel data analysis methods to achieve a very low and well-controlled level of sequencing errors, which will allow for an unambiguous, unbiased determination of somatic mutations in a genome-wide manner with massive parallel sequencing methods.

Accumulation of somatic mutations is a complex process resulting from replication errors and incorrect repair of damaged DNA. Studies of mutation accumulation in germline cells having a well-defined pattern of cellular divisions provided expectations of a minimum of about 100 somatic mutations acquired during the lifetime of a cell [31, 37, 38]. This baseline number likely increases when cells replicate more frequently or are exposed to DNA-damaging factors, e.g. reactive oxygen species, present in the environment or produced in metabolic reactions [39, 40]. It is obvious that accumulation of somatic mutations is deleterious, but understanding the extent of their impact is hindered by the lack of precise and authoritative methods to measure their levels and spectra [35, 36, 41-43]. Such methods are difficult to develop because of the very low level and high dispersion of somatic mutations. The estimated frequency of somatic mutations is $10^{-8}$ to $10^{-10}$ per base [44]. In the simplest model of synchronously replicating cells, a particular somatic mutation will be present on average in very few copies in a large population of cells. That means that the expected biological signal for measuring somatic mutations is very low, making its detection difficult in the presence of the high background generated by experimental errors and unaccounted systematic effects.

The insufficiency in mapping and quantifying somatic mutations affects all areas of biology where somatic mutations play a role. Aging and cancer studies are the two biggest fields that could be transformed by development of better methods. In both these fields, it is critical to determine the degree to which the number of accumulated somatic mutations depends on the number of cell divisions, on the metabolic load, and on particular mutagenic influences of the environment. If we could have the numbers and patterns of somatic mutations with reasonable certainty, the quantitative prediction methods correlating those mutational spectra with cellular states could be developed. The related field of oxidative damage studies would also benefit greatly from development of better methods quantifying somatic mutation [45]. The lack of accurate data defining how oxidative damage affects the level of mutations in human tissues diminishes our ability to draw biological conclusions [46, 47]. In the absence of reliable and precise data, the subject is debated [46, 48]. The process of somatic evolution of cancers is not well understood [49-51], but it is clear that it plays an important role in disease onset and during metastasis [37, 51, 52]. Results such as maps of the full spectrum of somatic mutations from different biopsies of the malignant tissue and its potential metastases would provide an invaluable insight into the mechanisms of the somatic evolution of cancer. Environmental factors influence the rate and levels of somatic mutations acquisition, leading to modulation of cellular programs, which affects the health of cells, tissues and organisms. Studies of their impact as well as formulations of preventive strategies and regulations would also benefit from better methods quantifying of somatic mutations.

There have been many efforts to study somatic mutations (reviewed critically in [35]). The established approaches use a selection by metabolic screen, e.g. hypoxanthine phosphoribosyltransferase (HPRT) gene. Those assays, depending on the mutation reporter used, have one or more of the following shortcomings: (1) introduce an unknown level of selective bias; (2) require cultivating a cell line, severely restricting the range and type of questions asked; (3) cannot be used in humans. Most importantly, they are all single-locus assays. The genome-wide random mutation capture assay has excellent sensitivity [53]. However, the detected target is the 4 bp TaqI restriction site, which is distributed over the whole genome. All TagI sites together in the genome comprise only 0.4% of its content, which makes it unsuitable to study mutation spectra in detail. In genome-wide studies of mutation spectra, some approaches focus on somatic mutations amplified clonally in a group of cells, e.g. cancer. In this approach, somatic mutations in the cell that started a clonal line are identified by multiple occurrences in different, sequenced DNA fragments [54, 55]. This method can identify the mutations that drive the phenotype, but is not a general approach to study the spectrum of somatic mutations, which also contains unamplified clonally, rare mutations.

Three groups proposed direct sequencing for finding somatic mutations in healthy cells. The first approach uses Sanger sequencing, which severely limits the sensitivity of the method to levels worse than $10^{-4}$ [29]. The other two approaches perform high-throughput Illumina sequencing on libraries generated from DNA either synchronously [30] or asynchronously (WGA) [27, 28] amplified prior to the preparation of the sequencing libraries. This is followed with analyzing the consensus between amplified reads. However, polymerase errors may also be amplified, and may appear simultaneously in multiple reads. The article describing the method using synchronous PCR amplification identified 3 to 9 sequence changes in PCR clonal clusters per 1 million bases [30], without differentiating which part was generated by somatic mutations and which by false positives. The authors of the paper that used the WGA observed a level of $10^{-7}$ sequence changes at lowest [27]. In both publications, authors admitted that they were unable to determine the baseline levels of somatic mutations frequencies due to the error level exceeding the baseline level. Neither approach can differentiate polymerase errors from somatic mutations solely by the difference in the correlation patterns of sequence changes between the reads. In the discussion, both groups considered statistical mixture modeling of correlation patterns as the solution. However, the groups did not present such solutions and did not discuss how to validate the statistical assumptions used to design the mixture models.

Figure 1B:
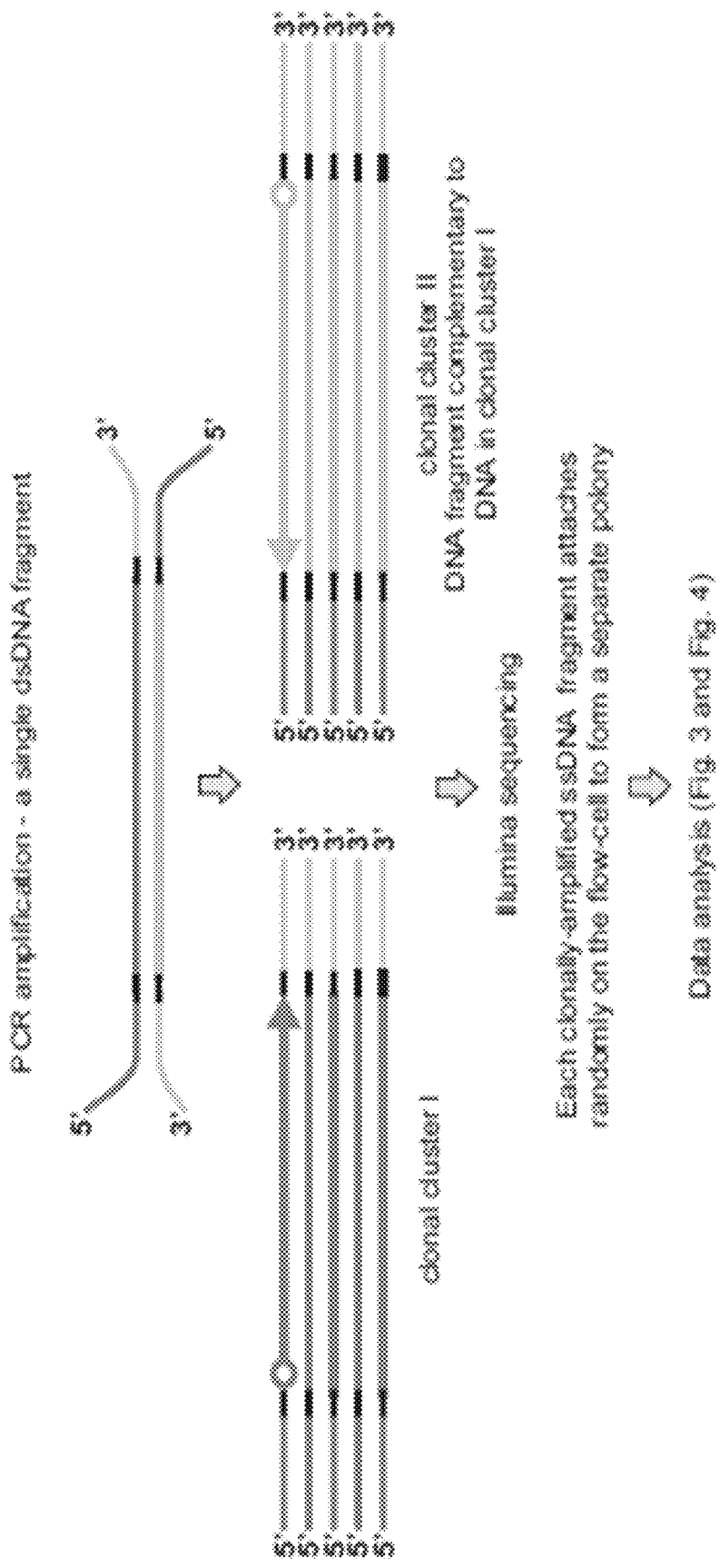
FIG. 1B. Clonal-amplification introduced during selection of properly ligated fragments by PCR.

Our Twin-seq method (FIG. 1) overcomes all the described difficulties. It is very sensitive, unbiased, and directly provides information about mutations across the whole genome. A built-in redundancy check allows for the differentiation of sequencing errors and rare somatic mutations. This is achieved by preserving the information about the strand origin through the whole procedure of library generation. We modified the procedure of library preparation to assure that fragmentation will yield double-stranded DNA fragments, which will retain their double-stranded form until the completion of the sequencing adapters' ligation. During the very first PCR cycle, the ligation product is denaturated and the subsequent fate of the separated DNA strands, together with their amplified products, is independent from each other with respect to the potential introduction of errors. However, the sequencing adapters used in ligation are not double-stranded; they have a special, Y-structure design. The adapters' design in combination with the polarity of the complementary strands results in a ligation product that has built-in asymmetry. Therefore, even after PCR amplification, a sequencing read contains information about the polarity of the original strand (FIG. 1). This feature is used in the strand-specific RNA sequencing, but was never employed in the context of uncertainty analysis in dsDNA. An essence of our method is to use this feature to generate a hierarchy of consensuses between the sequencing reads and use those consensuses as validation criteria.

At the level of PCR amplification, which in standard Illumina protocol selects the properly ligated fragments, we restrict the amount of starting material to obtain multiple, clonally-amplified reads from the original DNA fragment. Each dsDNA fragment results in two identifiable groups of paired-end reads. Each identified group has to originate from a single DNA strand, so we should also observe the group that corresponds to its complement (FIG. 1). The level of PCR clonal amplification should be be sufficiently high so as: (1) to increase the probability that the reads from both complementary strands are observed, (2) to reach the desired reliability of the result, (3) to improve the uncertainty estimates and the diagnosis of problems.

We performed initial experiments to identify experimental factors contributing to sequencing errors. We sequenced three strains of *E. coli*: one wild-type strain MG1655 and two mutator strains with defects in their mismatch-repair pathways. Samples were prepared according to the standard Illumina protocol, except for custom multiplexing and modification at the PCR step (FIG. 1). By diluting the input sample to contain 200 fg of DNA and increasing the number of PCR cycles to 27, we introduced about 25-fold clonal amplification. We adjusted conditions to prevent jumping PCR and other PCR artifacts [56]. To increase the reliability of clonal cluster identification, we added randomized bases to the sequencing adapters at the start of the read position, differentiating most of the potential sequence coincidences. The sequencing was performed on Illumina GA-II$_x$ with paired-end reads 130 bp long. We started with the Illumina pipeline up to the stage of base-calling, after which we used only custom-built programs with the exception of Bowtie [57], which was used to map the reads onto the *E. coli* genome.

Part of the sequencing reaction for each strain was used to determine if the genome of a cell that started a particular culture did not have any earlier accumulated mutations, i.e. before arrival to our lab, with respect to the reference genome. After correcting for the presence of those few mutations, we analyzed all other discrepancies, particularly those consistently present within each group of clonal copies. We identified four well-defined groups of effects leading to correlated errors in sequencing reads. The errors in the first group happen when a polony on the surface of the flow-cell is split into two or more sequence reads by the Illumina software, in which case one single stranded piece of DNA is treated as multiple observations. This effect is easy to recognize in sequencing data, as those reads with almost identical sequences will have flow-cell coordinates less than 3 pixels apart on the detector. The second category consists of errors introduced during PCR amplification. This will result in the same error in a sequence in one or more reads of a clonal cluster. The PCR amplification errors will have a characteristic probability distribution, discussed later. The errors in the third category result from chemical alterations of base in a single strand in a double-stranded fragment of DNA. This alteration can happen inside the living cell or later, during sample handling, but prior to the PCR amplification step. This category will have a distinct probability distribution of a single chemical event generating multiple errors in the PCR product. Those three sources can generate correlated errors only in the reads originating from a single DNA strand, as they do not affect the complementary strand; therefore it is relatively easy to identify them. Moreover, in our assay, such PCR- or chemically-induced errors will be rare, with an expected frequency of less than $10^{-5}$; hence, the frequency of their coincidentally being on both strands in the same place will be $10^{-10}$, an acceptable level for our goals.

Figure 2:
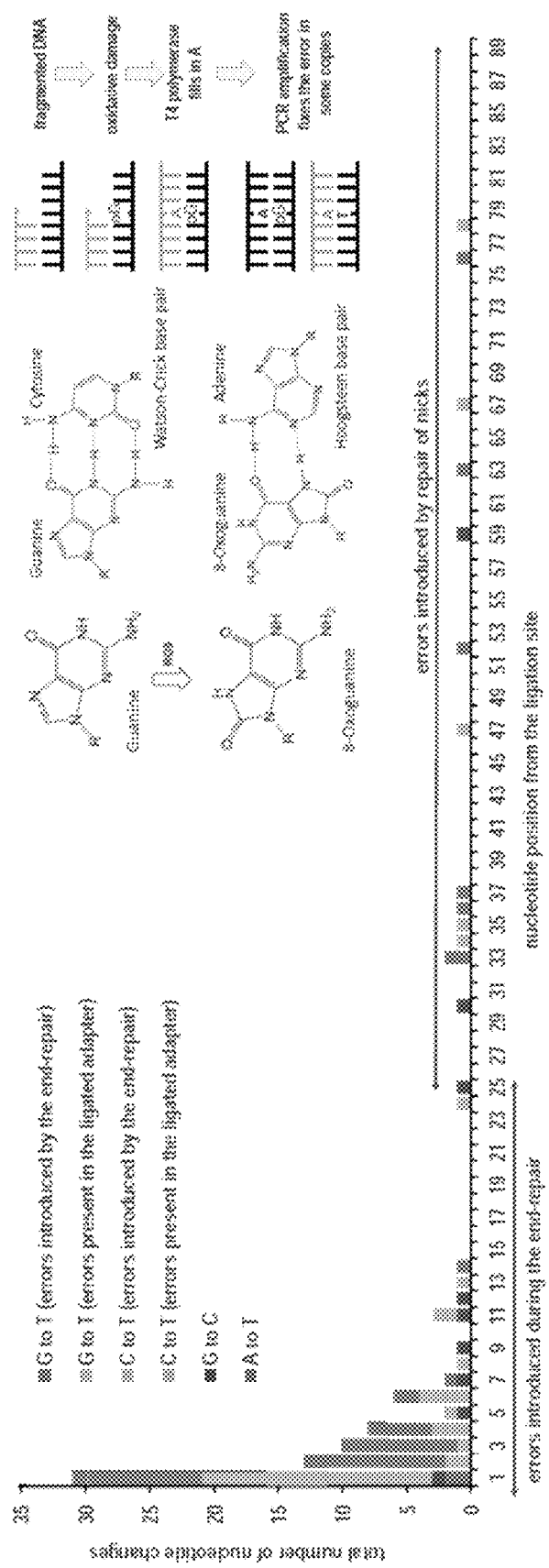
FIG. 2. The distribution and pattern of errors accumulated during the end-repair.

However, the fourth source of correlated errors can mimic somatic mutations. Standard sample preparation can introduce a coupled error on complementary strands, which will have the same signature as a somatic mutation. Standard Illumina sample preparation that disrupts DNA by sonication or nebulization introduces uneven breaks on both strands, which need to be repaired enzymatically. The process is performed using a T4 DNA polymerase, which uses the single stranded overhang as a template. The overhang sequence may contain a chemically altered base, e.g. 7,8-dihydro-8-oxo-2-deoxyguanosine (8-oxo-dG) and in in vitro conditions the polymerase will insert with some frequency an incorrect nucleotide in the complementary strand (FIG. 2). The damaged base may with some frequency also induce the same mispairing later during PCR amplification. Consequently, the same chemical event causes a coupled sequencing error that appears in two groups of reads corresponding to two complementary strands. The same type of coupled error may arise when the original DNA duplex contains a nick on one of its strands, which is then repaired by the combined actions of exonuclease digestion and strand copying, starting from the nick. In our preliminary studies, these repair effects manifest themselves as a surplus of coupled errors in both strands, concentrated close to the ligation site of sequencing adapters (FIG. 2).

Because the T4 DNA polymerase fill-in reaction always proceeds in the 3' to 5' direction, we can recognize the strand where the error originated. In the FIG. 3, the types of coupled substitution are defined with respect to the strand with putative DNA damage. In the data, the strands with putative DNA damage correspond to the start of the first paired-end read for both groups of reads, each representing one of two complementary strands. The results of the fill-in reaction will be present at the start of the second paired-end read at complementary positions. The chemistries generating damaged bases are very diverse, and we expect for errors of this type to observe very different frequencies across all 12 possible types of mutational substitution. In contrast, the frequency for complementary types of substitution (e.g. G→T and C→A) for somatic mutation should be the same, because the mutated positions are only differentiated by the direction in which sequencing is performed. Additionally, while fill-in originating errors should concentrate close to the ends of sequenced DNA, somatic mutations should be randomly distributed along the reads.

Our data for the MG1655 wild-type strain of *E. coli* show coupled sequence-change events close to the sequencing start for only four substitution types: G→T, G→C, A→T and C→T (FIG. 2). We did not observe any such events for the complementary substitutions. It indicates that the source of these sequencing changes is damage to the bases in the library rather than somatic mutations. The most frequently observed change is a G to T substitution, which would result from the oxidation of G to 8-oxo-dG, which can be generated during the storage of DNA samples [45]. Some of the changes occurred at distances from the ligation site longer than those expected for the size of the overhang. We attribute them to nick repair rather than to the fill-in repair of the overhang.

After removing from the pool of observed coupled sequence changes the errors generated by fill-in and nick repair reactions, we observed in wild type MG1655 *E. coli*, a single coupled (T→G, A→C) change in 31,000,000 sequenced positions obtained according to our coverage and quality criteria. The presence of a single mutation is consistent with our expectation of ~0.7 mutations present in the wild type *E. coli* genome after ~300 generations of cells with a faithfully working replication apparatus [58]. This was proof that our strategy for avoiding false positives was successful. At this point, we have already achieved sensitivity about 30 times higher than any other, unbiased, genome-wide approach for mapping mutations. However, while the level of somatic mutations seems to be higher in eukaryotic organisms [59, 60], the complexity of data analysis, the genome size, and the number of potential sources of systematic effects also increase. Therefore, we developed additional improvements, providing our Twin-seq method even greater sensitivity.

First we refined the sequencing library preparation. Improvements in detection sensitivity require both scaling-up the amount of DNA to be reliably sequenced and reducing sequencing errors and other sources of false positives. Our goal is to identify somatic mutations at $10^{-9}$ error stringency using one sequencing lane in Illumina Hi-seq 2000 and 1.5 to 2.0 Gbp of sequencing data obtained from *Escherichia coli* gDNA. This goal does not include rejecting highly-repetitive regions, discussed later.

A critical improvement to enable the Twin-seq method is to avoid coupled errors arising from the end-repair reaction after DNA fragmentation. We can eliminate this reaction entirely, by fragmenting the DNA with double-strand-specific, apoptotic DNA endonuclease DFF40, which has been thoroughly characterized and produces blunt ends with a 5' phosphate extension [61-63]. The fragmentation is followed by extending the blunt ends with dA, and the ligation of sequencing adapters, neither of which introduces significant sequencing issues.

We found PCR reactions a tolerably small contributor to sequencing errors. Phusion polymerase, used in our preliminary studies, generates on average $4.4 \cdot 10^{-7}$ errors per base, per replication cycle (NEB materials), producing a contribution of $\sim 10^{-5}$ to the error frequency of a single read. An additional contribution of $1.5 \cdot 10^{-5}$ comes from the error rate of the Bst DNA polymerase [64], which during polony generation synthesizes a first copy of a single-stranded DNA piece annealed to a short oligonucleotide covalently attached to the Illumina flow-cell. The original strand is removed and the Bst-generated copy becomes the template for the whole polony.

Figure 3:
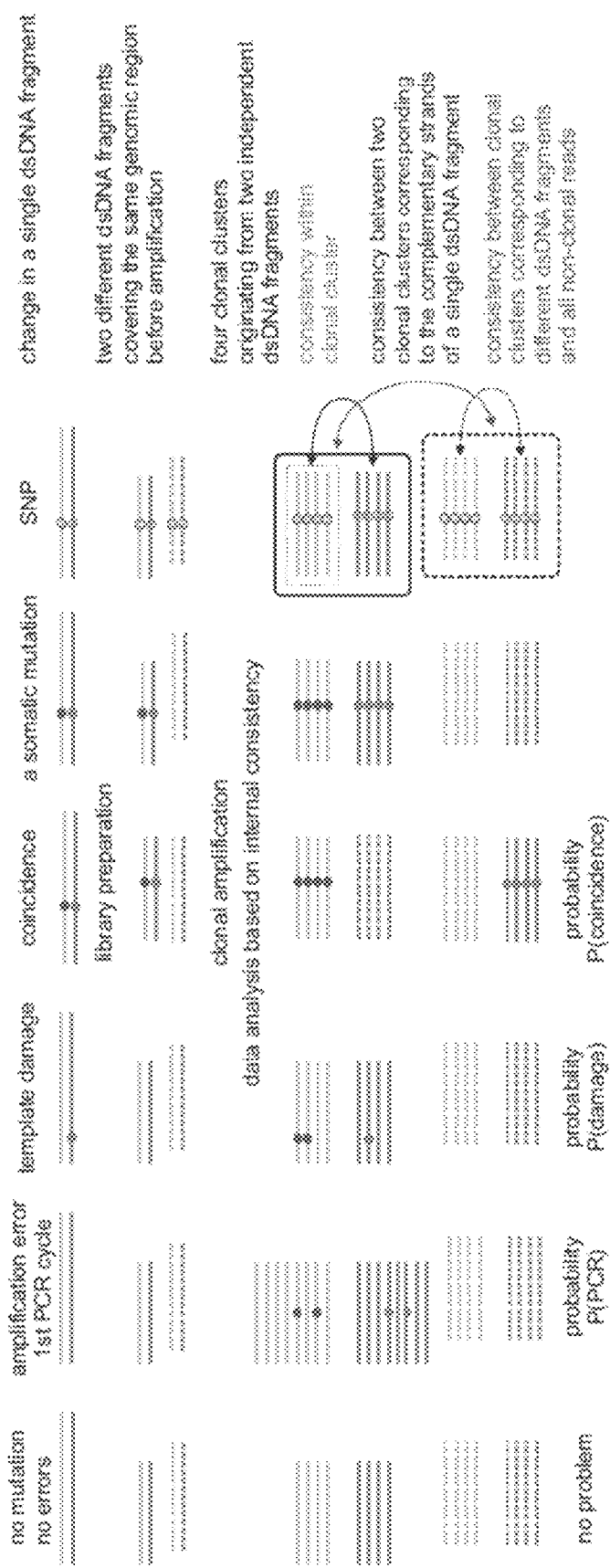
FIG. 3. The hierarchy of sequencing consensuses between clonal clusters; each effect will have its own signature with an associated expected magnitude of the effect.

The errors introduced in PCR are highly dispersed, with the majority of correlated errors originating from the first PCR cycle. For instance, the probability that two clonal copies with the same pattern of sequence changes resulting from the same error in the first PCR cycle is $\frac{1}{4} \cdot 4.4 \cdot 10^{-7}$. If one adds the contribution from subsequent cycles, the probability of such an event is $\frac{1}{3} \cdot 4.4 \cdot 10^{-7} = \sim 1.5 \cdot 10^{-7}$. This level is sufficiently high to be identified in our analysis, but does not generate problems in the Twin-seq method, because Twin-seq uses information about clonal copies resulting from the PCR amplification of the strand complementary to one with PCR errors. PCR error level is often perceived to be much higher. One reason is confusing the PCR reaction that generates the error with the chemical damage to the template, which will induce formation of incorrect copies even if the PCR amplification is faithful. In our approach, we can identify the chemical damage existing prior to the PCR step. The chemical damage to a particular base results in multiple strand-specific errors in a clonal group of reads, which do not correlate with errors in the complementary clonal group (FIG. 3). We inadvertently created chemical damage during our preliminary experiments and our analysis could recognize it as a specific type of error that needs to be controlled better. The perception of PCR as a main source of errors may also result from frequently described PCR artifacts [56]. We were meticulous with the quantification of the template and the estimation of the product mass to avoid detrimental changes in reagent concentrations. We observed that under the standard PCR protocol conditions, when starting with 200 fg of ligated DNA, the amplification of mispriming products would overtake the DNA library and use up all the nucleotides. We identified the general PCR conditions where the desired product was the main fraction of the amplified product and did not use up much of the nucleotides present in the PCR buffer. During data analysis, we realized that the ligated libraries, stored at 4° C. when the PCR conditions were tested, accumulated some level of chemical modifications that resulted in a quite significant number of sequencing errors, mainly G→T substitutions (guanidine oxidation), at the level of $6 \cdot 10^{-4}$. The contribution of this effect to the false positive mutation calls was nevertheless small. The chemical modification affects only one strand, therefore the change occurs in only one type of clonal cluster, and is not present in the clonal clusters corresponding to the complementary strand. Counting it as a somatic mutation would require a coincidence of errors in the same position on both strands of the dsDNA fragment. This occurs about 100 times less frequently than T4 polymerase-induced coupled errors (FIG. 2). We also found that the prolonged storage of ligated DNA affected its amplification by PCR, reducing our chances of finding clonal clusters from both strands of dsDNA, which is crucial for the success of our analysis. We attributed it to the deamidation of cytidines, resulting in the formation of uracyls which cannot be use as a template by the Phusion polymerase. Therefore, we modify the procedure to decrease potential for oxidative damage and increase efficiency of finding clonal clusters for both strands of the dsDNA library fragment. We will perform all reactions faster and will add scavengers of radical and hydrated electrons. The most probable source of damaging radicals is contamination with iron cations, which could be removed by chelation. However, we cannot add chelators, because it would unpredictably affect the enzymatic reactions used in the library preparation that depend on magnesium concentrations. Therefore, we instead add micromolar concentrations of sodium iodide and sodium nitrate, which we found to be effective in scavenging hydrated electrons and hydroxyl radicals, respectively [20, 21, 65, 66]. The sodium iodide was used in procedures minimizing the oxidative damage to guanidine, although without invoking the scavenger justification [67, 68]. They have a minimal contribution to the ionic strength, which is easy to compensate for in the buffer composition. We reduce the chemical damage by a factor of at least 10 or 100.

To fully diagnose all sources of chemical damage, we probabilistically model correlated errors in clonal cluster reads. It is an improvement over existing methods of modeling correlated errors [30] by considering chemically-modified DNA bases, for instance 8-oxo-dG, as intermediates in error generation. These modifications form after replication in a limited number of chemistries involving oxidative damage or deamidation, the reactions having their own dynamics that need to be modeled. Unlike the standard bases, these modifications may create multiple outcomes during subsequent amplifications, which depend on the specificity of the DNA polymerases used in PCR [69, 70]. We extend the probabilistic model to include also other PCR-generated errors.

The prevention of DNA damage should also increase ~3-fold our chances of finding reads from both original DNA strands, resulting in ~2-fold improvement in efficiency, with respect to the main limitation, which is the cost of sequencing reads, not the amount of starting material. We increase the scale of sequencing by switching to Hi-Seq 2000 with v3 chemistry to produce about 200 M purity-filtered reads per sequencing lane, ~6 times more than in the preliminary studies. In the preliminary studies, the clonal amplification factor was quite high, ~25-fold per strand, to enable many types of error diagnosis. We gradually improve efficiency by decreasing the clonal amplification factor to ~4-fold per strand, which results in ~4 times improvement in efficiency. It is possible due to better understanding, elimination, and modeling of error sources, which provides us with sufficient confidence in data with a lower clonal amplification factor. While the overlap between paired reads provides additional validation in data analysis during method development, selecting longer DNA fragments to avoid overlap additionally increases efficiency.

Error reductions and control of systematic effects arising from library preparation is one component leading to the unprecedented sensitivity of our method. Another results from better analysis and detection of instrumental errors and effects. The majority of sequencing errors happen during sequencing by synthesis and the associated fluorescent readout. The dominant part of these errors has a random character; they come from electronic noise and largely from imperfect deconvolution of the overlapping polonies. While deconvolution error can have some elements of systematic error, due to effectively random patterns of sequences in partially overlapping polonies, this systematic error is not likely to be correlated between the reads, so it can be considered random. The overlap between polonies, which originated in random positions on the flow cell, varies from a complete overlap, resulting in purity filtering rejection by Illumina software, to an almost complete separation. A higher degree of overlap generates an inherent increase in uncertainty of the deconvolution results. Since the pattern of the overlaps is a consequence of the initial random hybridization of the target DNA on the flow-cell, it is quite diverse and the reads, even those originating from the same DNA sequence, may have a quite different overall signal-to-noise ratio prior to base-calling. Base-calling is a complex process, in which the deconvolved fluorescence intensities are converted to the assignments of the most probable DNA base with the associated uncertainty of this assignment. This uncertainty can be expressed as a scalar (Q value) or a vector (colored Q-value), and describes the relative likelihood for four possible bases. In the Illumina technology, each sequencing cycle involves a polymerase that advances by one position in all reads simultaneously, by incorporating in those reads a specific base, complementary to the template, labeled by a fluorophore distinct to each of the four bases and blocked to prevent further polymerization. However, occasionally the polymerase advances by two bases or fails to advance. Polony-wide delay due to incomplete base incorporation is called phasing, the running ahead is called pre-phasing, and the consequences are called phasing error. The Illumina software recognizes and corrects for the average level of phasing and pre-phasing in segments of the flow-cell. However, we observed, like others [71], a very pronounced strand-specific increase in the error levels at particular genomic positions. We address this issue in our iterative approach to error characterization in data analysis.

Each piece of dsDNA can produce two clonally amplified clusters of reads, each cluster originating from one strand of the original dsDNA (FIGS. 1 and 3).

Figure 4:
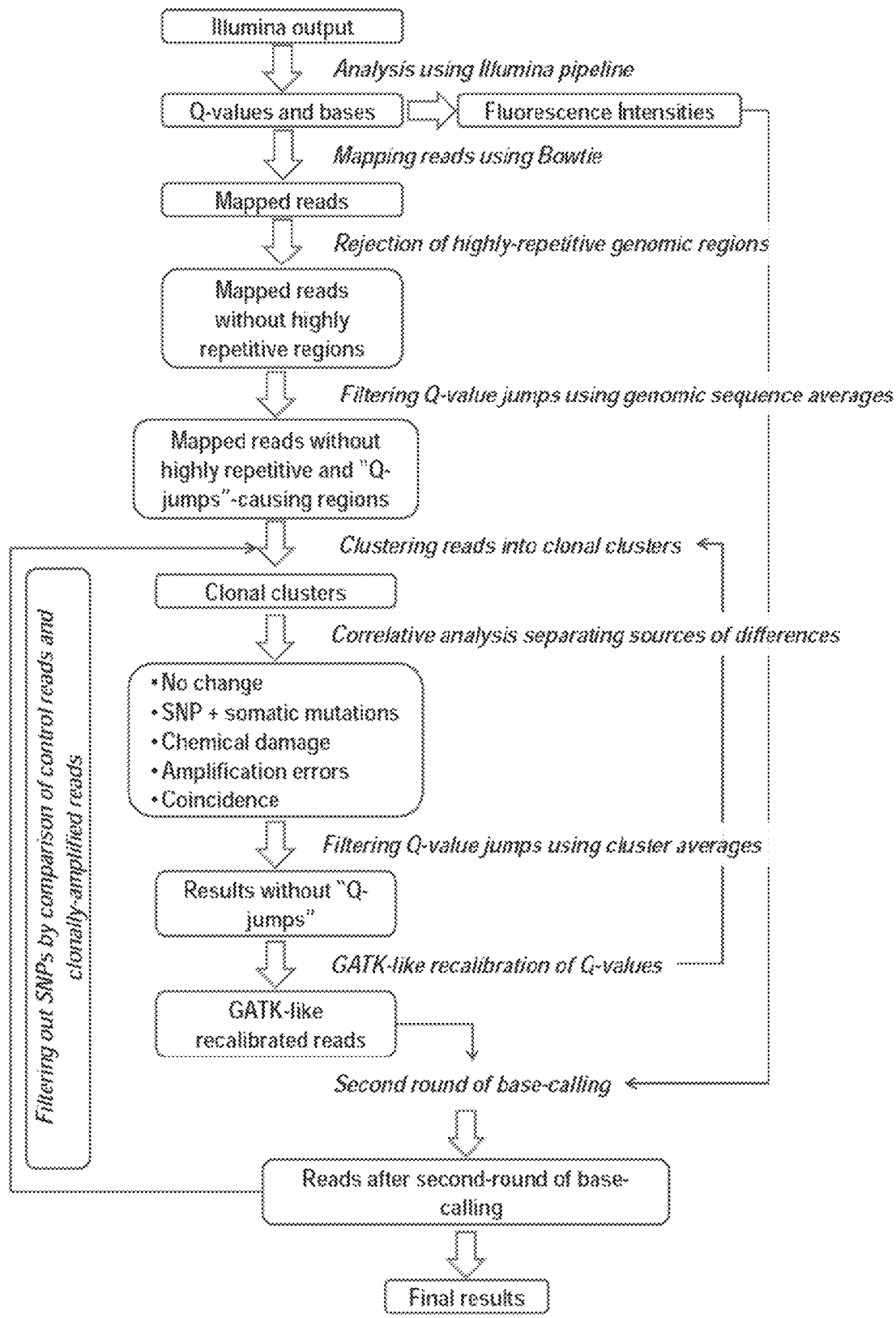
FIG. 4. The flowchart of our data analysis scheme.

We perform the polony identification, fluorescence signal estimation, base-calling and initial, so-called purity filtering with standard Illumina software (FIG. 4). The next level of quality filtering is based on both segments of a paired-end read exceeding a specified quality threshold. We then cluster sequences to identify clonal copies, first for each strand separately, then combining pairs of clonal clusters. This is performed through a hierarchical analysis: first, a fast, rough clustering is performed, with criteria set so as not to miss a potential hit, at the cost of merging some clusters together. In the next step, a more elaborate, singular value decomposition (SVD) analysis differentiates random events from potential systematic differences within the cluster, which are classified on the basis of correlations within the cluster as either arising from similar sequences within the genome (coincidences and/or polymorphisms) or from correlated sources of error, e.g. from chemical damage or PCR amplification. Decision thresholds in this analysis rely on the probabilistic error model that is also subject to improvement after the initial clustering is performed. To enable Bayesian reasoning, we explicitly model the events that can generate errors in multiple reads of the particular clonal cluster. In the normal use of Illumina sequencing, the clonal amplification reads are typically filtered out before aligning multiple reads to identify mutations or polymorphisms. Using the Q-values for the remaining reads to define probabilities in Bayesian reasoning would create false positives. Q-score recalibrations procedures, such as GATK [72] have been implemented, resulting in $10^{-6}$ level of false positives in SNP calls [73]. However, even with this improvement the existing approaches capture only part of the problem, and final mutation and SNP calling relies on criteria that are difficult to validate, involving visual inspection of read pile-ups or, possibly inefficient use of threshold criteria [27, 28, 30]. A more comprehensive solution to this problem is an important part of our invention.

Figure 5:
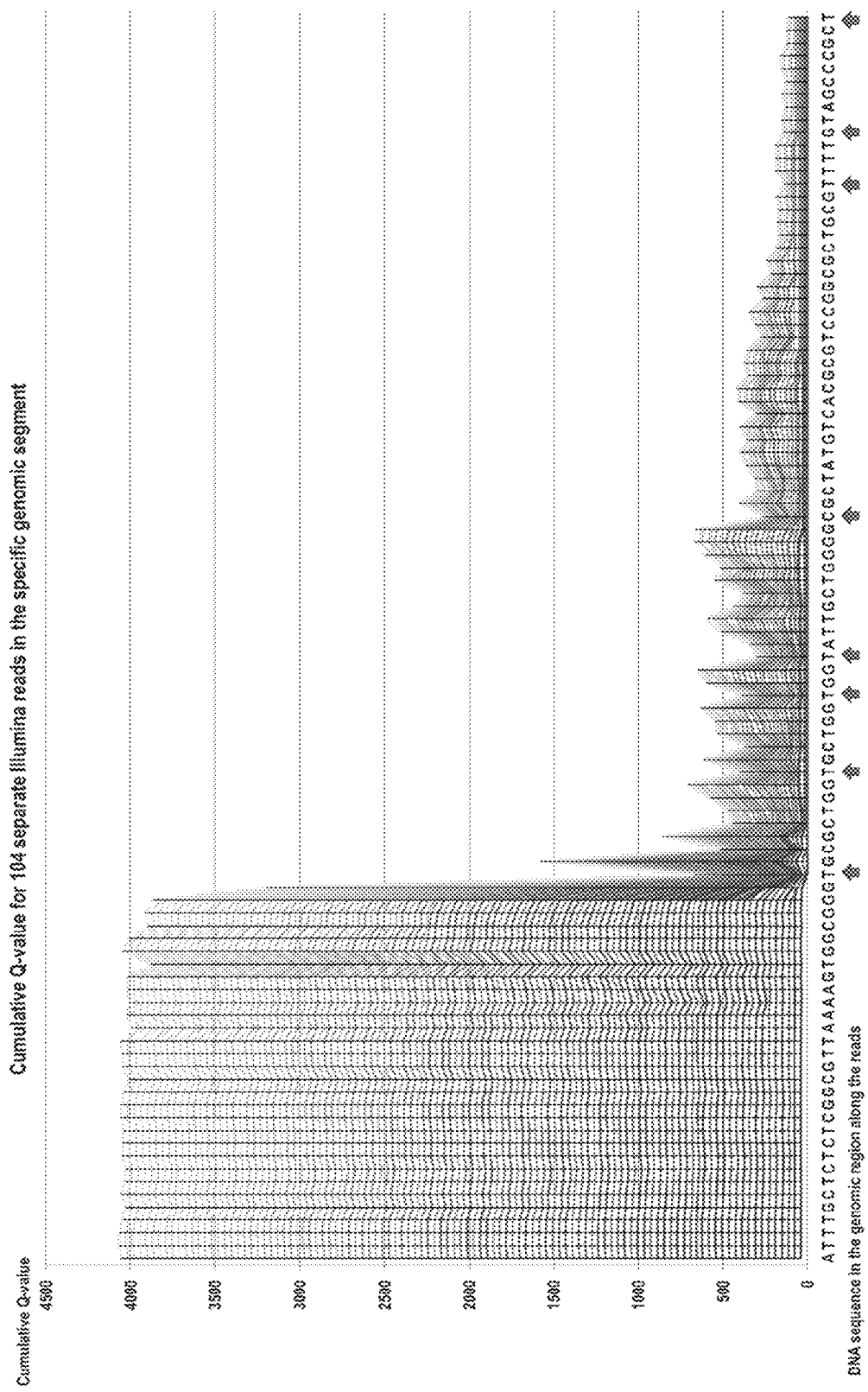
FIG. 5. A cumulative Q-value (top panel) for 104 reads of 130 bp length that aligned to positions 48308 to 48405 of the forward strand in the genome of Escherichia coli strain K-12, MG1655.
Figure 6A:
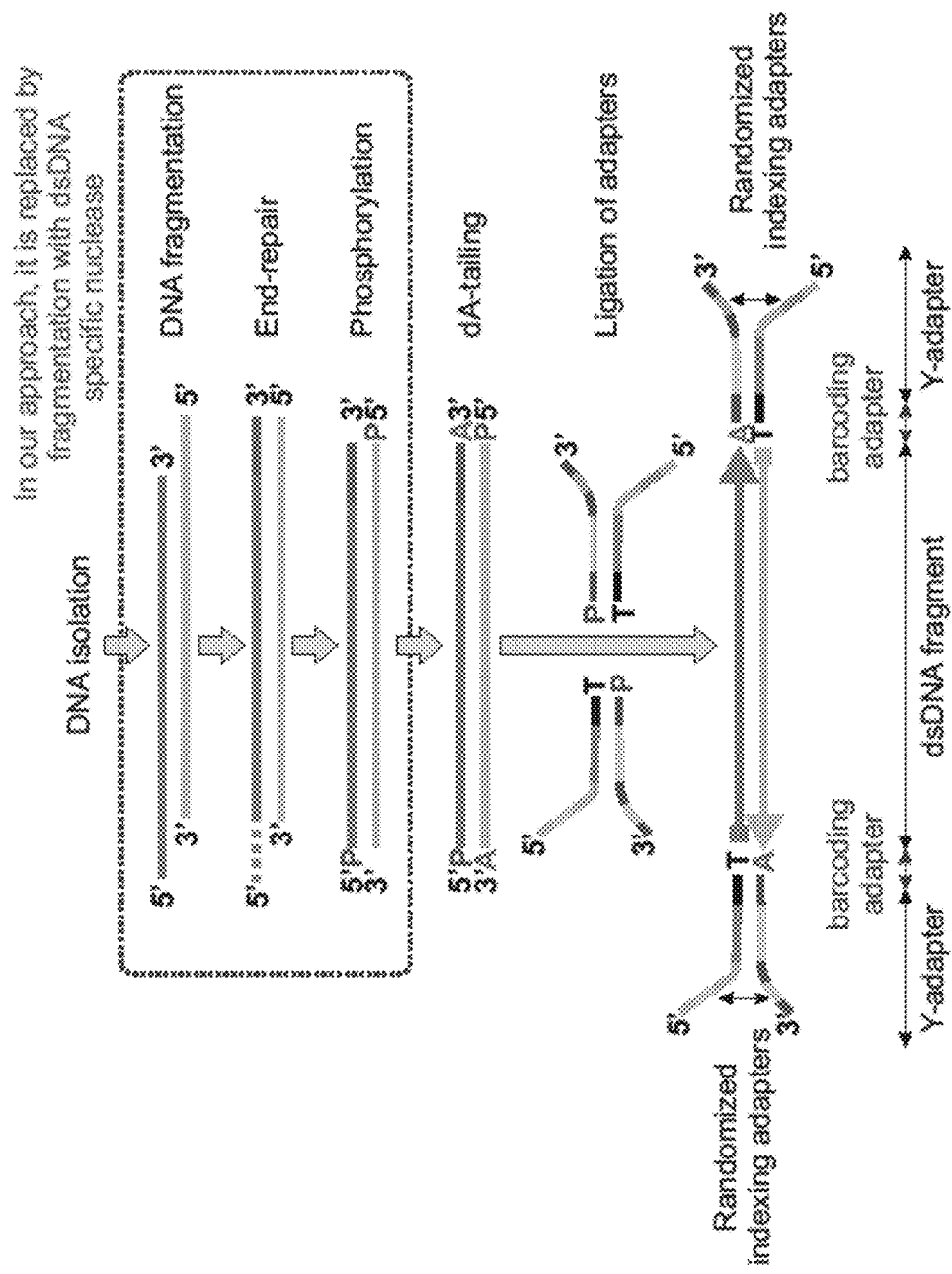
FIG. 6A. Schematic view of the sequencing library preparation with the standard protocol of Illumina, and with our modifications.
Figure 6B:
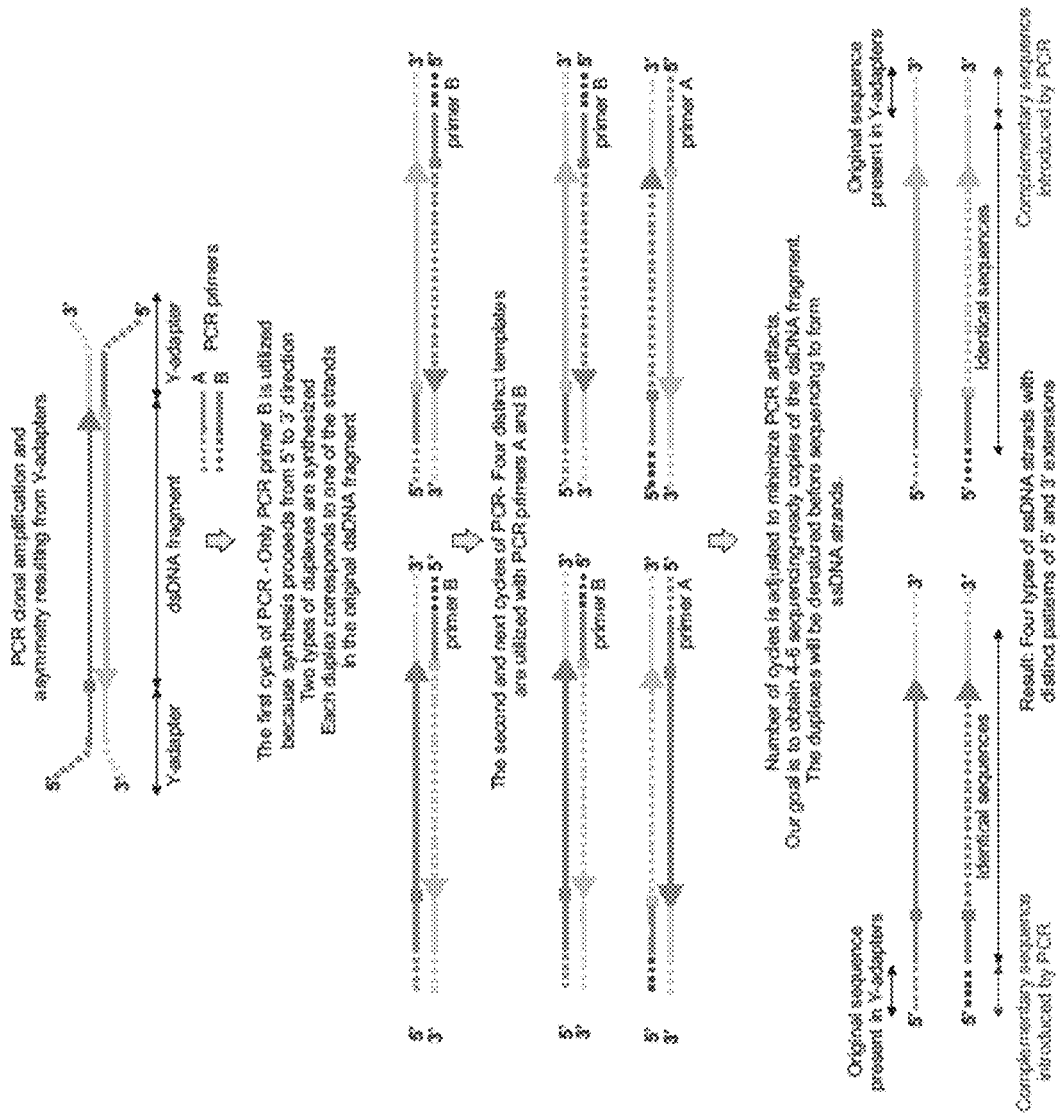
FIG. 6B. Schematic view of the mechanism that preserves information about the directionality and identity of DNA template strands during PCR amplification, which generates the sequencing library.
Figure 6C:
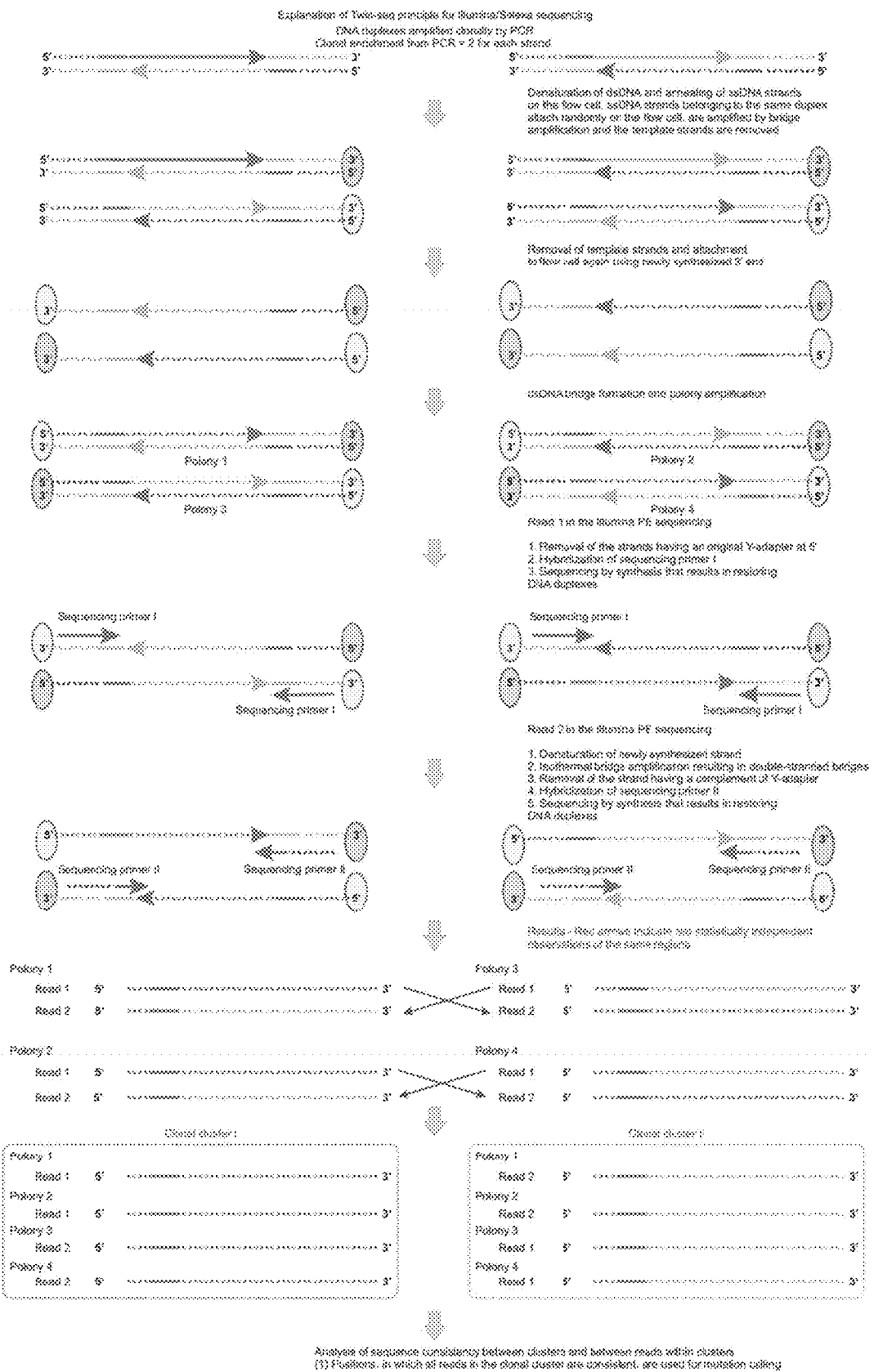
FIG. 6C. The Twin-seq principle in Illumina/Solexa pair-end sequencing.

We found that a troublesome aspect of base-calling error in Illumina has the following properties: a) the effect is highly reproducible when encountering particular sequences ahead of the read position, which often have indications of a higher-order structure formation, e.g. DNA hairpins or quadruplexes; b) there is no decrease in fluorescence signal, so the elongation by the DNA polymerase has not terminated; c) all subsequent positions have increased read-out error, which is characteristic of phasing, where the extent by which polymerases are out of phase in the sequence position can only increase as the read progresses. This sequence-specific desynchronization generates a high level of errors (FIG. 5). The problem can be recognized not only by incorrect base-calls, strongly biased towards the base preceding the position of the error in base-calling (53 out of 54 errors for the fragment presented in FIG. 5), but also, equally reliably, by a consistent, steep Q-value decrease along the read (FIG. 5).

As shown in FIG. 5 we calculated a cumulative Q-value for 104 reads of 130 bp length that aligned to positions 48308 to 48405 (SEQ ID NO:01) of the forward strand in the genome of *Escherichia coli* strain K-12, substrain MG1655. Only the 98 bp part common to all these reads is shown. Each read represents a separate polony in the Illumina flow-cell, so the fluorescence intensities of the reads were measured independently. The Figure shows a sudden decrease in the reads quality, with all the reads having lower Q-values at the site base errors without however same genomic site. There is a corresponding increase in base-calling errors, without, however, any decrease in the overall fluorescence intensity. The interpretation of such a pattern is that at this position the Bst polymerase performs significantly incomplete nucleotide incorporation during one sequencing cycle. From this point on, the synthesis of individual DNA strands loses synchrony, resulting in a mixed signal from several positions during each cycle. The loss of synchrony is partial so the correct signal is still present, with large fluctuations in the Q-value per position. While the presence of such a phasing problem can be recognized, the Illumina Q-values in these parts of the reads are not trustworthy. At the same time, there is no impact on those parts of the reads that precede the problematic genomic position, nor on the reads aligned to the opposite strand. It is not easy to predict which sequence will generate such a problem, although some known correlates of it are present: e.g. high GC-content, two GGC triplets and a borderline indication of secondary structure formation. All of this is not enough to reliably predict the formation of such a problem from the sequence alone. In the case presented in the Figure, we see a decrease in Q-values shortly after the second GGC triplet with no perturbations around the first GGC triplet.

The individual Q-values, even if they somewhat correlate with error frequency, are not adequate as quantitative estimates of error likelihood to be used in Bayesian reasoning, because they often are good enough for the read to be accepted. The consequences of this are serious when it comes to recognizing rare sequence variants, either mutations or polymorphisms. We take advantage of the reproducibility of the phasing effect to separate phasing errors from other errors that our Bayesian procedure handles very well. First, we mask all positions with a phasing problem, and, in another round of analysis, we correct those positions. In preliminary studies, we accepted a given position in the clonal cluster as a somatic mutation if the average Q-value of all reads in this position exceeded a threshold. Subsequently, we realized that the average decrease of the Q-value along the read is an excellent predictor of the phasing problem, which may generate false positives. We implement a more sophisticated filter to identify Q-value downward jumps in the aligned reads. When the average of Q-values exceeds a threshold, subsequent positions in the reads are filtered out in the first round of analysis. We can do it at the clonal cluster level or by mapping polymorphism control reads, discussed later, to obtain genomic averages of Q-value jumps and apply them to filter out the parts of reads with severe phasing problems. In the second part of the analysis, we adapt GATK Q-value recalibration to use the self-consistency of sequence information in the clonal cluster, rather than relying on the external information in the genomic assembly. In addition, using Bayesian reasoning, we differentiate between the chemical events that create correlated patterns in clonal clusters and the proper base-calling errors. Unlike the existing procedures, which lump all the effects together, our recalibrated base-calling Q-values only refer to the uncertainties generated by the processes inside the flow-cell, and not those created by the earlier preparation steps, which have their own probabilistic model. At this stage, we can assume that the majority of sequences have been properly analyzed so as not to have somatic mutations, and the evidence of somatic mutations in some others is strong enough not to be doubted. But there will be some intermediate cases, where we can better analyze the evidence by performing another layer of calculations, relying on the fluorescence intensities. The advantage of adding a second round of base-calling at a late stage is that the computationally intensive deconvolution of complex phasing patterns will be applied only to a small subset of data. We include here the previously filtered out parts of reads with severe phasing problems. Gathering the fluorescent intensities from multiple reads allows us to average the position-specific phasing delay estimate and to redo base-calling, using the averaged intensities and the averaged phasing delay estimate. Calculating averages are optimized by weighting the information from multiple reads, as each polony tends to have a somewhat different error level. Performing base-calling on averaged intensities follows a similar linear modeling of signal and an inversion of cross-talk equations as in the program TotalReCaller [74].

However, our calculations estimate base calling reliability by multi-component error modeling, rather than combinatorial decision-making as done in TotalReCaller. Other improvements to base-calling involve a better model of the imaging artifacts generated during the scan of fluorescent images. We have identified the following imaging problems affecting the Illumina read-out: focus variations, speckle pattern from laser illumination in the GA-II$_x$ model, occasional presence of dust obscuring the optical paths, a highly reproducible optical artifact at the edge of the flow-cell lane, and presence of "floaters", presumably from some kind of rolling circle amplification and illuminating light leakage. Each of them creates a characteristic spatial pattern that affects fluorescent intensities. Such patterns extend over thousands of polonies, so they can be modeled by local averaging procedures. Depending on the source of the problem, the procedure may involve the averaging of a multiplicative factor, of an additive factor or, in the case of focus variability, of a factor multiplying the uncertainty (error estimate). These signal processing improvements are significant not only for our TwinSeq protocol, but also for other applications of high throughput sequencing.

We can identify rare somatic mutations in the high background of other sequence changes, which results from the already discussed sequencing library preparation and base-calling errors, but also includes unidentified genomic polymorphisms and, potentially, artifacts of sequence reads alignment. The tests with mice tissue samples allow us to optimize data analysis for a genome with the same level of complexity as human. A somatic mutation is defined as a DNA sequence pattern that is not present in the zygotic DNA, from which the organism has developed. To establish that a candidate for a mutation was not present in the zygote an important factor is to differentiate between the polymorphisms present in the zygote and the somatic mutations generated later. The expected level of genomic polymorphisms is about 0.1%. Our goal of an error level of 1 per billion base pairs requires stringent criteria to avoid false positives resulting from polymorphisms, which are about a million times more frequent than our targeted error level. Mapping polymorphisms requires additional data, which we call polymorphism control reads, acquired from one or more tissue types. High sequencing reliability allows us to identify somatic mutations present only once in our data.

The data from the 1000 Genome Initiative indicate that there are still about 50,000 rare or private genomic polymorphisms existing in a particular individual that are absent from the database [73]. These rare polymorphism variants are normally present in only one copy, co-occurring with a reference allele present in the other chromosome. That means that if we observe a particular position in the genome N times, we have a chance of $2^{-N}$ of missing one allele by random selection from N possibilities. This criterion gives us a minimal genomic coverage of about 16 per a particular position in polymorphism control reads that is needed to accept a candidate for somatic mutation in the target reads. Additionally, we need to separately acquire about 30× coverage of a particular person's genome in the control reads to avoid losing efficiency to polymorphism rejection criteria. When analyzing a particular tissue, we can include target reads from other tissues as a contribution to polymorphisms controls, but they do not provide sufficient coverage by themselves.

We can adjust the coverage threshold if a particular position in the genome is a part of a Copy Number Variation (CNV) segment. To determine the copy number, we can use standard CNV calling methods [75]. Applying stringent criteria for rejecting potential false positive resulting from polymorphism and complex types of repetitive sequences still allows us to accept 65-80% of the data that passed sequencing error level criterion. Since we identify rare sequence events, the analysis is designed to avoid all potential sources of false positives. Unexpected false positives are generated by underestimating error probability, while overestimating is generally safe, except for potentially reducing the efficiency of the experiment. It is enough that we can identify troublesome data patterns, even without fully diagnosing them, as long as the data rejections do not significantly reduce the efficiency of the experiment.

At the end, we check for a possibility that residual approximation errors may create overconfidence in the mutation call estimates. The validation is based on the receiver-operating characteristic (ROC) curve analysis, to see if, by relaxing the confidence criteria the predicted level of signal increases as predicted by Bayesian reasoning. If the signal increases more than expected, it indicates that, due to approximations, the Bayesian reasoning is overconfident. For small values of such signal excess, the solution is simply to accept an overall correction factor to the log-confidence, by optimizing the factor to produce more appropriate increase of the signal as a function of confidence value. If the signal excess is worrisome, it is analyzed for the associated correlation patterns [76], in order to identify its source and create a remedy, either by modifying the experiment or by adjusting methods of the data analysis.

Another aspect of the invention maps somatic mutations in different human tissues obtained from several (8-12) deceased persons—at least 8 samples per organ or tissue type (bladder, blood, bone marrow, brain, heart, liver, lung, lymph node, intestinal lining, pancreas, prostate, skin—both exposed to and shielded from sun, stomach, and thyroid). For each tissue sample, will generate 0.5-1 Gbp of sequence data, satisfying a reliability criterion of error level below one per billion base pairs. Depending on the mutation rate, we observe tens to thousands of somatic mutations per sample.

The invention enables a whole range applications including single cell studies, as we need only 10% of DNA in a single cell to be digested into the size range suitable for sequencing, then to be ligated to adapters and transferred to the PCR buffer. A study of somatic mutations selected by the affinity methods is performed by two-step PCR and the affinity selection by DNA hybridization in between the PCR steps. An example of the affinity selection approach is to capture all chromosomal translocations that involve the genomic neighborhood of the myc gene during the somatic evolution of cancer.

FIG. 1. (A) The description of the preparation of the sequencing library in Twin-seq method in comparison to the standard Illumina library preparation. The fragmentation, the end-repair and the phosphorylation reactions will be replaced by the fragmentation using DFF40 nuclease. The ligated adapters will contain short multiplexing adapter, randomized at the ligation site. The arrows and circles represent the ends of the single-strand in the duplex to emphasize the polarity of the molecules. (B) The second important factor will be clonal-amplification introduced during selection of properly ligated fragments by PCR. Each dsDNA fragment with ligated Y adapters will create two distinct clonal clusters. The members of these clusters will attach to Illumina cell randomly, and those fragments that will attach will give rise to a separate polony each, i.e. will result in a separate sequencing reads. The analysis of sequence consensuses between the clonally-amplified and control (not amplified clonally) will follow, as described later and on the FIG. 3.

FIG. 2. The distribution and pattern of errors accumulated during the end-repair. The most probable chemistry and process that could generate them is presented inside the insert on the right.

FIG. 3. The hierarchy of sequencing consensuses between clonal clusters. Each effect will have its own signature with associated expected magnitude of the effect.

FIG. 4. The flowchart of our data analysis scheme.

FIG. 5. We calculated a cumulative Q-value for 104 reads of 130 bp length that aligned to positions 48308 to 48405 of the forward strand in the genome of *Escherichia coli* strain K-12, substrain MG1655. Only the 98 bp part common to all these reads is shown. Each read represents a separate polony in the Illumina flow-cell, so the fluorescence intensities of the reads were measured independently. The Figure shows a sudden decrease in the reads quality, with all the reads having lower Q-values at the same genomic site. There is a corresponding increase in base-calling errors, without, however, any decrease in the overall fluorescence intensity. The interpretation of such a pattern is that at this position the Bst polymerase performs significantly incomplete nucleotide incorporation during one sequencing cycle. From this point on, the synthesis of individual DNA strands loses synchrony, resulting in a mixed signal from several positions during each cycle. The loss of synchrony is partial so the correct signal is still present, with large fluctuations in the Q-value per position. While the presence of such a phasing problem can be recognized, the Illumina Q-values in these parts of the reads are not trustworthy. At the same time, there is no impact on those parts of the reads that precede the problematic genomic position, nor on the reads aligned to the opposite strand. It is not easy to predict which sequence will generate such a problem, although some known correlates of it are present: eg. high GC-content, two GGC triplets and a borderline indication of secondary structure formation. All of this is not enough to reliably predict the formation of such a problem from the sequence alone. In the case presented in the Figure, we see a decrease in Q-values shortly after the second GGC triplet (red underline) with no perturbations around the first GGC triplet (green underline).

There is a corresponding increase in base-calling errors, without, however, any decrease in the overall fluorescence intensity. While the presence of such a phasing problem can be recognized, the Illumina Q-values in these parts of the reads are not trustworthy. At the same time there is no impact on those parts of the reads that precede the problematic genomic position, nor on the reads aligned to the opposite strand. We studied 17 reads that had the highest total Q-value in this 98 bp region. The pattern of errors counted is highly non-random and the erroneous bases correspond to the basein the preceding position of the reference sequence. Positions with multiple errors correlate better with the drop in the Q-value rather than the Q-value itself.

Another aspect of the invention maps somatic mutations in different human tissues obtained from several (8-12) deceased persons—at least 8 samples per organ or tissue type (bladder, blood, bone marrow, brain, heart, liver, lung, lymph node, intestinal lining, pancreas, prostate, skin—both exposed to and shielded from sun, stomach, and thyroid). For each tissue sample, we generate 0.5-1 Gbp of sequence data, satisfying a reliability criterion of error level below one per billion base pairs. Depending on the mutation rate, we observe tens to thousands of somatic mutations per sample.

1. Liu, M. & D. G. Schatz, *Balancing AID and DNA repair during somatic hypermutation*. Trends Immunol, 2009. 30: p. 173-81.
2. Odegard, V. H. & D. G. Schatz, *Targeting of somatic hypermutation*. Nat Rev Immunol, 2006. 6: p. 573-83.
3. Goodnow, C. C., *Balancing immunity and tolerance: deleting and tuning lymphocyte repertoires*. Proc Natl Acad Sci USA, 1996. 93: p. 2264-71.
4. Failla, G., *The aging process and cancerogenesis*. Ann N Y Acad Sci, 1958. 71: p. 1124-40.
5. Szilard, L., *On the Nature of the Aging Process*. Proc Natl Acad Sci USA, 1959. 45: p. 30-45.
6. Vijg, J. & M. E. Dolle, *Large genome rearrangements as a primary cause of aging*. Mech Ageing Dev, 2002. 123: p. 907-15.
7. Gensler, H. L. & H. Bernstein, *DNA damage as the primary cause of aging*. Q Rev Biol, 1981. 56: p. 279-303.
8. Hoeijmakers, J. H., *DNA damage, aging, and cancer*. N Engl J Med, 2009. 361: p. 1475-85.
9. Loeb, L. A., *Mutator phenotype may be required for multistage carcinogenesis*. Cancer Res, 1991. 51: p. 3075-9.
10. Perucho, M., *Cancer of the microsatellite mutator phenotype*. Biol Chem, 1996. 377: p. 675-84.
11. Little, M. P., *Cancer models, genomic instability and somatic cellular Darwinian evolution*. Biol Direct, 2010. 5: p. 19; discussion 19.
12. Leung, D. W., et al., *Structural basis for dsRNA recognition and interferon antagonism by Ebola VP35*. Nat Struct Mol Biol, 2010. 17: p. 165-72.
13. Rezacova, P., et al., *Crystal structures of the effector-binding domain of repressor Central glycolytic gene Regulator from Bacillus subtilis reveal ligand-induced* structural changes upon binding of several glycolytic intermediates. Mol Microbiol, 2008. 69: p. 895-910.
14. Rezacova, P., et al., *The crystal structure of the effector-binding domain of the trehalose repressor TreR from Bacillus subtilis 168 reveals a unique quarternary assembly.* Proteins, 2007. 69: p. 679-82.
15. Luisi, B. F., et al., *Crystallographic analysis of the interaction of the glucocorticoid receptor with DNA.* Nature, 1991. 352: p. 497-505.
16. Otwinowski, Z., et al., *Crystal structure of trp repressor/operator complex at atomic resolution.* Nature, 1988. 335: p. 321-9.
17. Lawson, C. L., et al., *Flexibility of the DNA-binding domains of trp repressor.* Proteins, 1988. 3: p. 18-31.
18. Schevitz, R. W., Z. Otwinowski, A. Joachimiak, C. L. Lawson, & P. B. Sigler, *The three-dimensional structure of trp repressor.* Nature, 1985. 317: p. 782-6.
19. Borek, D. & Z. Otwinowski, *Kinetic control of eukaryotic chromatin structure by recursive topological restraints.* Nature Precedings, 2008. http://hdl.handle.net/10101/npre.2008s2672.1: p.
20. Borek, D., M. Cymborowski, M. Machius, W. Minor, & Z. Otwinowski, *Diffraction data analysis in the presence of radiation damage.* Acta Crystallogr D Biol Crystallogr, 2010. 66: p. 426-36.
21. Borek, D., S. L. Ginell, M. Cymborowski, W. Minor, & Z. Otwinowski, *The many faces of radiation-induced changes.* J Synchrotron Radiat, 2007. 14: p. 24-33.
22. Borek, D., W. Minor, & Z. Otwinowski, *Measurement errors and their consequences in protein crystallography.* Acta Crystallogr D Biol Crystallogr, 2003. 59: p. 2031-8.
23. Otwinowski, Z. *Maximum likelihood refinement of heavy atom parameters.* in CCP4 Study Weekend. 1991: Science and Engineering Research Council.
24. Otwinowski, Z. & W. Minor, *Processing of X-ray Diffraction Data Collected in Oscillation Mode.* Methods Enzymol, 1997. 276: p. 307-326.
25. Rowicka, M., A. S. Kudlicki, B. P. Tu, & Z. Otwinowski, *High-resolution Timing of the Cell-Cycle Events.* Molecular Biology of the Cell, 2006. 17: p. -.
26. Otwinowski, Z., D. Borek, W. Majewski, & W. Minor, *Multiparametric scaling of diffraction intensities.* Acta Crystallographica Section A, 2003. 59: p. 228-34.
27. Gundry, M., W. Li, S. B. Maqbool, & J. Vijg, *Direct, genome-wide assessment of DNA mutations in single cells.* Nucleic Acids Res, 2011.
28. Gundry, M. & J. Vijg, *Direct mutation analysis by high-throughput sequencing: From germline to low-abundant, somatic variants.* Mutat Res, 2011.
29. Da Sylva, T. R., C. S. Gordon, & G. E. Wu, *A genetic approach to quantifying human in vivo mutation frequency uncovers transcription level effects.* Mutat Res, 2009. 670: p. 68-73.
30. Kinde, I., J. Wu, N. Papadopoulos, K. W. Kinzler, & B. Vogelstein, *Detection and quantification of rare mutations with massively parallel sequencing.* Proc Natl Acad Sci USA, 2011. 108: p. 9530-5.
31. Loeb, L. A., *Human cancers express mutator phenotypes: origin, consequences and targeting.* Nat Rev Cancer, 2011. 11: p. 450-7.
32. Gollob, M. H., et al., *Somatic mutations in the connexin 40 gene (GJA5) in atrial fibrillation.* N Engl J Med, 2006. 354: p. 2677-88.
33. Goodnow, C. C., *Multistep pathogenesis of autoimmune disease.* Cell, 2007. 130: p. 25-35.
34. Erickson, R. P., *Somatic gene mutation and human disease other than cancer: an update.* Mutat Res, 2010. 705: p. 96-106.
35. Li, W. & J. Vijg, *Measuring Genome Instability in Aging.* Gerontology, 2011.
36. Kennedy, S. R., L. A. Loeb, & A. J. Herr, *Somatic mutations in aging, cancer and neurodegeneration.* Mech Ageing Dev, 2011.
37. Loeb, L. A., *Mutator phenotype in cancer: origin and consequences.* Semin Cancer Biol, 2010. 20: p. 279-80.
38. Crow, J. F., *The origins, patterns and implications of human spontaneous mutation.* Nat Rev Genet, 2000. 1: p. 40-7.
39. Dolle, M. E., W. K. Snyder, J. A. Gossen, P. H. Lohman, & J. Vijg, *Distinct spectra of somatic mutations accumulated with age in mouse heart and small intestine.* Proc Natl Acad Sci USA, 2000. 97: p. 8403-8.
40. Dolle, M. E., W. K. Snyder, D. B. Dunson, & J. Vijg, *Mutational fingerprints of aging.* Nucleic Acids Res, 2002. 30: p. 545-9.
41. Salk, J. J., E. J. Fox, & L. A. Loeb, *Mutational heterogeneity in human cancers: origin and consequences.* Annu Rev Pathol, 2010. 5: p. 51-75.
42. Gottlieb, B., L. K. Beitel, C. Alvarado, & M. A. Trifiro, *Selection and mutation in the "new" genetics: an emerging hypothesis.* Hum Genet, 2010. 127: p. 491-501.
43. Kondrashov, F. A. & A. S. Kondrashov, *Measurements of spontaneous rates of mutations in the recent past and the near future.* Philos Trans R Soc Lond B Biol Sci, 2010. 365: p. 1169-76.
44. Lynch, M., *The origins of eukaryotic gene structure.* Mol Biol Evol, 2006. 23: p. 450-68.
45. Cadet, J., T. Douki, D. Gasparutto, & J. L. Ravanat, *Oxidative damage to DNA: formation, measurement and biochemical features.* Mutat Res, 2003. 531: p. 5-23.
46. Kregel, K. C. & H. J. Zhang, *An integrated view of oxidative stress in aging: basic mechanisms, functional effects, and pathological considerations.* Am J Physiol Regul Integr Comp Physiol, 2007. 292: p. R18-36.
47. Cooke, M. S., M. D. Evans, M. Dizdaroglu, & J. Lunec, *Oxidative DNA damage: mechanisms, mutation, and disease.* FASEB J, 2003. 17: p. 1195-214.
48. Chen, J. H., C. N. Hales, & S. E. Ozanne, *DNA damage, cellular senescence and organismal ageing: causal or correlative?* Nucleic Acids Res, 2007. 35: p. 7417-28.
49. Nowell, P. C., *The clonal evolution of tumor cell populations.* Science, 1976. 194: p. 23-8.
50. Vincent, M. D., *Cancer: beyond speciation.* Adv Cancer Res, 2011. 112: p. 283-350.
51. Frank, S. A. & M. A. Nowak, *Problems of somatic mutation and cancer.* Bioessays, 2004. 26: p. 291-9.
52. Coghlin, C. & G. I. Murray, *Current and emerging concepts in tumour metastasis.* J Pathol, 2010. 222: p. 1-15.
53. Bielas, J. H. & L. A. Loeb, *Quantification of random genomic mutations.* Nat Methods, 2005. 2: p. 285-90.
54. Stratton, M. R., *Exploring the genomes of cancer cells: progress and promise.* Science, 2011. 331: p. 1553-8.
55. Puente, X. S., et al., *Whole-genome sequencing identifies recurrent mutations in chronic lymphocytic leukaemia.* Nature, 2011. 475: p. 101-5.
56. Paabo, S., D. M. Irwin, & A. C. Wilson, *DNA damage promotes jumping between templates during enzymatic amplification.* J Biol Chem, 1990. 265: p. 4718-21.
57. Langmead, B., *Aligning short sequencing reads with Bowtie.* Curr Protoc Bioinformatics, 2010. Chapter 11: p. Unit 11 7.

58. Drake, J. W., *A constant rate of spontaneous mutation in DNA-based microbes.* Proc Natl Acad Sci USA, 1991. 88: p. 7160-4.
59. Lynch, M., *Evolution of the mutation rate.* Trends Genet, 2010. 26: p. 345-52.
60. Lynch, M., *Rate, molecular spectrum, and consequences of human mutation.* Proc Natl Acad Sci USA, 2010. 107: p. 961-8.
61. Widlak, P. & W. T. Garrard, *Discovery, regulation, and action of the major apoptotic nucleases DFF40/CAD and endonuclease G.* J Cell Biochem, 2005. 94: p. 1078-87.
62. Widlak, P. & W. T. Garrard, *Unique features of the apoptotic endonuclease DFF40/CAD relative to micrococcal nuclease as a structural probe for chromatin.* Biochem Cell Biol, 2006. 84: p. 405-10.
63. Widlak, P. & W. T. Garrard, *The apoptotic endonuclease DFF40/CAD is inhibited by RNA, heparin and other polyanions.* Apoptosis, 2006. 11: p. 1331-7.
64. U. S. patent 5, 298, *Bst DNA polymerase with proofreading 3'-5' exonuclease activity.* 2011.
65. Kulmala, S., A. Kulmala, T. AlaKleme, A. Hakanen, & K. Haapakka, *Intrinsic and 1-aminonaphthalene-4-sulfonate-specific extrinsic lyoluminescences of X-ray irradiated sodium chloride.* Analytica Chimica Acta, 1997. 340: p. 245-256.
66. Saran, M., W. Bors, & P. Lester, [2] *Pulse radiolysis for investigation of nitric oxide-related reactions, in Methods in Enzymology.* 1994, Academic Press. p. 20-34.
67. Hamilton, M. L., et al., *A reliable assessment of 8-oxo-2-deoxyguanosine levels in nuclear and mitochondrial DNA using the sodium iodide method to isolate DNA.* Nucleic Acids Res, 2001. 29: p. 2117-26.
68. Nakae, D., Y. Mizumoto, E. Kobayashi, O. Noguchi, & Y. Konishi, *Improved genomic/nuclear DNA extraction for 8-hydroxydeoxyguanosine analysis of small amounts of rat liver tissue.* Cancer Lett, 1995. 97: p. 233-9.
69. Shibutani, S., M. Takeshita, & A. P. Grollman, *Insertion of specific bases during DNA synthesis past the oxidation-damaged base 8-oxodG.* Nature, 1991. 349: p. 431-4.
70. Katafuchi, A. & T. Nohmi, *DNA polymerases involved in the incorporation of oxidized nucleotides into DNA: their efficiency and template base preference.* Mutat Res, 2010. 703: p. 24-31.
71. Bravo, H. C. & R. A. Irizarry, *Model-based quality assessment and base-calling for second-generation sequencing data.* Biometrics, 2010. 66: p. 665-74.
72. McKenna, A., et al., *The Genome Analysis Toolkit: a MapReduce framework for analyzing next-generation DNA sequencing data.* Genome Res, 2010. 20: p. 1297-303.
73. The 1000 Genomes Project Consortium, A., *A map of human genome variation from population-scale sequencing.* Nature, 2010. 467: p. 1061-73.
74. Menges, F., G. Narzisi, & B. Mishra, *TotalReCaller: improved accuracy and performance via integrated alignment and base-calling.* Bioinformatics, 2011. 27: p. 2330-7.
75. Stamoulis, C. & R. A. Betensky, *A novel signal processing approach for the detection of copy number variations in the human genome.* Bioinformatics, 2011. 27: p. 2338-45.
76. Reshef, D. N., et al., *Detecting novel associations in large data sets.* Science, 2011. 334: p. 1518-24.
77. Conrad, D. F., et al., *Variation in genome-wide mutation rates within and between human families.* Nat Genet, 2011. 43: p. 712-4.

Example 2. HHMI Grant: Twin-Seq: A Method for Ultrahigh Accuracy in Next-Generation Sequencing and its Application to Single-Nucleotide and Somatic Mutations in Mammals Overview:

The revolution in genetics and genomics has enabled the study of biological systems and their potential translation to medicine with an unprecedented scale over the last two decades[1]. The determination of whole-genome sequences for model organisms and humans as well as the exploration of sequence diversity and ancestry has transformed our understanding of living systems. Recently with the advent of massively parallel "next-generation" sequencing (NGS) technologies[2-4], our ability to obtain sequence at the genome level rapidly and at lower cost has enabled individual laboratories to access information that was previously only within the purview of genome centers. Notwithstanding this remarkable progress, a critical issue plagues existing NGS technologies for which solutions have been elusive—while sequence volume has scaled exponentially in the last two decades, virtually no improvements have been made in the accuracy of sequencing. In this proposal, we describe a new method applied to NGS that increases the accuracy of sequencing by more than three orders of magnitude. The method, named "Twin-seq," was developed by two collaborating investigators, Dominika Borek and Zbyszek Otwinowski, who undertook a comprehensive analysis of the chemical and instrumental effects leading to errors and then designed strategies that effectively deal with each important source of errors. A core aspect of Twin-seq is to obtain fully independent information from two strands of a single DNA fragment by preserving strand information during library construction. Since the reads from the two strands can be made independent in their errors, this method reduces the error rate by several orders of magnitude. Additional accuracy gains come from an improved base calling procedure rooted in statistically sound likelihood methods and from a more rigorous analysis of copy number variation. Together this allows for extensive validation of all assumptions about the quality of sequencing. As a result, the joint reliability of sequence information obtained from a single DNA fragment can be better than one per billion base pair error rate. The Twin-seq concept is general enough to be extended to other platforms, such as the Ion Proton and other technologies using long sequencing reads.

Rationale:

Next-generation sequencing has enabled forward genetic studies recently[1]; however, the identification of mutations in a priori unknown genomic positions, solely from NGS data, remains a challenge. The primary limitation is the occurrence of sequencing errors, which affects all downstream analyses and results in numerous false positives. Therefore, the use of NGS in forward genetic studies still relies on genetic mapping to narrow candidate regions or recessive mutations that can be discerned more easily. Point mutations, which make up 56% of human mutations, remain troublesome, especially heterozygous dominant mutations, and require exhaustive and expensive validation to discriminate mutant loci from false positives.

We dramatically change this state by integrating expertise in mammalian forward genetics, advanced methods of evolutionary analysis, and significant improvements in the accuracy of NGS that lead to the sequencing error level below $10^{-9}$ per DNA base pair. As a result of our work, positional cloning becomes unnecessary and even small pedigrees will be sufficient to link mutations with a specific phenotype or disease.

To facilitate this work, we have developed a novel, highly efficient NGS sequencing approach, called Twin-seq, which unambiguously identifies even rare mutations in the background of experimental errors. A breakthrough aspect of our approach is a change in the experimental protocol that results in the generation of fully independent sequencing information for each of the two complementary strands of a particular dsDNA fragment in a sequencing library. We clonally amplify each of the fragments in the library. Then, in the data analysis, we increase the reliability by combining the multiple reads generated by clonal amplification, and perform the calls to identify changes in the DNA sequence. In the second step of the analysis, we compare consensus sequences obtained independently from the two complementary strands present in the original DNA fragment. This design results in well-defined statistical independence between groups of sequencing reads, with a robust, safe and efficient estimation of data reliability. The hierarchy of analysis differentiates mutations from other phenomena, such as: single nucleotide polymorphisms, changes introduced during DNA sample processing, pre-mutational changes such as in vivo chemical damage to DNA bases, and base-calling errors. Pilot experiments, in which we achieved an error level of $3 \cdot 10^{-8}$ per DNA base pair without any optimization, fully confirmed the power of the method and let us identify several sources of systematic effects, which when corrected should result in an error level of $10^{-9}$ per DNA base pair.

Not only do we increase the reliability of the results by introducing clonal amplification, but we also identify, classify, and either correct experimentally or model statistically the sources of errors in sequencing. Undetected sequencing errors can mimic mutations and result in false positives. There are other approaches to sequencing that either proposed or tried to implement[5-7] selected advancements that are used in Twin-seq in an integrated fashion. However, none of these approaches resulted in the error levels achieved in our preliminary studies, because the information from two strands of DNA duplex could not be differentiated in their experimental design. Additionally, the correlated base-calling errors were not considered as a source of the false positives. So far, other methods of calling mutations rely on either ad hoc statistical criteria or model errors indirectly. Indirect modeling, even if multifactorial, like in GATK[8,9], does not capture of full complexity of phasing errors generated by secondary structure in single-stranded DNA. Therefore, they are prone either to missing mutations when used with stringent parameters or to generating large numbers of false positive calls when set to a more relaxed mode. In theory, increasing the number of sequencing reads to improve the genomic coverage could alleviate these problems. However, this works well only if the errors are uncorrelated or weakly correlated. The general experience[10] as well as our preliminary studies all indicate that this is not the case—the correlated errors happen frequently in sequencing, particularly in certain genomic regions. Describing and modeling error sources directly let us separate problems introduced during sequencing library preparation from the effects generated later during sequencing by ligation, and from biological noise introduced by passenger mutations, unmapped SNPs, and various effects caused by genomic instabilities. We apply methods of signal processing to further improve the quality of sequencing data, and to separate the effects of so-called phasing errors introduced during sequencing by synthesis, from other instrumental problems.

The scalability and reliability of Twin-seq allows for studying mammalian genomes with forward genetics methods in a very efficient way to obtain data for tens of genomes in the case of full genome sequencing and hundreds of genomes in the case of exome sequencing.

Functional annotation of the mouse and human genomes remains one of the most difficult problems in genetics and genomics. The effective methods for discovery and functional identification of novel genes that underlie phenotypes are traditionally based on forward genetics, in which the meiotic mapping methods of positional cloning are used to locate mutant loci. Although hundreds of genes have been discovered and characterized in this way, it is often impossible to identify precisely the mutant locus, due to either insufficient statistical power or phenotypic ambiguity. In these cases, the candidate regions can be extremely large—typically in the 30-50 MB range, and until now such large genomic regions have been too costly to analyze using brute force methods such as sequencing of all candidate genes.

Twin-Seq is a tool that can also be used to advance forward genetic studies in mammalian cell culture. Using forward genetics in a mammalian cell culture system has been technically challenging and is fundamentally limited by our ability to efficiently discover mutations. Unlike other model systems, in mammalian cell culture there are no mechanisms to positional clone or narrow a gene locus through recombination events. Highly accurate Twin-seq bridges mammalian cell culture with classical genetics and in so doing provides a tool for gene and pathway discovery across many biological disciplines. The base-calling at the level of PCR clonal clusters, which we use in Twin-seq, allows for determination of mutations even in copy amplified genes. Such mutations are of high interest, because they may cause the resistance to anticancer therapy, e.g. a single mutation in one of the 20 copies of gene coding for EGFR receptor in lung cancer cells, which makes these cells resistant to Erlotinib, a potent anticancer medication. We combine Twin-Seq and forward genetics to identify the targets of novel chemical compounds that are selectively toxic to lung cancer cells. Our methods transform the massive scale generated by new sequencing technologies into high confidence in biological conclusions.

Results

The Twin-seq method determines mutations directly by sequencing DNA fragments with a reliability level of a single error per $10^9$ of DNA base pairs. To achieve such reliability, we need a much higher level of confidence than that generated by a single sequencing read. Therefore, we increase the confidence by combining information from two groups of sequencing reads that originated from complementary strands of a single DNA fragment. The design of the Illumina Y-adapters, in combination with opposite polarities of complementary DNA strands, results in a ligation product with built-in asymmetry. As a result, the polarity of a DNA strand serving as a template in PCR amplification can be unambiguously determined from a sequencing read. To control for errors introduced during the library preparation, we restrict the amount of starting template used in the PCR amplification employed in the standard Illumina protocol to select for dsDNA fragments with properly ligated adapters. This results in clonal amplification of each library fragment. During the very first PCR cycle, the asymmetric ligation product is denatured and the subsequent fates of the separated DNA strands, together with their amplified products, are independent from each other with respect to the potential introduction of errors. Each dsDNA fragment results after sequencing in two identifiable groups of paired-end reads. Each identified group originates from a single DNA strand with defined polarity, so we also observe the groups that correspond to their complements. An essence of the method is to use all these features to generate a hierarchy of consensuses between the sequencing reads and use those consensuses as validation criteria in statistical data analysis to identify mutations with high certainty and differentiate them with high confidence from other effects.

We identified four well-defined groups of effects leading to correlated errors in the sequencing reads: (1) when a polony (clonal cluster) on the surface of the flow-cell is split into two or more sequence reads by the Illumina software; (2) when errors are introduced during PCR amplification; (3) when DNA is chemically damaged prior to the PCR step. Such PCR- or chemically-induced errors have an expected frequency of less than $10^{-5}$; hence, the frequency of their coincidentally being on both strands in the same place will be $10^{-10}$, which is an acceptable level for our goals. The fourth source of correlated errors can mimic mutations. This correlated error arises from the repair of DNA fragmented by sonication or nebulization using a T4 DNA polymerase. The overhang sequence, used as a template, may contain a chemically altered base, e.g. 8-oxo-dG and the polymerase will insert with some frequency an incorrect nucleotide into the complementary strand. The damaged base may also induce the same mispairing later during PCR amplification. Consequently, the same chemical event causes a coupled sequencing error that appears in the same position, in two groups of reads corresponding to two complementary strands. In our preliminary studies, these repair effects manifest themselves as a surplus of coupled errors in both strands, concentrated close to the ligation site of sequencing adapters. After removing all these correlated errors, we observed in wt MG1655 E. coli, a single coupled change in 31,000,000 sequenced positions, which was consistent with our expectation of ~0.7 mutations.

We have also developed methods to minimize the level of errors introduced into the DNA during all steps of the sequencing process. We eliminate troublesome for Twin-seq DNA repair reaction entirely by fragmenting the DNA with double-strand-specific, apoptotic DNA endonuclease DFF40, which has been thoroughly characterized and produces blunt ends with a 5' phosphate extension[63-65]. We found PCR reactions a tolerably small contributor to sequencing errors. However, we identified the chemical damage existing prior to the PCR step to be a much larger contributor. We add NaI and $NaNO_3$ to mitigate the problem. We found both to be effective in scavenging hydrated electrons and hydroxyl radicals in our previous experiments[47,66-68]. The NaI was used in procedures minimizing the oxidative damage to guanidine, although without invoking the scavenger justification[69,70].

In the Twin-seq approach, almost every DNA fragment that enters clonal amplification by PCR is subsequently sequenced. We employ this feature to use microfluidic devices to generate sequencing libraries with a minimal amount of starting material and consumables. Additional sequencing reactions are performed in a targeted manner to achieve coverage sufficient to discover mutations in all regions. While sequencing was performed mainly on the Illumina Hi-Seq 2500 platform, the protocols and the method readily deployable with other platforms.

Polony identification, fluorescence signal estimation, and the first round of base-calling are performed with standard Illumina software. After quality filtering, we cluster sequences and analyze their consistency to identify the sources of disagreements. A singular value decomposition (SVD) analysis differentiates random events from potential systematic differences within the cluster. These differences are classified on the basis of correlations within the cluster as either arising from similar sequences within the genome (coincidences and/or polymorphisms) or from correlated sources of error, e.g. from chemical damage or PCR amplification. To enable optimal statistical (Bayesian) reasoning, we explicitly model the events that can generate errors in clonal clusters. Then we recalibrate the uncertainty estimates of the reads to include information about self-consistency between sequencing reads. In Illumina, the majority of sequencing errors is introduced during sequencing by synthesis and the interpretation of the associated fluorescent read-out. The sequencing by synthesis is a highly synchronized process, but occasionally the polymerase used in the process advances by two bases (pre-phasing) or fails to advance (phasing). We observed a reproducible, very pronounced strand-specific increase in the error level at particular genomic positions. The reliability index for a base call (Q-value), even if it correlates with error frequency, is not adequate as quantitative estimates of error likelihood in such case. Q-score recalibrations procedures, such as GATK[8,9] have been implemented, resulting in $10^{-6}$ level of false positives in SNP calls[71]. However, even with this improvement, the existing approaches[72] capture only part of the problem A more comprehensive solution to this problem is an important part of our invention.

The base-calling inefficiencies are at the core of the current problem with mutation calling, particularly when searching for mutations in a background arising from multiple homologous chromosomes typical for aneuploid cancer cells. A breakthrough aspect of the Twin-seq method is relying on full consistency of base-calls in a given position of the read within a clonal cluster. Without clonal amplification, we apply statistical criteria of how often a mutation is present in multiple reads overlapping at the same genomic position. In case of a polyploid genome, the signal for mutations appears with low frequency and it will be difficult to differentiate it from correlated base-calling errors. Additionally, we implement filtering that uses the average decrease of the Q-value along the aligned sequences as the predictor of the phasing problem. First, we mask positions with predicted phasing problems in all sequencing data. Then, if the average of the measured Q-values exceeds a threshold in the masked sequencing reads, subsequent positions in the affected reads are removed from analysis. At this point, we perform a second round of base calling on previously filtered out parts of reads with severe phasing problems. We average the fluorescent intensities from multiple reads mapping to the same genomic region to estimate the position-specific phasing delay and to redo base-calling. Performing base-calling on averaged intensities applies a combination of linear modeling of the signal, an inversion of cross-talk equations, and estimation of the base calling reliability by multi-component error modeling. Other improvements to base-calling involve a better model of the imaging artifacts generated during the scan of fluorescent images.

In data analysis we often seek to differentiate between three hypotheses: genomic polymorphism at the source, non-clonal mutations, and the desired mutations. To achieve this differentiation, we sequence with appropriate coverage the reference genome and the studied mutated samples without clonal amplification. The likelihoods of the three hypotheses depend on agreement between the sequencing reads and mutations called by the Twin-seq methods. Our calculations are adjusted to correct for a number of chromosomes or more generally for Copy Number Variation (CNV). We have developed a novel procedure that applies exponential modeling to account for an uneven frequency of reads due to experimental biases[73,74], and then follows it by CNV calling. Results of exponential modeling are also used to interpret sources of biases in the library preparation, and additionally as an input for design counter-biasing strategies.

Lastly, we check for the possibility that residual approximation errors may create overconfidence in the mutation call estimates. We check if by relaxing the confidence criteria, the predicted level of signal increases as predicted by Bayesian reasoning. If the signal increases more than expected, it indicates that due to approximations, the Bayesian reasoning is overconfident. If the signal excess is worrisome, it can be analyzed for the associated correlation patterns[75], in order to identify its source and create a remedy.

The output from the mutation calling procedures will be analyzed by multi-level filtering to differentiate the mutations driving the phenotypes from passenger mutations that will be present in the samples.

Application of Twin-seq to Mouse Mutants. As a proof of principle for applying Twin-Seq to a mammalian genome, we first use ENU-induced mouse mutants on an isogenic C57BL/6J genetic background because of the substantially reduced sequence polymorphism rates in inbred mouse strains. It has been estimated that the total mutation rate for ENU including silent mutations is about 1 base pair per 100,000 base pairs of coding sequence[76]. However, the overt (i.e., causative) ENU-induced mutation rate is about 1 base pair change in a million base pairs of coding sequence. As an initial test case, we resequence the genome of the mouse Clock mutant in which a single point mutation in the splice donor site of exon 19 was the causative mutation[16]. This region of the mouse genome is an ideal case because we previously sequenced a 200 kb interval containing the Clock locus[77] (as well as resequenced a 50 Mb targeted genomic interval containing the Clock mutation and recovered the mutation using a custom NimbleGen array followed by Roche FLX 454 sequencing.

We also apply Twin-Seq to the discovery new ENU mutants in the mouse that we have isolated and mapped for circadian behavior, fear conditioning and psychostimulant response, but have not identified the gene. Using current Applied Biosystems SOLiD NGS whole-genome sequencing, we had not been able to identify single-nucleotide mutations efficiently or reliably because of the significant sequencing error rate. We had a cohort of about 10 circadian mutants, 6 fear conditioning mutants and 12 psychostimulant response mutants as well as 5 body weight mutants and 10 diabetes mutants in which the causative gene remained to be identified. Many of these mutants can be and have been mapped to a chromosome, but high-resolution mapping will be very time- and resource-intensive. Our ability to rapidly clone these mutations without having to generate high resolution mapping crosses transforms our ability to do forward genetics in the mouse. Although alternative mouse mutant resources to produce null mutations in all genes of the mouse in ES cells are under way (the Knockout Mouse Project)[78,79], it is already known that null mutations alone are not adequate to test the function of the majority of genes because of lethality or overlapping and compensatory effects of paralogous genes. Indeed, the majority of human disease mutations are point mutations that cause a wide array of missense, gain-of-function, or partial loss-of-function alleles that reveal overt phenotypes not seen in null alleles. For example, from a total of 120,004 human mutations in 4,411 genes, 56% are caused by single-nucleotide changes. Thus, ENU mutagenesis provides a complementary approach to null alleles in providing a diversity of mutant alleles. Low resolution genetic mapping and Twin-seq whole-genome sequence at 20-30× coverage reveals the identity of these new mutations and serves as a stringent test of Twin-seq technology for the discovery of point mutations in the mouse genome.

Identification of Targets of Chemical Compounds that have Selective Toxicity to Lung Cancer Cells.

Recent advances in lung cancer treatment have led to a reclassification of the disease into subtypes based on a phenotypic response to new therapies[80-82]. This prompted John Minna and Steve McKnight to perform a chemical compound phenotypic screen of 12 genetically diverse lung cancer cell lines to identify compounds that are selectively toxic to at least one but not all cell lines.

An immortalized bronchial epithelial cell and each cancer cell line were screened for proliferation after treatment with one of 220,500 chemical compounds. 298 compounds inhibited the proliferation of at least one but not all the cancer cell lines. 83 chemicals representing multiple chemotypes inhibit proliferation by 50% at a concentration ($IC_{50}$) at least 100 fold lower than the other cell lines. The selective toxicity of these compounds is comparable to Erlotinib and Crizotnib, two clinically successful targeted therapies for the treatment of lung cancer[80-82]. Therefore, identifying the targets for and mechanism of action of these novel compounds has the potential to improve clinical outcomes. After confirming that differential toxicity is not a function of chemical metabolism, we identify these targets by combining forward genetics and Twin-Seq in lung cancer cell culture.

We select for clonal resistance amongst a population of sensitive cells that have undergone random mutagenesis and then use Twin-Seq to discover the mutation that confers resistance. To minimize high background mutation rates, we choose the lowest concentration of chemical mutagen that gives rise to clonal resistance. Furthermore, since we are selecting for a gain of function mutation that may be confined to only a few base pair changes, we initially screen $5 \times 10^8$ cells conservatively requiring that only one mutation in the human exome be mutated per cell. Clones that have nonspecific resistance as determined by cross-resistance to Paclitaxel, Etoposide, or Doxorubicin are removed.

Two specific challenges to identifying a mutation that confers resistance are a high background mutation rate and gene amplification. Cancer genome sequencing efforts have revealed heterogeneous and high rates of mutations[83-87]. Moreover, as a result of random mutagenesis resistant cells are expected to have additional background mutations irrelevant to the resistance phenotype. Furthermore, gene amplification is a frequent event in lung cancer particularly for oncogenes and mutations[88,89] that confer resistance may only occur in one allele and so will require Twin-Seq that is capable of unambiguously identifying mutations in the context of allelic dilution. We validate genes that are independently mutated in multiple clones by testing for de novo resistance after expression of the gene carrying the identified mutation. Finally, we confirm that the wild type but not mutant form has biochemical affinity for the compound. Twin-Seq is required to discover a single base pair mutation in the context of a high background rate and allelic dilution. Once identified, target identification is confirmed by both genetic and biochemical assays.

The combination of Twin-Seq and mammalian cell culture genetics provides a direct path to target identification of recently identified chemical compounds that selectively affect lung cancer cells.

BIBLIOGRAPHY

1. Gonzaga-Jauregui, C., J. R. Lupski, & R. A. Gibbs, *Human genome sequencing in health and disease*. Annu Rev Med, 2012. 63: p. 35-61.
2. Mardis, E. R., *The impact of next-generation sequencing technology on genetics*. Trends Genet, 2008. 24: p. 133-41.
3. Metzker, M. L., *Sequencing technologies—the next generation*. Nat Rev Genet, 2010. 11: p. 31-46.
4. Bentley, D. R., et al., *Accurate whole human genome sequencing using reversible terminator chemistry*. Nature, 2008. 456: p. 53-9.
5. Kinde, I., J. Wu, N. Papadopoulos, K. W. Kinzler, & B. Vogelstein, *Detection and quantification of rare mutations with massively parallel sequencing*. Proc Natl Acad Sci USA, 2011. 108: p. 9530-5.
6. Gundry, M., W. Li, S. B. Maqbool, & J. Vijg, *Direct, genome-wide assessment of DNA mutations in single cells*. Nucleic Acids Res, 2011.
7. Gundry, M. & J. Vijg, *Direct mutation analysis by high-throughput sequencing: From germline to low-abundant, somatic variants*. Mutat Res, 2011.
8. DePristo, M. A., E. Banks, R. Poplin, K. V. Garimella, J. R. Maguire, C. Hartl, A. A. Philippakis, G. del Angel, M. A. Rivas, M. Hanna, A. McKenna, T. J. Fennell, A. M. Kernytsky, A. Y. Sivachenko, K. Cibulskis, S. B. Gabriel, D. Altshuler, & M. J. Daly, *A framework for variation discovery and genotyping using next-generation DNA sequencing data*. Nat Genet, 2011. 43: p. 491-8.
9. McKenna, A., M. Hanna, E. Banks, A. Sivachenko, K. Cibulskis, A. Kernytsky, K. Garimella, D. Altshuler, S. Gabriel, M. Daly, & M. A. DePristo, *The Genome Analysis Toolkit: a MapReduce framework for analyzing next-generation DNA sequencing data*. Genome Res, 2010. 20: p. 1297-303.
10. Bravo, H. C. & R. A. Irizarry, *Model-based quality assessment and base-calling for second-generation sequencing data*. Biometrics, 2010. 66: p. 665-74.
11. Engelman, J. A., T. Mukohara, K. Zejnullahu, E. Lifshits, A. M. Borras, C. M. Gale, G. N. Naumov, B. Y. Yeap, E. Jarrell, J. Sun, S. Tracy, X. Zhao, J. V. Heymach, B. E. Johnson, L. C. Cantley, & P. A. Janne, *Allelic dilution obscures detection of a biologically significant resistance mutation in EGFR-amplified lung cancer*. J Clin Invest, 2006. 116: p. 2695-706.
12. Takahashi, J. S., L. H. Pinto, & M. H. Vitaterna, *Forward and reverse genetic approaches to behavior in the mouse*. Science, 1994. 264: p. 1724-33.
13. Vitaterna, M. H., D. P. King, A. M. Chang, J. M. Kornhauser, P. L. Lowrey, J. D. McDonald, W. F. Dove, L. H. Pinto, F. W. Turek, & J. S. Takahashi, *Mutagenesis and mapping of a mouse gene, Clock, essential for circadian behavior*. Science, 1994. 264: p. 719-25.
14. Antoch, M. P., E. J. Song, A. M. Chang, M. H. Vitaterna, Y. Zhao, L. D. Wilsbacher, A. M. Sangoram, D. P. King, L. H. Pinto, & J. S. Takahashi, *Functional identification of the mouse circadian Clock gene by transgenic BAC rescue*. Cell, 1997. 89: p. 655-67.
15. King, D. P., M. H. Vitaterna, A. M. Chang, W. F. Dove, L. H. Pinto, F. W. Turek, & J. S. Takahashi, *The mouse Clock mutation behaves as an antimorph and maps within the W19H deletion, distal of Kit*. Genetics, 1997. 146: p. 1049-60.
16. King, D. P., Y. Zhao, A. M. Sangoram, L. D. Wilsbacher, M. Tanaka, M. P. Antoch, T. D. Steeves, M. H. Vitaterna, J. M. Kornhauser, P. L. Lowrey, F. W. Turek, & Takahashi, *Positional cloning of the mouse circadian clock gene*. Cell, 1997. 89: p. 641-53.
17. Lawson, C. L., R. G. Zhang, R. W. Schevitz, Z. Otwinowski, A. Joachimiak, & P. B. Sigler, *Flexibility of the DNA-binding domains of trp repressor*. Proteins, 1988. 3: p. 18-31.
18. Leung, D. W., K. C. Prins, D. M. Borek, M. Farahbakhsh, J. M. Tufariello, P. Ramanan, J. C. Nix, L. A. Helgeson, Z. Otwinowski, R. B. Honzatko, C. F. Basler, & G. K. Amarasinghe, *Structural basis for dsRNA recognition and interferon antagonism by Ebola VP35*. Nat Struct Mol Biol, 2010. 17: p. 165-72.
19. Luisi, B. F., W. X. Xu, Z. Otwinowski, L. P. Freedman, K. R. Yamamoto, & P. B. Sigler, *Crystallographic analysis of the interaction of the glucocorticoid receptor with DNA*. Nature, 1991. 352: p. 497-505.
20. Otwinowski, Z., R. W. Schevitz, R. G. Zhang, C. L. Lawson, A. Joachimiak, R. Q. Marmorstein, B. F. Luisi, & P. B. Sigler, *Crystal structure of trp repressor/operator complex at atomic resolution*. Nature, 1988. 335: p. 321-9.
21. Rezacova, P., M. Kozisek, S. F. Moy, I. Sieglova, A. Joachimiak, M. Machius, & Z. Otwinowski, *Crystal structures of the effector-binding domain of repressor Central glycolytic gene Regulator from Bacillus subtilis reveal ligand-induced structural changes upon binding of several glycolytic intermediates*. Mol Microbiol, 2008. 69: p. 895-910.
22. Rezacova, P., V. Krejcirikova, D. Borek, S. F. Moy, A. Joachimiak, & Z. Otwinowski, *The crystal structure of the effector-binding domain of the trehalose repressor TreR from Bacillus subtilis 168 reveals a unique quarternary assembly*. Proteins, 2007. 69: p. 679-82.
23. Schevitz, R. W., Z. Otwinowski, A. Joachimiak, C. L. Lawson, & P. B. Sigler, *The three-dimensional structure of trp repressor*. Nature, 1985. 317: p. 782-6.
24. Borek, D., W. Minor, & Z. Otwinowski, *Measurement errors and their consequences in protein crystallography*. Acta Crystallogr D Biol Crystallogr, 2003. 59: p. 2031-8.
25. Otwinowski, Z. *Maximum likelihood refinement of heavy atom parameters*. in *CCP4 Study Weekend*. 1991: Science and Engineering Research Council.
26. Otwinowski, Z. & W. Minor, *Processing of X-ray Diffraction Data Collected in Oscillation Mode*. Methods Enzymol, 1997. 276: p. 307-326.
27. Rowicka, M., A. S. Kudlicki, B. P. Tu, & Z. Otwinowski, *High-resolution Timing of the Cell-Cycle Events*. Molecular Biology of the Cell, 2006. 17: p.
28. Otwinowski, Z., D. Borek, W. Majewski, & W. Minor, *Multiparametric scaling of diffraction intensities*. Acta Crystallographica Section A, 2003. 59: p. 228-34.
29. Kudlicki, A., M. Rowicka, M. Gilski, & Z. Otwinowski, *An efficient routine for computing symmetric real spherical harmonics for high orders of expansion*. Journal of Applied Crystallography, 2005. 38: p. 501-504.
30. Kudlicki, A., M. Rowicka, & Z. Otwinowski, *The crystallographic fast Fourier transform. Recursive symmetry reduction*. Acta Crystallographica Section A, 2007. 63: p. 465-480.

31. Kudlicki, A., M. Rowicka, & Z. Otwinowski, *SCEPTRANS: an online tool for analyzing periodic transcription in yeast*. Bioinformatics, 2007. 23: p. 1559-1561.
32. Rowicka, M., A. Kudlicki, B. P. Tu, & Z. Otwinowski, *High-resolution timing of cell cycle-regulated gene expression*. Proceedings of the National Academy of Sciences of the United States of America, 2007. 104: p. 16892-16897.
33. Chen, Z., D. Borek, S. B. Padrick, T. S. Gomez, Z. Metlagel, A. M. Ismail, J. Umetani, D. D. Billadeau, Z. Otwinowski, & M. K. Rosen, *Structure and control of the actin regulatory WAVE complex*. Nature, 2010. 468: p. 533-8.
34. Cigler, P., M. Kozisek, P. Rezacova, J. Brynda, Z. Otwinowski, J. Pokorna, J. Plesek, B. Gruner, L. Doleckova-Maresova, M. Masa, J. Sedlacek, J. Bodem, H. G. Krausslich, V. Kral, & J. Konvalinka, *From nonpeptide toward noncarbon protease inhibitors: metallacarboranes as specific and potent inhibitors of HIV protease*. Proc Natl Acad Sci USA, 2005. 102: p. 15394-9.
35. Kim, M. W., Y. Chelliah, S. W. Kim, Z. Otwinowski, & I. Bezprozvanny, *Secondary structure of Huntingtin amino-terminal region*. Structure, 2009. 17: p. 1205-12.
36. Korolev, S., I. Dementieva, R. Sanishvili, W. Minor, Z. Otwinowski, & A. Joachimiak, *Using surface-bound rubidium ions for protein phasing*. Acta Crystallogr D Biol Crystallogr, 2001. 57: p. 1008-12.
37. Li, A. Y., J. Lee, D. Borek, Z. Otwinowski, G. F. Tibbits, & M. Paetzel, *Crystal structure of cardiac troponin C regulatory domain in complex with cadmium and deoxycholic acid reveals novel conformation*. J Mol Biol, 2011. 413: p. 699-711.
38. Machius, M., C. A. Brautigam, D. R. Tomchick, P. Ward, Z. Otwinowski, J. S. Blevins, R. K. Deka, & M. V. Norgard, *Structural and biochemical basis for polyamine binding to the Tp0655 lipoprotein of Treponema pallidum: putative role for Tp0655 (TpPotD) as a polyamine receptor*. J Mol Biol, 2007. 373: p. 681-94.
39. Taylor, A. B., B. S. Smith, S. Kitada, K. Kojima, H. Miyaura, Z. Otwinowski, A. Ito, & J. Deisenhofer, *Crystal structures of mitochondrial processing peptidase reveal the mode for specific cleavage of import signal sequences*. Structure, 2001. 9: p. 615-25.
40. Walsh, M. A., Z. Otwinowski, A. Perrakis, P. M. Anderson, & A. Joachimiak, *Structure of cyanase reveals that a novel dimeric and decameric arrangement of subunits is required for formation of the enzyme active site*. Structure, 2000. 8: p. 505-14.
41. Yang, M., C. B. Gocke, X. Luo, D. Borek, D. R. Tomchick, M. Machius, Z. Otwinowski, & H. Yu, *Structural basis for CoREST-dependent demethylation of nucleosomes by the human LSD1 histone demethylase*. Mol Cell, 2006. 23: p. 377-87.
42. Zhang, R. G., M. L. Westbrook, E. M. Westbrook, D. L. Scott, Z. Otwinowski, P. R. Maulik, R. A. Reed, & G. G. Shipley, *The 2.4 A crystal structure of cholera toxin B subunit pentamer: choleragenoid*. J Mol Biol, 1995. 251: p. 550-62.
43. Jia, D., T. S. Gomez, Z. Metlagel, J. Umetani, Z. Otwinowski, M. K. Rosen, & D. D. Billadeau, *WASH and WAVE actin regulators of the Wiskott-Aldrich syndrome protein (WASP) family are controlled by analogous structurally related complexes*. Proc Natl Acad Sci USA, 2010. 107: p. 10442-7.
44. Matos, M. F., Y. Xu, I. Dulubova, Z. Otwinowski, J. M. Richardson, D. R. Tomchick, J. Rizo, & A. Ho, *Autoinhibition of Mintl adaptor protein regulates amyloid precursor protein binding and processing*. Proc Natl Acad Sci USA, 2012. 109: p. 3802-7.
45. Prochazkova, K., K. Cermakova, P. Pachl, I. Sieglova, M. Fabry, Z. Otwinowski, & P. Rezacova, *Structure of the effector-binding domain of the arabinose repressor AraR from Bacillus subtilis*. Acta Crystallogr D Biol Crystallogr, 2012. 68: p. 176-85.
46. Read, R. J., P. D. Adams, W. B. Arendall, 3rd, A. T. Brunger, P. Emsley, R. P. Joosten, G. J. Kleywegt, E. B. Krissinel, T. Lutteke, Z. Otwinowski, A. Perrakis, J. S. Richardson, W. H. Sheffler, J. L. Smith, I. J. Tickle, G. Vriend, & P. H. Zwart, *A new generation of crystallographic validation tools for the protein data bank*. Structure, 2011. 19: p. 1395-412.
47. Borek, D., M. Cymborowski, M. Machius, W. Minor, & Z. Otwinowski, *Diffraction data analysis in the presence of radiation damage*. Acta Crystallogr D Biol Crystallogr, 2010. 66: p. 426-36.
48. Borek, D., S. L. Ginell, M. Cymborowski, W. Minor, & Z. Otwinowski, *The many faces of radiation-induced changes*. Journal of Synchrotron Radiation, 2007. 14: p. 24-33.
49. Borek, D., K. Michalska, K. Brzezinski, A. Kisiel, J. Podkowinski, D. T. Bonthron, D. Krowarsch, J. Otlewski, & M. Jaskolski, *Expression, purification and catalytic activity of Lupinus luteus asparagine beta-amidohydrolase and its Escherichia coli homolog*. European Journal of Biochemistry, 2004. 271: p. 3215-3226.
50. Chang, C. I., Y. Chelliah, D. Borek, D. Mengin-Lecreulx, & J. Deisenhofer, *Structure of tracheal cytotoxin in complex with a heterodimeric pattern-recognition receptor*. Science, 2006. 311: p. 1761-4.
51. Huerta, C., D. Borek, M. Machius, N. V. Grishin, & H. Zhang, *Structure and mechanism of a eukaryotic FMN adenylyltransferase*. J Mol Biol, 2009. 389: p. 388-400.
52. Pei, J. & N. V. Grishin, *PROMALS: towards accurate multiple sequence alignments of distantly related proteins*. Bioinformatics, 2007. 23: p. 802-8.
53. Sadreyev, R. & N. Grishin, *COMPASS: a tool for comparison of multiple protein alignments with assessment of statistical significance*. J Mol Biol, 2003. 326: p. 317-36.
54. Shi, S., Y. Zhong, I. Majumdar, S. Sri Krishna, & N. V. Grishin, *Searching for three-dimensional secondary structural patterns in proteins with ProSMoS*. Bioinformatics, 2007. 23: p. 1331-8.
55. Grishin, N. V., *Fold change in evolution of protein structures*. J Struct Biol, 2001. 134: p. 167-85.
56. Yang, J., M. S. Brown, G. Liang, N. V. Grishin, & J. L. Goldstein, *Identification of the acyltransferase that octanoylates ghrelin, an appetite-stimulating peptide hormone*. Cell, 2008. 132: p. 387-96.
57. Zhao, Z., Y. Tuakli-Wosornu, T. A. Lagace, L. Kinch, N. V. Grishin, J. D. Horton, J. C. Cohen, & H. H. Hobbs, *Molecular characterization of loss-of-function mutations in PCSK9 and identification of a compound heterozygote*. Am J Hum Genet, 2006. 79: p. 514-23.
58. He, S., C. McPhaul, J. Z. Li, R. Garuti, L. Kinch, N. V. Grishin, J. C. Cohen, & H. H. Hobbs, *A sequence variation (I148M) in PNPLA3 associated with nonalcoholic fatty liver disease disrupts triglyceride hydrolysis*. J Biol Chem, 2009. 285: p. 6706-15.
59. Berge, K. E., H. Tian, G. A. Graf, L. Yu, N. V. Grishin, J. Schultz, P. Kwiterovich, B. Shan, R. Barnes, & H. H. Hobbs, *Accumulation of dietary cholesterol in sitosterolemia caused by mutations in adjacent ABC transporters*. Science, 2000. 290: p. 1771-5.

60. Garcia, C. K., K. Wilund, M. Arca, G. Zuliani, R. Fellin, M. Maioli, S. Calandra, S. Bertolini, F. Cossu, N. Grishin, R. Barnes, J. C. Cohen, & H. H. Hobbs, *Autosomal recessive hypercholesterolemia caused by mutations in a putative LDL receptor adaptor protein*. Science, 2001. 292: p. 1394-8.
61. Nijhawan, D., M. Fang, E. Traer, Q. Zhong, W. Gao, F. Du, & X. Wang, *Elimination of Mcl-1 is required for the initiation of apoptosis following ultraviolet irradiation*. Genes Dev, 2003. 17: p. 1475-86.
62. Li, P., D. Nijhawan, I. Budihardjo, S. M. Srinivasula, M. Ahmad, E. S. Alnemri, & X. Wang, *Cytochrome c and dATP-dependent formation of Apaf-1/caspase-9 complex initiates an apoptotic protease cascade*. Cell, 1997. 91: p. 479-89.
63. Widlak, P. & W. T. Garrard, *Discovery, regulation, and action of the major apoptotic nucleases DFF40/CAD and endonuclease G*. J Cell Biochem, 2005. 94: p. 1078-87.
64. Widlak, P. & W. T. Garrard, *Unique features of the apoptotic endonuclease DFF40/CAD relative to micrococcal nuclease as a structural probe for chromatin*. Biochem Cell Biol, 2006. 84: p. 405-10.
65. Widlak, P. & W. T. Garrard, *The apoptotic endonuclease DFF40/CAD is inhibited by RNA, heparin and other polyanions*. Apoptosis, 2006. 11: p. 1331-7.
66. Kulmala, S., A. Kulmala, T. AlaKleme, A. Hakanen, & K. Haapakka, *Intrinsic and 1-aminonaphthalene-4-sulfonate-specific extrinsic lyoluminescences of X-ray irradiated sodium chloride*. Analytica Chimica Acta, 1997. 340: p. 245-256.
67. Borek, D., S. L. Ginell, M. Cymborowski, W. Minor, & Z. Otwinowski, *The many faces of radiation-induced changes*. J Synchrotron Radiat, 2007. 14: p. 24-33.
68. Saran, M., W. Bors, & P. Lester, [2] *Pulse radiolysis for investigation of nitric oxide-related reactions, in Methods in Enzymology*. 1994, Academic Press. p. 20-34.
69. Hamilton, M. L., Z. Guo, C. D. Fuller, H. Van Remmen, W. F. Ward, S. N. Austad, D. A. Troyer, I. Thompson, & A. Richardson, *A reliable assessment of 8-oxo-2-deoxyguanosine levels in nuclear and mitochondrial DNA using the sodium iodide method to isolate DNA*. Nucleic Acids Res, 2001. 29: p. 2117-26.
70. Nakae, D., Y. Mizumoto, E. Kobayashi, O. Noguchi, & Y. Konishi, *Improved genomic/nuclear DNA extraction for 8-hydroxydeoxyguanosine analysis of small amounts of rat liver tissue*. Cancer Lett, 1995. 97: p. 233-9.
71. The 1000 Genomes Project Consortium, A., *A map of human genome variation from population-scale sequencing*. Nature, 2010. 467: p. 1061-73.
72. Menges, F., G. Narzisi, & B. Mishra, *TotalReCaller: improved accuracy and performance via integrated alignment and base-calling*. Bioinformatics, 2011. 27: p. 2330-7.
73. Kozarewa, I., Z. Ning, M. A. Quail, M. J. Sanders, M. Berriman, & D. J. Turner, *Amplification free Illumina sequencing-library preparation facilitates improved mapping and assembly of (G+C)-biased genomes*. Nat Methods, 2009. 6: p. 291-5.
74. Aird, D., M. G. Ross, W. S. Chen, M. Danielsson, T. Fennell, C. Russ, D. B. Jaffe, C. Nusbaum, & A. Gnirke, *Analyzing and minimizing PCR amplification bias in Illumina sequencing libraries*. Genome Biol, 2011. 12: p. R18.
75. Reshef, D. N., Y. A. Reshef, H. K. Finucane, S. R. Grossman, G. McVean, P. J. Turnbaugh, E. S. Lander, M. Mitzenmacher, & P. C. Sabeti, *Detecting novel associations in large data sets*. Science, 2011. 334: p. 1518-24.
76. Beier, D. R., *Sequence-based analysis of mutagenized mice*. Mamm Genome, 2000. 11: p. 594-7.
77. Wilsbacher, L. D., A. M. Sangoram, M. P. Antoch, & J. S. Takahashi, *The mouse Clock locus: sequence and comparative analysis of 204 kb from mouse chromosome 5*. Genome Res, 2000. 10: p. 1928-40.
78. Consortium, I. M. K., F. S. Collins, J. Rossant, & W. Wurst, *A mouse for all reasons*. Cell, 2007. 128: p. 9-13.
79. Austin, C. P., et al., *The knockout mouse project*. Nat Genet, 2004. 36: p. 921-4.
80. Kwak, E. L., et al., *Anaplastic lymphoma kinase inhibition in non-small-cell lung cancer*. N Engl J Med, 2010. 363: p. 1693-703.
81. Travis, W. D., et al., *International Association for the Study of Lung Cancer/American Thoracic Society/European Respiratory Society: international multidisciplinary classification of lung adenocarcinoma: executive summary*. Proc Am Thorac Soc, 2011. 8: p. 381-5.
82. Eberhard, D. A., et al., *Mutations in the epidermal growth factor receptor and in KRAS are predictive and prognostic indicators in patients with non-small-cell lung cancer treated with chemotherapy alone and in combination with erlotinib*. J Clin Oncol, 2005. 23: p. 5900-9.
83. Pleasance, E. D., et al., *A comprehensive catalogue of somatic mutations from a human cancer genome*. Nature, 2010. 463: p. 191-6.
84. Pleasance, E. D., et al., *A small-cell lung cancer genome with complex signatures of tobacco exposure*. Nature, 2010. 463: p. 184-90.
85. Ley, T. J., et al., *DNA sequencing of a cytogenetically normal acute myeloid leukaemia genome*. Nature, 2008. 456: p. 66-72.
86. Greenman, C., P. et al., *Patterns of somatic mutation in human cancer genomes*. Nature, 2007. 446: p. 153-8.
87. Mardis, E. R., et al., *Recurring mutations found by sequencing an acute myeloid leukemia genome*. N Engl J Med, 2009. 361: p. 1058-66.
88. Beroukhim, R., et al., *The landscape of somatic copy-number alteration across human cancers*. Nature, 2010. 463: p. 899-905.
89. Weir, B. A., et al., *Characterizing the cancer genome in lung adenocarcinoma*. Nature, 2007. 450: p. 893-8.

FIG. 2-1 The schematic view of the sequencing library preparation with the standard protocol of Illumina, and with our modifications. The asymmetric duplex formed after ligation of the adapters has two barcoding adapters (double-stranded) and four indexing adapters, which in our approach are partially randomized. The barcoding adapters will be used for multiplexing libraries, to monitor the quality and efficiency of dA tailing, ligation, and purification of libraries. The indexing adapters will be used in statistical analysis to identify the reads that coincidentally have the same length and the same barcoding adapters.

FIG. 2-2 The schematic view of the mechanism that preserves information about the directionality and identity of DNA template strands during PCR amplification, which generates the sequencing library. We use this feature in statistical analysis following sequencing to analyze the type and level of errors in sequencing and to confirm the presence of mutations.

FIG. 2-3 The Twin-seq principle in Illumina/Solexa pair-end sequencing.

Example 3. AHA Grant

Advanced age is correlated with increased risk for all cardiovascular disease (CVD) [1-3]. A number of studies have associated this correlation with the mitochondrial dysfunctions caused by the progressive accumulation of somatic mutations and oxidative damage in the mitochondrial genome (reviewed in [4-7]). However, systematic and definitive analysis of the subject is limited to just a few cases, and the subject is still debated [8]. We have developed a novel assay and validate it in a biological context, to enable precise, quantitative studies of somatic mutations, chemical damage, and levels of heteroplasmy in mitochondrial DNA.

In one aspect we developed an unbiased sequencing assay to map precisely and accurately the spectrum of somatic mutations in mitochondrial DNA. We designed the approach so that it differentiates between somatic mutations, oxidative damage of mtDNA, and changes to DNA introduced during experimental procedures. We achieve sensitivity that permits detection of 1 change in a mtDNA sequence per 1,000,000,000 bp, which is sufficient for detecting very low levels of heteroplasmy in mtDNA isolated from mitochondrial populations.

In another aspect we validated the assay in a biological context by sequencing the samples of heart tissue obtained from multiple cadaveric donors with variable age, sex and health status. For every tissue sample, we performed separate experiments on total mitochondrial isolation, and mitochondrial isolations enriched in subsarcolemmal and interfibrillar mitochondria. We determined the patterns and levels of both somatic mutations and DNA damage in mtDNA from all isolates. The sequencing was followed by data analysis to answer a variety of questions, including: (1) whether random drift is the only contributor to the observed mutational patterns; (2) whether there are any differences in the observed patterns in different mitochondrial isolates and if so, how they correlate with age and other biological factors; (3) what are the levels of heteroplasmy and how are they dependent on age and health status; (4) and how well do positions of lesions identified in mtDNA correlate with observed patterns of somatic mutations in mtDNA.

Our methods permit us to determine how the chemical and structural damage to mtDNA affects mitochondrial functions and consequently alters the performance of the tissues most dependent upon energy consumption. The assay and associated data analysis provide an excellent tool to quantitatively study these and related questions.

Background and Significance:

Cardiovascular disease is the leading cause of death and disability in developed countries and its onset and outcomes correlate with age [2, 9]. Multiple lines of evidence suggest that cardiovascular disease and aging are related to one another through decreased mitochondrial functioning [10-13].

Mitochondria are multi-functional organelles that perform several inter-dependent functions: they are responsible for the production of ATP in the cell by oxidative phosphorylation; they participate in calcium homeostasis; they activate and regulate cellular death pathways and they generate reactive oxygen species that can cause oxidative damage to a variety of biomolecules in high concentrations, but also have diverse signaling functions in concentrations below damaging thresholds [7, 14, 15]. Each mitochondrion contains multiple copies of its own, 16,569 bp genome, which is organized into a nucleoid [16]. The nucleoid has a complex structure that changes with age [17, 18]. Mitochondria are inherited maternally [19] and therefore the mtDNA lineages are clonal. Each cell contains hundreds to thousands of mitochondria [20], generated by proliferation, which is not synchronized with mitosis.

Mitochondria are particularly important in the functioning of cardiac myocytes, in which thousands of spatially-organized mitochondria support continuous delivery of ATP to maintain heart muscle contraction. The myocardium contains two distinct types of mitochondria; subsarcolemmal (SSM), remaining in contact with the sarcolemma, and interfibrillar (IFM), located between the contractile filaments [13, 21]. They differ in their cristae morphology, lamelliform for SSM and tubular for IFM mitochondria, and in multiple functional characteristics [5, 22, 23], such as their rate of oxidative phosphorylation [23, 24], association with specific proteins [25, 26], and calcium retention capacity [27]. It was suggested that SSM mitochondria may serve a signaling function and IFM mitochondria may be responsible for protecting against damaging events [28].

Deletions and point mutations in mtDNA are the cause of multiple mitochondrial disorders [29-31] with diverse phenotypic manifestations, including cardiovascular problems [29]. The mutation rate of mitochondrial DNA is reported to be about two-orders of magnitude higher than that of nuclear DNA [32]. The explanation for this difference frequently invokes a combination of high concentrations of reactive oxygen species, which are produced in mitochondria during oxidative phosphorylation, with less robust mechanisms of DNA repair and mtDNA molecules being relatively exposed to chemical attack [33]. The higher mutational rate, together with proliferation that is not coupled to the cell cycle, results in heteroplasmy—cells harboring a mixture of different mitochondrial genomes (reviewed in [34-36]). The level of heteroplasmy correlates with the severity of some mitochondrial diseases [37], and in some disorders it has to cross a threshold value for the disease to manifest [38-41]. Improved methods for detecting mutations have shown that heteroplasmy is relatively common [42-44], its levels differing between tissue types [32, 45], and that it correlates with increasing age [41, 46]. However, the mechanism that leads to reaching the threshold values of heteroplasmy is not fully understood. The generally accepted model of the formation of heteroplasmic mitochondrial populations invokes a combination of random genetic drift with relaxed replication [47], but the subject is still debated [48], with some data indicating increased homoplasmy in particular positions of mtDNA, suggesting selective pressure [49]. During maternal transmission, mutated mitochondrial DNA undergoes strong purifying selection against nonsynonymous mutations in protein-coding genes [50, 51], which shows that cells have cellular mechanisms to exert selective pressure.

The association of CVD with levels of mutations and heteroplasmy in mtDNA was shown a number of times, including an increased level of damage to mtDNA in atherosclerotic lesions [52]. Over 1,000 variants of mtDNA mutations have been reported in the context of cardiomyopathies, heart failure, and other CVD [53]. The correlations of mtDNA damage, mutations, and heteroplasmy levels with aging are also well-established [49, 54]. Development of the mice expressing a version of mitochondrial DNA polymerase, PolgA [54], mutated for proofreading activity, provided some additional clues. The mutant had increased levels of mutations in mtDNA and many features of premature aging, including a shorter life span [54, 55]. Subsequent studies of PolgA$^{mut/mut}$ mice revealed that the shorter life span is related to short deletions in mtDNA combined with clonal expansion of mutated versions in heart and brain tissues [56]. However, these findings have been refuted (discussed in [57]). Another important report showed that overexpression of catalase in PolgA$^{mut/mut}$ mice mitigates the age-related cardiomyopathy [58], which suggests some contribution from oxidative damage. The recent discovery that strong inhibitors of PolgA, used in anti-retroviral therapy, results in accelerated aging further confirmed the significance of mtDNA mutations [59]. The vascular age of HIV-infected patients treated with those inhibitors increased their chronological age by over 15 years on average 15 years [60]. In silico analysis suggested that accelerated aging resulted from the clonal expansion of preexisting mutated versions of mtDNA rather than from increased mutagenesis [59], again stressing the importance of heteroplasmy in development of CVD and other complex diseases.

Many debates could be resolved if we had better methods to measure levels of mutation and heteroplasmy in the mitochondrial genome [7, 61], oil Classical Sanger sequencing requires at least 20% of mtDNA to be mutated to detect a mutation [62]. It renders this method unfeasible for the direct characterization of heteroplasmic populations of mitochondria. Another group of methods combines PCR amplification of mtDNA performed with multiple primers spanning the mitochondrial genome. The obtained amplified fragments are cloned and traditionally sequenced. Because the method has a rather low sensitivity of 4 mutations per 10,000 bp, it is not suited for detecting low levels of heteroplasmy. The single molecule PCR technique is applied to undigested or lightly digested mtDNA samples [63]. The structure of mtDNA becomes increasingly complex with age, and this complexity may be related to mtDNA replication and/or to mtDNA repair processes [17, 18, 64]. smPCR may bias the results by selective exclusion of some of the regions, which due to their structure might be inaccessible to PCR primers. Another method, the random mutation capture (RMC) assay, has excellent sensitivity, detecting 1 mutation per 1,000,000,000 [65-67]. The frequency of mutations is measured by quantifying the changes in the TagI restriction site. The point mutation in the TagI site generates a fragment of DNA that is resistant to digestion, which enables its detection and quantification by qPCR. However, the TagI site has only four base pairs and is present in mtDNA only 23 times. This severely restricts the applicability of the assay in the context of determining mutational spectra.

Our method belongs to a broad group of next-generation sequencing approaches which generally are considered to have a high level of intrinsic errors. The effects contributing to the sequencing errors are fully correctable, and correcting them results in unprecedented sensitivity. There were efforts to use next-generation sequencing to determine and quantify somatic mutations in mitochondria [44, 68-71], including studies of cardiomyopathies [72]. In all of these reports, the authors struggled with estimating the sequencing errors, and could at best detect heteroplasmy at the level of 1.6% [43], while in most cases requiring the level of heteroplasmy to exceed 5%. In several of those approaches, the mitochondrial DNA was enriched by PCR amplification before library generation, which could introduce additional biases and false positives. In some of the reports, the libraries were not properly randomized [73] to avoid coincidences, which could severely affect conclusions. The apparent duplicates are removed from analysis, however without the randomization, it is not clear if the duplicates arise from clonal amplification or from coincidence. In other reports, the procedures of randomization are not described sufficiently to determine how they affected the results. Data analysis, even if described in detail, involved many arbitrary decisions that could again result in false positives. Additionally, lack of external validation standards makes comparisons between different results difficult [7].

Our method addresses all of those problems. It is sensitive at the level of RMC assays, resistant to the experimental errors introduced by PCR or by fixation of chemical lesions in DNA, covers the full mtDNA genome, and addresses topological concerns. Our methods preserve the information about the strand origin through the whole procedure of sequencing library generation. For example, we used in preliminary studies, strand information is preserved from fragmentation, which yields double-stranded DNA fragments, until the completion of the sequencing adapters' ligation.

As in conventional Illumina sequencing each read results from sequencing of a polony. Polonies are started by annealing single-stranded DNA to the specific oligonucleotides covering the surface of the flow-cell. The sequences that anneal to oligonucleotides on the flow-cell come from the sequencing adapters that were ligated to both ends of the dsDNA fragment prior to polony generation. The sequencing adapters are not entirely double-stranded; instead, they have a special Y-structure design, in which the double-stranded stem ligates to dsDNA while the arms remain single-stranded. The adapters' design in combination with the polarity of the DNA strands results in a ligation product that has built-in asymmetry. Therefore, regardless of what happens to the dsDNA fragment after ligation, it is possible to recover the information about the polarity of the original strand that lead to the particular sequencing read.

We also know in advance that somewhere on the flow-cell there should be another polony that was formed by amplifying the complementary strand that was part of the dsDNA fragment. Combining the information from these two particular reads would be invaluable, particularly if we could identify them with high certainty. A related feature is used to some extent in strand-specific RNA sequencing, but was never adapted to the context of uncertainty analysis in dsDNA sequencing. So one aspect of our method is to generate a hierarchy of consensuses between the sequencing reads and use those consensuses to identify somatic mutations, chemical damage, and experimental errors. To achieve it, at the level of PCR amplification which in standard Illumina protocol selects the properly ligated fragments, we restrict the amount of starting material to obtain multiple, clonally-amplified reads from the original DNA fragment. Each dsDNA fragment will result in two identifiable groups of paired-end reads. Each identified group has to originate from a single DNA strand, and so we should also observe the group that corresponds to its complementary strand. The level of PCR clonal amplification should be sufficiently high so as to: (1) increase the probability that the reads from both complementary strands are observed; (2) reach the desired reliability; and (3) improve the uncertainty estimates and the diagnosis of problems. We can use several powerful statistical approaches, first analyzing the internal consistency within the reads that were clonally-amplified from a single-stranded piece of DNA, then analyzing the consistency between this group and the clonally-amplified group corresponding to its complementary strands, and finally analyzing the consistency between the sequencing reads that resulted from different dsDNA fragments. The second analysis is very powerful, and is related to the independence of the two complementary strands. During the very first PCR cycle, the ligation product is denatured and the subsequent fates of the separated DNA strands, together with their amplified products, are independent from one another with respect to the potential introduction of errors. To identify rare mutations, we need a much higher level of confidence than that generated by a single sequencing read, so we increase confidence by combining information from multiple reads. To do so properly, we identify which components of uncertainty in multiple reads are independent from each other. An important part of our experimental design is to identify and control for the impact of those cases where the errors of different sequencing reads are not independent.

We performed a group of sequencing experiments that followed from this idea and tested the level of somatic mutations in the genomes of three *E. coli* strains: one wild-type strain MG1655, and two mutator strains with defects in their mismatch-repair pathways. Samples were prepared according to the standard Illumina protocol, except for custom multiplexing and modification at the PCR step.

By diluting the input sample to contain 200 fg of DNA and increasing the number of PCR cycles to 27, we introduced an approximately 25-fold clonal amplification, while keeping the PCR artifacts to a minimum. To increase the reliability of clonal cluster identification, we added randomized bases to the sequencing adapters at the start of the read position, in this way differentiating most of the potential sequence coincidences. The sequencing was performed on Illumina GA-II$_x$ with paired-end reads 130 bp long. We started with the Illumina pipeline up to the stage of base-calling, and then used only custom-built programs, with the exception of Bowtie [74], which was used for mapping the reads onto the *E. coli* genome. For the three reactions we mapped 98.85%, 99.70%, and 99.74% of the sequencing reads to the *E. coli* genome. This indicates that the experiments were of very high quality. Then, we analyzed all discrepancies, paying particular attention to those consistently present within each group of clonal copies.

We identified several sources of problems, with one type that mimicked somatic mutations. Standard Illumina sample preparation that disrupts DNA by sonication or nebulization introduces uneven breaks on both DNA strands, which need to be repaired enzymatically. This is done using a T4 DNA polymerase. When the polymerase encounters a chemically altered base, e.g. 8-Oxoguanine (8-Oxo-G) in the overhang, it can insert the wrong nucleotide into the opposite strand. Such a damaged base may induce the same type of mispairing later during PCR amplification. Consequently, one chemical event causes a coupled sequencing error that appears in both groups of reads. The same type of coupled error may arise when the original DNA duplex contains a nick on one of its strands, which is then repaired by the combined actions of exonuclease digestion and strand copying, starting from the nick. These repair effects can manifest themselves as a surplus of coupled errors in both strands, concentrated close to the ligation site. For those types of errors, we expect very diverse frequencies across all 12 possible types of substitution, because the chemistries generating base damage are very different. In contrast, the somatic mutation frequency for complementary types of substitution (e.g. G→T and C→A) should be the same, as they are only differentiated by the polarity of the strand used for sequencing. While fill-in originating errors are concentrated close to the ends of the sequenced DNA, somatic mutations should be randomly distributed along the reads. Our data show coupled sequence-change events close to the sequencing start for only four substitution types: G→T, G→C, A→T and C→T, and not even one instance of the complementary types. This indicates that the source of these sequencing changes is damage to the bases in the library rather than somatic mutations. The most frequently observed change is G→T substitution, which would result from the oxidation of guanidine to 8-Oxo-G, generated by reactive oxygen species during the storage of DNA samples. After correcting for all errors, including those generated by fill-in and nick repair reactions, we observed in the wild type MG1655 *E. coli* a single coupled (T→G, A→C) change in 31,000,000 analyzed positions. The presence of a single mutation is consistent with our expectation of about 0.7 mutations present in the wild-type *E. coli* genome after 300 generations of cells with faithfully working replication apparatus. For the mutT-defective and the uvrD-defective strains, we found 20 and 24 mutations, respectively. Both the numbers and patterns of mutations agreed with predictions, after the correction for the number of generations. This was definitive proof that our strategy for avoiding false positives was successful. At this point, we have already achieved sensitivity of $3.2 \cdot 10^{-8}$, which is ~30 times higher than any other unbiased, genome-wide approach for mapping of somatic mitochondrial mutations. To use the method to describe somatic mutations in mitochondria, and to quantify levels of heteroplasmy, we introduced several further improvements.

1. Mapping Precisely and Accurately the Spectrum of Somatic Mutations in Mitochondrial DNA.

We isolate mitochondria using differential centrifugation followed by purification in a sucrose gradient as described in the Vermulst report [67]. After isolation and purification of mtDNA, we follow the modified protocol for preparing the Illumina sequencing library.

An improvement is removing the coupled errors arising from the end-repair reaction after DNA fragmentation. We eliminate this reaction entirely, by fragmenting the DNA with double-strand-specific, apoptotic DNA endonuclease DFF40, which has been thoroughly characterized and is known to produce blunt ends with a 5' phosphate extension [77-79]. DFF40 is activated by adding TEV protease and stopped by curcumin [78]. The dsDNA fragmentation is followed by extending the blunt ends with dA and ligating the sequencing adapters.

Another improvement is introducing properly randomized adapters. Previously we partially randomized two bases that were ligated to a dsDNA fragment. These two bases were preceded with a three or four base long non-randomized part that served as a multiplexing adapter. Our analysis is based on analyzing the hierarchy of alignments between reads, where identifying the uniqueness of the read with high certainty is critical. The uniqueness is defined by a combination of factors; the presence of a specific multiplexing adapter, the length of the read, and the complementary strand having complementary properties—the same length and complementary adapters. Our randomization strategy was sufficient for the *E. coli* genome, which is 4.6 Mbp, and the level of randomization minimized to acceptable levels the probability of accidental coincidences, i.e. having the length and the type of adapter the same for two different dsDNA fragments. However, the mitochondrial genome is 280× smaller, which significantly increases the chances of coincidences. Therefore, here we fully randomize the two bases used for ligation, each base is preceded by a four to six base long, non-randomized multiplexing adapter, and this adapter is preceded by the standard Illumina adapter sequence. These modifications sufficiently randomize the requirements for the read length.

Illumina recently introduced the index adapter, which is placed in the single-stranded part of the Y adapter. The process is designed in such way that this 6 bp long sequence does not have to be defined to be properly sequenced. Therefore, to validate that we did not accidently count different reads twice, we fully randomize this sequence in our adapters. That way, if we have the cluster of reads with the same length of the sequence, the same multiplexing adapter at the ligation site, but with different sequences in the index site, we will know that we have two different sequences (coincidence). The complementary strands have differently randomized index sequences; however, their multiplexing parts will be the same. This built-in control for coincidences helped us to develop the assay and data analysis better. In cases our randomization is insufficient, we can extend the randomized part of the multiplexing adapter, and can easily use at least 128 adapters, having different multiplexing parts of the adapter and randomized indexing parts of the adapter. After the ligation of the adapters, we perform size selection either by gel excision or by purification with magnetic beads technology. We have used both methods, and both are sufficient for our purposes. We follow with quantification by the Pico-Green assay. We perform the appropriate dilution to follow with PCR amplification, which will both select the appropriately ligated fragments, and induce clonal amplification. In some applications we do not want to clonally amplify just one mitochondrion, as there are thousands of them in each cell, and multiple cells in each tissue, which may have mosaic patterns of mitochondrial behavior [80, 81]. For these we use multiplexed sequencing to see how the level of starting DNA affects the results of the heteroplasmy analysis. In each case, we introduce the same level of clonal amplification, and adjust the number of PCR cycles to avoid artifacts. For that, we use the newly introduced Kapa Q-PCR that allows for the determination of the most optimal number of PCR cycles. After purification, the reactions are pooled and submitted for sequencing. The ratio of mixing the libraries for multiplexing is determined by Q-PCR.

We found the PCR reactions to be a tolerably small contributor to sequencing errors. The Phusion polymerase used in our preliminary studies generates on average $4.4 \cdot 10^{-7}$ errors per base, per replication cycle [NEB materials]. This error rate needs to be multiplied by the number of PCR cycles, producing a contribution of $\sim 10^{-5}$ to the error frequency for a single read. An additional contribution of $1.5 \cdot 10^{-5}$ comes from the error rate of the Bst DNA polymerase [82], which during polony generation synthesizes a first copy of a particular single-stranded DNA piece annealed to a short oligonucleotide covalently attached to the Illumina flow-cell. The original strand is removed and the Bst-generated copy becomes the template for the whole polony. The errors introduced in PCR are highly dispersed, with the majority of correlated errors originating from the first PCR cycle. For instance, the probability that two clonal copies with the same pattern of sequence changes resulted from the same error in the first PCR cycle is $0.25 \cdot 4.4 \cdot 10^{-7}$. If one adds the contribution from subsequent cycles, the probability of such an event is $0.33 \cdot 4.4 \cdot 10^{-7} = \sim 1.5 \cdot 10^{-7}$. This level is sufficiently high to be identified in our analysis, but does not generate problems, because we also use information resulting from analysis of clonal copies of the strand complementary to one with PCR errors. The PCR error level is often perceived to be much higher. One reason for this is confusing the PCR reaction that generates error with the chemical damage to the template, which will induce formation of incorrect copies even if PCR amplification is faithful. In our approach, we can identify the chemical damage existing prior to the PCR step. The chemical damage to a particular base results in multiple strand-specific errors in a clonal group of reads, which do not correlate with errors in the complementary clonal group. We are using short fragments of dsDNA (200-300 bp) and controlled conditions of PCR amplification; therefore, we do not have problems with artifacts resulting from jumping PCR [83].

We inadvertently created chemical damage during our preliminary experiments and our analysis could recognize it as a specific type of error that needs to be controlled better. During data analysis, we realized that the ligated libraries, stored at 4° C. when the conditions of PCR to introduce clonal amplification were tested, accumulated some level of chemical modifications that resulted in a quite significant number of sequencing errors, mainly G→T substitutions (guanidine oxidation), at the level of $6 \cdot 10^{-4}$. The contribution of this effect to the false positive mutation calls was nevertheless small. The chemical modification affects only one strand, therefore the change occurs in only one type of clonal cluster, and is not present in the clonal clusters corresponding to the complementary strand. Instead, those reads provide us with information about the oxidative damage level. In the case of mtDNA, we would like to separate in vivo and ex vivo oxidative lesions. Therefore, we perform all reactions faster, store them frozen if necessary, and add scavengers of radical and hydrated electrons. The most probable source of damaging radicals is contamination with iron cations, which could be removed by chelation. However, we cannot add chelators, because it would also affect in an unpredictable way the enzymatic reactions used in the library preparation, which depend on magnesium concentrations. Instead we add micromolar concentrations of sodium iodide and sodium nitrate, which we found to be effective in scavenging hydrated electrons and hydroxyl radicals, respectively [84-87]. Sodium iodide was used in procedures that minimize the oxidative damage to guanidine, although without invoking the scavenger justification [88, 89]. Finally, to be sure that we control and identify our signatures correctly, we introduce spike-in controls into the sequencing reactions. We order 30 to 40 bp long oligonucleotides with a defined sequence not present in any genome, and in which specific modifications such as an abasic site, 8-oxo-G, etc., are introduced at specified positions. We anneal them with their "undamaged" complements and add them in very low concentrations, 1:500,000 ratio or lower depending on the capacity of the sequencing lane, to fragmented mtDNA. The spike-in controls are processed together with mtDNA, using the approach described above. It provides information about the patterns and specificities of the polymerases used in the process, about their error levels, and also about performance, sensitivity and other qualitative and quantitative parameters of our approach. This allows us to introduce probabilistic modeling of correlated errors in clonal cluster reads. This modeling is an improvement over existing methods [90] by considering chemically-modified DNA bases as intermediates in error generation in the PCR amplifications before the sequencing and during polony formation. Spike-in control together with mtDNA reads helps us to determine the minimal coverage of the mitochondrial genome required to achieve the desired sensitivity. This issue is debated [72], but the required coverage depends on the error levels. We cannot control random fluctuations; however, we decrease the impact of all systematic effects. This in combination with increased scale, which we achieve by using Hi-Seq 2000 with v3 chemistry, will re-define current requirements for minimal coverage. Error reductions and control of systematic effects arising from the library preparation is the first component leading to the unprecedented sensitivity of our method. The second component results from better analysis and detection of instrumental errors and effects.

Not all damaged bases can serve as templates for polymerases. Therefore, some types of damage cannot be mapped by this method. We may be able to map the UV induced cross-links, as we observed that they do create a specific signature in the sequencing reaction. Even without mapping the position of damage, we will still get the information about the lack of PCR amplification on the damaged strand, when its complement should be amplified without problem. "Single-strandedness" due to damage will have different properties that "single-strandedness" due to presence of single-stranded DNA in the mitochondrial genome. In first case, we will observe a lack of complementary reads; in second case, we will observe a decrease of coverage in some of the regions. The assay has potential to be used sequentially: (1) first to prepare the library of longer dsDNA fragments with specific adapters, (2) then, treatment of the library with specific enzymes recognizing DNA lesions and generating the break, (3) and ligating another adapter to the newly created cut. We may perform such experiments, if the data analysis indicates that we have a problem with non-interpreted sources of DNA damage.

We perform the polony identification, fluorescence signal estimation, base-calling and initial, so-called purity filtering with standard Illumina software.

Then we compare all those sequences to the reference mitochondrial genome using Bowtie [74]. This operation separates the mitochondrial reads from the nuclear reads, thereby preventing contamination. However, at this point we still keep the nuclear mitochondrial sequences (NumtS) in the pool of sequencing reads [91]. We assemble the reference mitochondrial genome, which allows us to separate the reads originating from genomes with large deletions or rearrangements, which we analyze separately later. We follow it with clustering the clonal reads with custom-made scripts. The next level of quality filtering is based on both segments of a paired-end read exceeding a specified quality threshold. Then, we cluster the sequences to identify clonal copies, initially for each strand separately, and then combining pairs of clonal clusters. This step is performed through a hierarchical analysis: first, a fast, rough clustering is performed, with criteria set so as not to miss a potential hit, at the cost of merging some clusters together. In the next step, a more elaborate, singular value decomposition (SVD) analysis differentiates random events from potential systematic differences within the cluster, which are classified on the basis of correlations within the cluster as either arising from similar sequences within the genome (coincidences and/or polymorphisms) or from correlated sources of error, e.g. from chemical damage or PCR amplification. SVD analysis will also clearly identify NumtS, so that we can reject them. Decision thresholds in this analysis rely on the probabilistic error model that is also subject to improvement after the initial clustering is performed. To enable Bayesian reasoning, we explicitly model the events that can generate errors in multiple reads of the particular clonal cluster. In the normal use of Illumina sequencing, the clonal amplification reads are typically filtered out before aligning multiple reads to identify mutations or polymorphisms. In our analysis, they are utilized. However, the Q-values, the statistical indicators that describe the quality of the base-calling process, will not be independent for clonally-amplified reads. We use Q-values as a part of our analysis; therefore we recalibrate them to take into account the clonal amplification. We adapt the GATK Q-value recalibration procedure [92]. After recalibration, we can assume that the majority of sequences have been properly analyzed so as not to have somatic mutations, and the evidence of somatic mutations in the others is strong enough not to be doubted. At this point, we follow standard approaches of analyzing the identified variants in the context of the mitochondrial genome. We determine the point mutation frequency by calculating the median number of mutations per nucleotide site, analyze the distribution of point mutations in the mitochondrial genome, analyze the type of mutations (transitions vs. transversions), identify mutational hotspots, and analyze insertion and deletion. We perform paired-end sequencing, with the length of reads at least 100 bp; therefore, we can identify short insertions frequently present in the mitochondrial DNA, and also small structural rearrangements. For these mutations, we analyze the patterns, frequency and genomic distributions as well.

Samples of human heart tissues can be obtained from the National Disease Research Interchange. The number of samples depends to some extent on the assay performance, and the number of Hi-seq 2000 lanes used to achieve this performance We analyze mitochondria from 15 different cadaveric samples using samples from donors of different ages, and both sexes—random stratification helps detect a very low level of heteroplasmy. With our high sensitivity approach, even younger donors have detectable levels of heteroplasmy.

Total mitochondrial isolation are prepared, and separately, fractions of SSM and IFM mitochondria (Palmer et al. [21, 27]). The three samples can be treated as separate libraries, but because they originate from a single donor, there is overlap between total mitochondrial isolation and either SSM or IFM isolations. Preparations of IFM mitochondria are contaminated with SSM mitochondria and that total mitochondria fraction contains predominantly SSM mitochondria [28, 93]. Having data from all three samples allows us to statistically model the identified effects as a function of their presence and their levels in a particular population. The fractionation of SSM and IFM uses short enzymatic digestion to release the IFM fraction, which is tightly bound to the muscle fibers. An alternative procedure to prepare the SSM and IFM fractions can be used [94].

We follow the protocol described above for preparation of sequencing libraries, and spike-in controls, and analyze how populations of SSM and IFM mitochondria differ from one another, and across the donors. We determine for each population in each donor the point mutation frequency, analyze the distribution of point mutations in mitochondrial genomes, analyze the types of mutations (transitions vs. transversions), identify mutational hotspots, analyze patterns and frequencies of insertions, deletions, and small structural rearrangements. Then, having fully characterized the differences, we properly cluster the data for further analysis, and for each donor, we analyze the mtDNA heteroplasmy. There are several theoretical models of the heteroplasmy distribution expected from random genetic drift (discussed in [95]). We quantify the level of oxidative damage lesions and correlate their presence with the patterns of somatic mutations in mitochondrial DNA present both in our samples, and identified previously. Our analysis provides a quantitative estimate of "single-strandedness" across the genome.

Finally, we also perform correlative analysis of the patterns and levels of DNA damage, somatic mutations and heteroplasmy with age and other biological information about donors.

Our results, together with the developed approach and generated data, provide invaluable insight into the function of mitochondria in the development of cardiovascular disease.

1. Bleumink, G. S., et al., *Quantifying the heart failure epidemic: prevalence, incidence rate, lifetime risk and prognosis of heart failure The Rotterdam Study*. Eur Heart J, 2004. 25: p. 1614-9.
2. Hoyert, D. L., M. P. Heron, S. L. Murphy, & H. C. Kung, *Deaths: final data for 2003*. Natl Vital Stat Rep, 2006. 54: p. 1-120.
3. Ren, J., L. Pulakat, A. Whaley-Connell, & J. R. Sowers, *Mitochondrial biogenesis in the metabolic syndrome and cardiovascular disease*. J Mol Med (Berl), 2010. 88: p. 993-1001.
4. Gustafsson, A. B. & R. A. Gottlieb, *Heart mitochondria: gates of life and death*. Cardiovasc Res, 2008. 77: p. 334-43.
5. Hoppel, C. L., B. Tandler, H. Fujioka, & A. Riva, *Dynamic organization of mitochondria in human heart and in myocardial disease*. Int J Biochem Cell Biol, 2009. 41: p. 1949-56.
6. Khrapko, K., *The timing of mitochondrial DNA mutations in aging*. Nat Genet, 2011. 43: p. 726-7.
7. Larsson, N. G., *Somatic mitochondrial DNA mutations in mammalian aging*. Annu Rev Biochem, 2010. 79: p. 683-706.
8. Trifunovic, A., et al., *Somatic mtDNA mutations cause aging phenotypes without affecting reactive oxygen species production*. Proc Natl Acad Sci USA, 2005. 102: p. 17993-8.
9. Sheydina, A., D. R. Riordon, & K. R. Boheler, *Molecular mechanisms of cardiomyocyte aging*. Clin Sci (Lond), 2011. 121: p. 315-29.
10. Ingwall, J. S., *Energy metabolism in heart failure and remodelling*. Cardiovasc Res, 2009. 81: p. 412-9.
11. Neubauer, S., *The failing heart—an engine out of fuel*. N Engl J Med, 2007. 356: p. 1140-51.
12. Ventura-Clapier, R., A. Garnier, V. Veksler, & F. Joubert, *Bioenergetics of the failing heart*. Biochim Biophys Acta, 2011. 1813: p. 1360-72.
13. Lesnefsky, E. J., S. Moghaddas, B. Tandler, J. Kerner, & C. L. Hoppel, *Mitochondrial dysfunction in cardiac disease: ischemia—reperfusion, aging, and heart failure*. J Mol Cell Cardiol, 2001. 33: p. 1065-89.
14. Sauer, H., M. Wartenberg, & J. Hescheler, *Reactive oxygen species as intracellular messengers during cell growth and differentiation*. Cell Physiol Biochem, 2001. 11: p. 173-86.
15. Pinton, P., C. Giorgi, R. Siviero, E. Zecchini, & R. Rizzuto, *Calcium and apoptosis: ER-mitochondria Ca2+ transfer in the control of apoptosis*. Oncogene, 2008. 27: p. 6407-18.
16. Garrido, N., et al., *Composition and dynamics of human mitochondrial nucleoids*. Molecular Biology of the Cell, 2003. 14: p. 1583-96.
17. Pohjoismaki, J. L., et al., *Developmental and pathological changes in the human cardiac muscle mitochondrial DNA organization, replication and copy number*. PLoS One, 2010. 5: p. e10426.
18. Pohjoismaki, J. L., et al., *Human heart mitochondrial DNA is organized in complex catenated networks containing abundant four-way junctions and replication forks*. J Biol Chem, 2009. 284: p. 21446-57.
19. Giles, R. E., H. Blanc, H. M. Cann, & D. C. Wallace, *Maternal inheritance of human mitochondrial DNA*. Proc Natl Acad Sci USA, 1980. 77: p. 6715-9.
20. Veltri, K. L., M. Espiritu, & G. Singh, *Distinct genomic copy number in mitochondria of different mammalian organs*. J Cell Physiol, 1990. 143: p. 160-4.
21. Palmer, J. W., B. Tandler, & C. L. Hoppel, *Biochemical properties of subsarcolemmal and interfibrillar mitochondria isolated from rat cardiac muscle*. J Biol Chem, 1977. 252: p. 8731-9.
22. Riva, A., B. Tandler, F. Loffredo, E. Vazquez, & C. Hoppel, *Structural differences in two biochemically defined populations of cardiac mitochondria*. Am J Physiol Heart Circ Physiol, 2005. 289: p. H868-72.
23. Hoppel, C. L., B. Tandler, W. Parland, J. S. Turkaly, & L. D. Albers, *Hamster cardiomyopathy. A defect in oxidative phosphorylation in the cardiac interfibrillar mitochondria*. J Biol Chem, 1982. 257: p. 1540-8.
24. Padrao, A. I., et al., *OXPHOS susceptibility to oxidative modifications: the role of heart mitochondrial subcellular location*. Biochim Biophys Acta, 2011. 1807: p. 1106-13.
25. Boengler, K., et al., *Presence of connexin 43 in subsarcolemmal, but not in interfibrillar cardiomyocyte mitochondria*. Basic Res Cardiol, 2009. 104: p. 141-7.
26. Ferreira, R., et al., *Subsarcolemmal and intermyofibrillar mitochondria proteome differences disclose functional specializations in skeletal muscle*. Proteomics, 2010. 10: p. 3142-54.
27. Palmer, J. W., B. Tandler, & C. L. Hoppel, *Heterogeneous response of subsarcolemmal heart mitochondria to calcium*. Am J Physiol, 1986. 250: p. H741-8.
28. Judge, S., Y. M. Jang, A. Smith, T. Hagen, & C. Leeuwenburgh, *Age-associated increases in oxidative stress and antioxidant enzyme activities in cardiac interfibrillar mitochondria: implications for the mitochondrial theory of aging*. FASEB J, 2005. 19: p. 419-21.
29. Taylor, R. W. & D. M. Turnbull, *Mitochondrial DNA mutations in human disease*. Nat Rev Genet, 2005. 6: p. 389-402.
30. Holt, I. J., A. E. Harding, & J. A. Morgan-Hughes, *Deletions of muscle mitochondrial DNA in patients with mitochondrial myopathies*. Nature, 1988. 331: p. 717-9.
31. Wallace, D. C., et al., *Mitochondrial DNA mutation associated with Leber's hereditary optic neuropathy*. Science, 1988. 242: p. 1427-30.
32. Khrapko, K., et al., *Mitochondrial mutational spectra in human cells and tissues*. Proc Natl Acad Sci USA, 1997. 94: p. 13798-803.
33. DiMauro, S. & A. L. Andreu, *Mutations in mtDNA: are we scraping the bottom of the barrel?* Brain Pathol, 2000. 10: p. 431-41.
34. Moyes, C. D. & D. A. Hood, *Origins and consequences of mitochondrial variation in vertebrate muscle*. Annu Rev Physiol, 2003. 65: p. 177-201.
35. Goto, Y., I. Nonaka, & S. Horai, *A mutation in the tRNA(Leu)(UUR) gene associated with the MELAS subgroup of mitochondrial encephalomyopathies*. Nature, 1990. 348: p. 651-3.
36. Shoffner, J. M., et al., *Myoclonic epilepsy and ragged-red fiber disease (MERRF) is associated with a mitochondrial DNA tRNA(Lys) mutation*. Cell, 1990. 61: p. 931-7.
37. Chinnery, P. F., N. Howell, R. N. Lightowlers, & D. M. Turnbull, *Molecular pathology of MELAS and MERRF. The relationship between mutation load and clinical phenotypes*. Brain, 1997. 120 (Pt 10): p. 1713-21.
38. Yoneda, M., A. Chomyn, A. Martinuzzi, O. Hurko, & G. Attardi, *Marked replicative advantage of human mtDNA carrying a point mutation that causes the MELAS encephalomyopathy*. Proc Natl Acad Sci USA, 1992. 89: p. 11164-8.
39. Chomyn, A., et al., *MELAS mutation in mtDNA binding site for transcription termination factor causes defects in protein synthesis and in respiration but no change in 39. *levels of upstream and downstream mature transcripts.* Proc Natl Acad Sci USA, 1992. 89: p. 4221-5.
40. Hayashi, J., et al., *Introduction of disease-related mitochondrial DNA deletions into HeLa cells lacking mitochondrial DNA results in mitochondrial dysfunction.* Proc Natl Acad Sci USA, 1991. 88: p. 10614-8.
41. Sciacco, M., E. Bonilla, E. A. Schon, S. DiMauro, & C. T. Moraes, *Distribution of wild-type and common deletion forms of mtDNA in normal and respiration-deficient muscle fibers from patients with mitochondrial myopathy.* Hum Mol Genet, 1994. 3: p. 13-9.
42. Kirches, E., et al., *Heterogeneous tissue distribution of a mitochondrial DNA polymorphism in heteroplasmic subjects without mitochondrial disorders.* J Med Genet, 2001. 38: p. 312-7.
43. He, Y., et al., *Heteroplasmic mitochondrial DNA mutations in normal and tumour cells.* Nature, 2010. 464: p. 610-4.
44. Li, M., et al., *Detecting heteroplasmy from high-throughput sequencing of complete human mitochondrial DNA genomes.* Am J Hum Genet, 2010. 87: p. 237-49.
45. Jenuth, J. P., A. C. Peterson, & E. A. Shoubridge, *Tissue-specific selection for different mtDNA genotypes in heteroplasmic mice.* Nat Genet, 1997. 16: p. 93-5.
46. Bua, E., et al., *Mitochondrial DNA-deletion mutations accumulate intracellularly to detrimental levels in aged human skeletal muscle fibers.* Am J Hum Genet, 2006. 79: p. 469-80.
47. Elson, J. L., D. C. Samuels, D. M. Turnbull, & P F Chinnery, *Random intracellular drift explains the clonal expansion of mitochondrial DNA mutations with age.* Am J Hum Genet, 2001. 68: p. 802-6.
48. Kowald, A. & T. B. Kirkwood, *Evolution of the mitochondrial fusion fission cycle and its role in aging.* Proc Natl Acad Sci USA, 2011. 108: p. 10237-42.
49. Sondheimer, N., et al., *Neutral mitochondrial heteroplasmy and the influence of aging.* Hum Mol Genet, 2011. 20: p. 1653-9.
50. Stewart, J. B., C. Freyer, J. L. Elson, & N. G. Larsson, *Purifying selection of mtDNA and its implications for understanding evolution and mitochondrial disease.* Nat Rev Genet, 2008. 9: p. 657-62.
51. Stewart, J. B., et al., *Strong purifying selection in transmission of mammalian mitochondrial DNA.* PLoS Biol, 2008. 6: p. e10.
52. Madamanchi, N. R. & M. S. Runge, *Mitochondrial dysfunction in atherosclerosis.* Circ Res, 2007. 100: p. 460-73.
53. Brandon, M. C., et al., *MITOMAP: a human mitochondrial genome database—2004 update.* Nucleic Acids Res, 2005. 33: p. D611-3.
54. Trifunovic, A., et al., *Premature ageing in mice expressing defective mitochondrial DNA polymerase.* Nature, 2004. 429: p. 417-23.
55. Edgar, D., et al., *Random point mutations with major effects on protein-coding genes are the driving force behind premature aging in mtDNA mutator mice.* Cell Metab, 2009. 10: p. 131-8.
56. Vermulst, M., et al., *DNA deletions and clonal mutations drive premature aging in mitochondrial mutator mice.* Nat Genet, 2008. 40: p. 392-4.
57. Kraytsberg, Y., D. K. Simon, D. M. Turnbull, & K. Khrapko, *Do mtDNA deletions drive premature aging in mtDNA mutator mice?* Aging Cell, 2009. 8: p. 502-6.
58. Dai, D. F., et al., *Overexpression of catalase targeted to mitochondria attenuates murine cardiac aging.* Circulation, 2009. 119: p. 2789-97.
59. Payne, B. A., et al., *Mitochondrial aging is accelerated by anti-retroviral therapy through the clonal expansion of mtDNA mutations.* Nat Genet, 2011. 43: p. 806-10.
60. Guaraldi, G., et al., *Coronary aging in HIV-infected patients.* Clin Infect Dis, 2009. 49: p. 1756-62.
61. Kurelac, I., et al., *Searching for a needle in the haystack: Comparing six methods to evaluate heteroplasmy in difficult sequence context.* Biotechnol Adv, 2011.
62. Hancock, D. K., L. A. Tully, & B. C. Levin, *A Standard Reference Material to determine the sensitivity of techniques for detecting low frequency mutations, SNPs, and heteroplasmies in mitochondrial DNA.* Genomics, 2005. 86: p. 446-61.
63. Kraytsberg, Y., A. Nicholas, P. Caro, & K. Khrapko, *Single molecule PCR in mtDNA mutational analysis: Genuine mutations vs. damage bypass-derived artifacts.* Methods, 2008. 46: p. 269-73.
64. Pohjoismaki, J. L. & S. Goffart, *Of circles, forks and humanity: Topological organisation and replication of mammalian mitochondrial DNA.* Bioessays, 2011. 33: p. 290-9.
65. Bielas, J. H. & L. A. Loeb, *Quantification of random genomic mutations.* Nat Methods, 2005. 2: p. 285-90.
66. Vermulst, M., et al., *Mitochondrial point mutations do not limit the natural lifespan of mice.* Nat Genet, 2007. 39: p. 540-3.
67. Vermulst, M., J. H. Bielas, & L. A. Loeb, *Quantification of random mutations in the mitochondrial genome.* Methods, 2008. 46: p. 263-8.
68. Castle, J. C., et al., *DNA copy number, including telomeres and mitochondria, assayed using next-generation sequencing.* BMC Genomics, 2010. 11: p. 244.
69. Tang, S. & T. Huang, *Characterization of mitochondrial DNA heteroplasmy using a parallel sequencing system.* Biotechniques, 2010. 48: p. 287-96.
70. Forster, L., et al., *Evaluating length heteroplasmy in the human mitochondrial DNA control region.* Int J Legal Med, 2010. 124: p. 133-42.
71. Vasta, V., S. B. Ng, E. H. Turner, J. Shendure, & S. H. Hahn, *Next generation sequence analysis for mitochondrial disorders.* Genome Med, 2009. 1: p. 100.
72. Zaragoza, M. V., M. C. Brandon, M. Diegoli, E. Arbustini, & D. C. Wallace, *Mitochondrial cardiomyopathies: how to identify candidate pathogenic mutations by mitochondrial DNA sequencing, MITOMASTER and phylogeny.* Eur J Hum Genet, 2011. 19: p. 200-7.
73. Huang, T., *Next generation sequencing to characterize mitochondrial genomic DNA heteroplasmy.* Curr Protoc Hum Genet, 2011. Chapter 19: p. Unit 19 8.
74. Langmead, B., C. Trapnell, M. Pop, & S. L. Salzberg, *Ultrafast and memory-efficient alignment of short DNA sequences to the human genome.* Genome Biol, 2009. 10: p. R25.
75. Fleischer, S. & M. Kervina, *Long-term preservation of liver for subcellular fractionation.* Methods Enzymol, 1974. 31: p. 3-6.
76. Fleischer, S. & M. Kervina, *Subcellular fractionation of rat liver.* Methods Enzymol, 1974. 31: p. 6-41.
77. Widlak, P. & W. T. Garrard, *Discovery, regulation, and action of the major apoptotic nucleases DFF40/CAD and endonuclease G.* J Cell Biochem, 2005. 94: p. 1078-87.
78. Widlak, P. & W. T. Garrard, *Unique features of the apoptotic endonuclease DFF40/CAD relative to micrococcal nuclease as a structural probe for chromatin.* Biochem Cell Biol, 2006. 84: p. 405-10.

79. Widlak, P. & W. T. Garrard, *The apoptotic endonuclease DFF40/CAD is inhibited by RNA, heparin and other polyanions*. Apoptosis, 2006. 11: p. 1331-7.
80. Silvestri, G., C. T. Moraes, S. Shanske, S. J. Oh, & S. DiMauro, *A new mtDNA mutation in the tRNA(Lys) gene associated with myoclonic epilepsy and ragged-red fibers (MERRF)*. Am J Hum Genet, 1992. 51: p. 1213-7.
81. Moraes, C. T., et al., *Molecular analysis of the muscle pathology associated with mitochondrial DNA deletions*. Nat Genet, 1992. 1: p. 359-67.
82. 5747298, U. S. p., *Bst DNA polymerase with proofreading 3'-5' exonuclease activity*. 2011.
83. Paabo, S., D. M. Irwin, & A. C. Wilson, *DNA damage promotes jumping between templates during enzymatic amplification*. J Biol Chem, 1990. 265: p. 4718-21.
84. Borek, D., M. Cymborowski, M. Machius, W. Minor, & Z. Otwinowski, *Diffraction data analysis in the presence of radiation damage*. Acta Crystallogr D Biol Crystallogr, 2010. 66: p. 426-36.
85. Borek, D., S. L. Ginell, M. Cymborowski, W. Minor, & Z. Otwinowski, *The many faces of radiation-induced changes*. J Synchrotron Radiat, 2007. 14: p. 24-33.
86. Kulmala, S., A. Kulmala, T. AlaKleme, A. Hakanen, & K. Haapakka, *Intrinsic and 1-aminonaphthalene-4-sulfonate-specific extrinsic lyoluminescences of X-ray irradiated sodium chloride*. Analytica Chimica Acta, 1997. 340: p. 245-256.
87. Saran, M., W. Bors, & P. Lester, [2] *Pulse radiolysis for investigation of nitric oxide-related reactions*, in Methods in Enzymology. 1994, Academic Press. p. 20-34.
88. Hamilton, M. L., et al., *A reliable assessment of 8-oxo-2-deoxyguanosine levels in nuclear and mitochondrial DNA using the sodium iodide method to isolate DNA*. Nucleic Acids Res, 2001. 29: p. 2117-26.
89. Nakae, D., Y. Mizumoto, E. Kobayashi, O. Noguchi, & Y. Konishi, *Improved genomic/nuclear DNA extraction for 8-hydroxydeoxyguanosine analysis of small amounts of rat liver tissue*. Cancer Lett, 1995. 97: p. 233-9.
90. Kinde, I., J. Wu, N. Papadopoulos, K. W. Kinzler, & B. Vogelstein, *Detection and quantification of rare mutations with massively parallel sequencing*. Proc Natl Acad Sci USA, 2011. 108: p. 9530-5.
91. Simone, D., F. M. Calabrese, M. Lang, G. Gasparre, & M. Attimonelli, *The reference human nuclear mitochondrial sequences compilation validated and implemented on the UCSC genome browser*. BMC Genomics, 2011. 12: p. 517.
92. McKenna, A., et al., *The Genome Analysis Toolkit: a MapReduce framework for analyzing next-generation DNA sequencing data*. Genome Res, 2010. 20: p. 1297-303.
93. Quinlan, C. L., et al., *Conditioning the heart induces formation of signalosomes that interact with mitochondria to open mitoKATP channels*. Am J Physiol Heart Circ Physiol, 2008. 295: p. H953-H961.
94. Ritov, V. B., E. V. Menshikova, & D. E. Kelley, *High-performance liquid chromatography-based methods of enzymatic analysis: electron transport chain activity in mitochondria from human skeletal muscle*. Anal Biochem, 2004. 333: p. 27-38.
95. Wonnapinij, P., P. F. Chinnery, & D. C. Samuels, *The distribution of mitochondrial DNA heteroplasmy due to random genetic drift*. Am J Hum Genet, 2008. 83: p. 582-93.

Example 4. UT Grant: Unbiased Mapping of Somatic Mutations

Somatic mutations resulting from DNA damage or replication errors contribute to the central mechanisms of ageing and cancer development (Loeb 2011). However, our current understanding of the impact of somatic mutations on those processes is derived from indirect or fragmentary measurements, which has resulted in standing controversies and problems with mechanistic interpretations of the acquired data. Historically, methods to determine somatic mutations could not be applied on a genome-wide scale due to the cost and the error-level of sequencing. Studies of somatic mutations were limited to either special types of mutations (e.g. microsatellites, restriction sites) or mutations analyzed with artificial selection. It is not clear how biased the selection was or how the limited scope of those studies affected the conclusions. High-throughput sequencing methods developed in recent years have addressed the cost of obtaining data, but not the level of errors.

We apply a novel experimental method that, combined with the associated data analysis, provides unbiased and robust estimates of the acquired mutation levels in any part of an organism. In our approach, we trace the mutations in each dsDNA fragment independently, with an error level of unprecedented reliability; less than 1 per billion sequenced base pairs. A breakthrough aspect of the method is that it identifies somatic mutations against the inherent background created by instrumental errors, chemical damage to DNA and polymorphic variations in the genome. Another advantage of the method is that it requires only a minimal amount of sample per data point.

Our invention makes possible systematic studies of somatic mutations within different organs at different points in time and with different genetic, environmental and iatrogenic backgrounds. Despite the enormous amount of research on DNA damage, particularly oxidative damage, the lack of methods has prevented any organism-wide studies regarding the number of mutations accumulating during the organism's lifetime. Data obtained by different methods from a few tissues or cell types have been highly inconsistent, without a clear sense of whether the inconsistency is due to differences in biology or the artifacts of the techniques used.

The method is unique in terms of providing an unbiased scan for mutations and identifying even low levels of mutations. A strength of the method comes from an experimental setup that allows for statistical independence criteria validating the results. As a consequence, solid knowledge connecting DNA damage to the accumulation of mutations is achievable. This greatly influences the understanding of ageing, cancer processes, and possibly of other diseases where somatic mutations have been implicated. In cancer, the method is ideally suited to address mutator phenotypes, how frequently they are present in different cancers and if they contribute to the development of metastasis—the mutator phenotype connection has already been established for colon and breast cancers (Loth 2011).

Another area of big impact is the issue of environmental insults driving the accumulation of somatic mutations, and, consequently, the diseases. Here, the robustness, comprehensiveness and internal validation of the method are of special value, particularly because it can be used as a reference source for societal regulations referring both to the environment and to the side effects of medical procedures.

Somatic mutations have been studied for a long time by selecting them with a phenotypic marker, e.g. the HTRP gene. The selection introduces an unknown level of bias and requires cultivating a cell line, which severely restricts the range and type of studies. A recent approach has applied genome-wide mutation mapping to a clonally amplified group of cells, identifying the somatic mutations present in the cell that started the clonal line. Genomic DNA sequences obtained from a clonal colony with a particular phenotype are compared to the genomic sequences of cells in another part of the organism. However, in this method, the sequence variability in the studied cell population is lost in sequencing noise. Therefore, it is a method well-suited for identifying the mutations driving the phenotype, but not suited to be a general approach for studying the spectrum of somatic mutations.

Unbiased, genome-wide mapping of the full spectrum of somatic mutations unrestricted by sample type has already attracted interest. However, the proposed solutions at their initial steps employed DNA synchronous (PCR) (Da Sylva, Gordon et al. 2009; Kinde, Wu et 2011) or asynchronous (WGA) amplification (Gundry and Vijg 2011). This led to the unavoidable errors introduced by polymerases, creating a false positive signal at the level of polymerase fidelity. The most thorough of the three methods (Kinde, Wu et. al. 2011) determined the signal level to be in the range of 3 to 9 per 1 million bases. The article stated that at that signal level it could not identify which portions of the signal came from somatic mutations and which came from background/false positives. A breakthrough aspect of our proposal is not only a much lower level of errors, but also a comprehensive validation, which identifies the source of potential errors by their data signatures. This creates an additional research opportunity, as one particular source of errors is DNA damage—that is, chemically altered bases. Our method can both identify mutations and map chemical damage.

A central, novel aspect of the method is that, by generating clonal amplification after preparing a sequencing library, we can separate sequence information for both original strands of dsDNA. This requires a different protocol than that used by previous researchers. First, we ligate dsDNA with so-called Y sequencing adapters. The difference between two strands in the Y junction is used later to identify which original strand of the duplex formed a particular colony produced by bridge amplification and resulted in a sequence read. The reads from the two strands are fully independent in their errors, with the exception of one instance that we identified and have a solution for. Consequently, this independence is the basis for validation, and because the error level for consensus reads from a single strand has been demonstrated to be below $10^{-5}$, combining data from the two strands should give an error level of $10^{-10}$.

TABLE 1

Distributions of patterns of changes in sequence in clonal clusters. (a) the change present in the same position in all sequencing reads contributing to cluster; (b) the same as (a) but the change is present also in complementary cluster; (c) the change is present in some of the reads contributing to a clonal cluster; (d) presence of the change in other reads mapping to the same genomic position. ++ indicates pattern that is always present, -- is always absent, + is predominantly present, and - is predominantly absent.

|  | a | b | c | d |
|---|---|---|---|---|
| Somatic mutations | ++ | ++ | -- | -- |
| SNPs | ++ | ++ | -- | + |
| Chemical Damage | + | -- | - | -- |
| PCR errors | - | -- | - | -- |
| Other (random) errors | -- | -- | -- | -- |

In a first step the solution to the issue of chemical damage driving sequencing errors that we recently identified was tested with *E. coli* DNA. We use free radical scavengers (sodium iodide and galic acid), a faster preparation of DNA sequencing libraries, and DNA repair enzymes (e.g. Fpg (formamidopyrimidine [fapy]-DNA glycosylase) and Uracil-DNA glycosylase). We also switch from sonication to double strand-specific DNAse digestion that generates blunt ends (Widlak and Garrard 2006) to eliminate the need for end repair that is used in the standard approach. We identified the repair polymerase as the source of error propagation between strands, and when it is eliminated each strand provides independent information. We can achieve a single-strand consensus error rate below $10^{-6}$. However, even a tenfold higher error rate is sufficient to proceed to the second step.

In the second step, we test two tissue samples from the same individual: one with an expected low number of somatic mutations, and the other with an expected high number of somatic mutations. We also test two samples from different tissues from the same individual to characterize the genomic polymorphism that is an additional challenge in human somatic mutation studies. For this reason, we chose human tissues rather than those from a model organism, as the background knowledge about DNA polymorphism in the human population is superior to that in other organisms. Nevertheless, each individual carries about 50,000 polymorphisms not described in the SNP databases (The 1000 Genomes Project Consortium 2010). To identify and eliminate those polymorphisms as a source of false positives, we perform sufficiently deep regular sequencing, without clonal amplification, using lanes of Illumina 2000 Hiseq paired reads with 100 bp each. To detect the somatic mutation spectrum, we use 2 sequencing lanes per tissue. We also use 2 sequencing lanes to establish the best conditions preventing DNA damage.

Computational analysis. First, the clonally-amplified fragments are clustered together and a consensus sequence for a cluster is determined separately for the two original strands. Next, the select, highly-reliable consensus sequences are mapped on a reference genome. Then, they are compared to each other and to the reference data. Depending on the pattern of differences between the clusters and the reference data, the difference are classified as a somatic mutation, polymorphism, DNA damage or another problem.

Da Sylva, T. R., C. S. Gordon, et al. (2009). "A genetic approach to quantifying human in vivo mutation frequency uncovers transcription level effects." *Mutat Res* 670(1-2): 68-73.

Gundry, M. and J. Vijg (2011). "Direct mutation analysis by high-throughput sequencing: From germline to low-abundant, somatic variants." *Mutat Res.*

Kinde, I., J. Wu, et al. (2011). "Detection and quantification of rare mutations with massively parallel sequencing." *Proc Natl Acad Sci USA* 108(23): 9530-9535.

Loeb, L. A. (2011). "Human cancers express mutator phenotypes: origin, consequences and targeting." *Nat Rev Cancer* 11(6): 450-457.

The 1000 Genomes Project Consortium, A. (2010). "A map of human genome variation from population-scale sequencing." *Nature* 467(7319): 1061-1073.

Widlak, P. and W. T. Garrard (2006). "Unique features of the apoptotic endonuclease DFF40/CAD relative to micrococcal nuclease as a structural probe for chromatin." *Biochem Cell Biol* 84(4): 405-410.

Optimization

Our method can reach the certainty level of 1 error per $10^{10}$ sequenced base pairs with certain optimizations: (1) The level of errors induced by chemical damage in each DNA strand of the duplex DNA is sufficiently low, i.e. $10^{-5}$ to $10^{-6}$ per base; (2) Complementary errors (errors that generate an alternative, valid duplex DNA sequence) in two DNA strands of a dsDNA fragment are statistically independent, i.e. they occur in the complementary position only due to rare random coincidences; (3) Frequency of observing sequences from both strands of a particular DNA fragment is high enough. Moreover, we should not confuse them with coincidental observations of complementary sequences originating from different duplexes. Additionally, the relevance of results is higher if we have a uniform coverage of all regions of the genome, so we should minimize coverage biases.

Below, we discuss types of and corrective procedures for systematic errors that can impact one or more one of these required condition.

(1) Low Level of Errors Per Single Strand of in a DNA Duplex

Initially, we identified oxidative damage as the main source of chemical damage, and attributed it to the relatively long time that it initially took us to perform the sequencing library preparation. However, modification of the experimental protocol to minimize the correlated errors by using DFF40 nuclease, in combination with a shortened time of library preparation revealed that there are additional chemical modifications that can be eliminated.

We discovered that the presence of common chemical modifications: abasic site, methylation of bases, deamination and oxidation of bases resulted in altered sequencing readouts. Some of these modifications also negatively affected the amplification during clonal and normal PCR amplifications, and during the formation of a sequencing polony.

For instance, the presence of abasic sites caused deletions and/or random substitutions in data, depending on the type of polymerase that encountered such lesions. However, in 99 to 99.5% of times, the consequence of such damage was an incomplete DNA copy, resulting in lack of the readout from this strand. For this reason, abasic sites are more important contributors to lowering the efficiency of Twin-seq (Condition 3) than to the error level. We devised a procedure to either eliminate some of chemical modifications or to correct the damaged events so they do not affect the sequencing readout.

First, after the fragmentation of DNA, Fpg (known as formamidopyrimidine [fapy]-DNA glycosylase or 8-oxoguanine DNA glycosylase can be used to remove abasic sites and sites of oxidative damage, which are generally not processed by nucleases such as Mung Bean Nuclease (MBN). Then, MBN or similar enzyme can be used to remove ssDNA extensions, recognize structures that miss one or more nucleotides on one strand of the duplex and then create dsDNA breaks at these points (Chaudhry and Weinfeld, N A R, 1995). The enzyme used at this point should not have polymerase activity, because that would generate complementary errors. Finally, one can use T7 ligase that seals nicks but does not ligate fragments that have blunt ends. Prior use of MBN should remove fragments with sticky ends, with which T7 ligase could produce undesired hybrids. DNA dilution may be additionally used to prevent the formation of hybrids. The need for ligase use is due to MNB not being very efficient in cleaving DNA with a simple nick. Other DNA repairing enzymes, without polymerase activity, can be also used instead of or in addition to the ones just described. These procedures will produce blunt-ended dsDNA without nicks and abasic sites. Then a standard library-preparation procedure can be applied, for instance dA-tailing, followed by the ligation of sequencing adapters.

We discovered that disposable gels (Invitrogen) used in our process severely affect the outcome, due to built-in copper electrodes (Brody J R, Kern S E., 2004, T. Ray, A. Mills, P. Dyson, 1995, and Invitrogen patent for EX gels). The combination of high currents, higher than ambient temperatures generated during electrophoresis, led to an increased level of copper ions and damaging radicals, which together introduce frequent DNA damage.

Additional damaging events are catalyzed by thermal radicals generated during sonication and by various hydroxyl-based species generated during purification, storage and PCR amplification. All those reactions are catalyzed by the presence of specific ions, such as $Fe^{2+}$ or $Cu^+$, leading to DNA breaks and base oxidation through Fenton and Fenton-like reactions.

To minimize the above problems, we devised a novel strategy. Using 0.1 mM EDTA as a chelator is, in our opinion, insufficient. Instead we use as additives: sodium iodide, to quench radicals generated in the procedure, sodium nitrate to quench hydrated electrons, deferoxamine to specifically chelate $Fe^{2+}$ ions, and neocuproine to specifically chelate $Cu^+$ cations without affecting the levels of other ions, such as for instance $Mg^{2+}$, $Ca^{2+}$ and $Zn^{2+}$, which are used in the enzymatic reactions involved in sequencing library preparation. The final concentration of these compounds typically ranges from 0.1 mM to 1 mM total for all components of the mix. They can be used either as a single additive or in combinations, also during PCR amplification. In Twin-seq, PCR amplifications are performed in standard conditions, i.e. high temperatures are used for 18-26 cycles of PCR.

(2) Correlated Complementary Errors that Result in Changes Mimicking Mutations

The standard protocols of generating samples for sequencing involve so-called blunt-ending, in which two enzymatic activities are used to remove single-stranded ends of double-stranded fragments. The first enzymatic activity fills in 5' overhangs, using 5'-3' polymerase activity; the second one removes 3' overhangs with 3'-5' exonuclease activity. The polymerase activity uses a single-strand overhang as a template. If this overhang contains a damaged base, e.g. oxidized guanidine, the synthesized second strand will contain a base complementary to damaged one. The presence of these two bases will generate complementary reads that look as if they contained a mutation. Because our method is focused on mapping rare mutations, including the somatic ones, even a rare occurrence of such errors is highly detrimental. In fact, we observed that this could be the biggest source of false mutation calls.

We proposed to use DFF40 nuclease, which is specific to dsDNA, for digesting DNA for sequencing. DFF40 creates double-stranded breaks ready for dA-tailing. This eliminates the need for blunt-ending reaction, which was the biggest source of correlated complementary sequencing errors in our initial experiments. This approach worked, and such errors were effectively eliminated.

Our experiments with fragmentation by DFF40 revealed, however, some additional sources of problems, for which we devised additional corrections. Our data indicate that DFF40 has a residual nickase activity and is likely to introduce short gaps in one of strands in the duplex. In our experiment these gaps were filled with adenine introduced in the next step—dA-tailing, and then sealed with T4 ligase used during ligation. Additionally, we observed insertions, which we interpret as strand elongation from nicks that were sealed by ligase. The enzymatic mix for removing damaged bases, described before, could be also used to handle these nicks. If DNA quality is good, T7 ligase can be used directly after DFF40 digestion, and then followed by MBN nuclease.

Digestion with DFF40 nuclease is not completely random—DFF40 prefers some sequence contexts. Therefore, our initial adapters with limited randomization turned out to be insufficient for some genomic sequences. For particular genomic fragments, we observed sequencing readouts that had multiple different barcodes. Statistics implies that we were dealing with significant presence of coincidental, identical reads originating from different DNA fragments.

Therefore, we designed new barcodes, with the following properties: (1) compatible with multiplexed reactions; (2) resistant to one or two sequencing/synthesis errors; (3) providing better randomization; (4) having built-in composition balance when only a sub-set of barcodes is used. This facilitates image focusing and registration in fluorescence-based readouts and improves cluster calling and base calling. The design allows for full compositional balance with just pairs of barcodes used.

The example of our design below is based on Hamming (7,4) error correcting code (Hamming 1950); it allows for up to 16 barcodes that should be used in pairs. If more barcodes are needed, the design can be easily extended to other binary error-correction codes.

Mutations may be also mimicked by random coincidence of two errors on the complementary strands. Therefore, we model the probability of coincidences with respect to each identified dsDNA Twin-seq cluster, which allows us to estimate false positive and false negative rates. It is well known, and we observed it in our data, that some sequences are much more susceptible to specific DNA modifications. Therefore, we count the observed frequency of single-stranded clonal errors in data as a function of their sequence environment. This creates a probabilistic model of false-positive background resulting from coincidental errors, i.e. the complementary change in DNA happening on both strands.

(3) Presence of Both Strands of the Initial Duplex in the Sequenced Pool.

Even with high clonal amplification, we don't always observe pairs resulting from both strands in the DNA fragment. At this point we observe 25 to 50% of Twin-seq pairs, depending on the sequencing reaction. This incompleteness arises from one of the strands not being amplifiable during PCR, due to DNA damage, errors in adapter

| | Barcode structure for template strand (5' to 3') | | |
|---|---|---|---|
| Code Word | Randomized part | Hamming (7,4) barcode | Illumina adapter sequence |
| 0000111 | /5Phos/NNNN | RRRRYYY | TrueSeq forward |
| 1111000 | /5Phos/NNN | YYYYRRR | . . . |
| 1010110 | /5Phos/NNNN | YRYRYYR | . . . |
| 0101001 | /5Phos/NNN | RYRYRRY | . . . |
| 1110101 | /5Phos/NNNN | YYYRYRY | . . . |
| 0001010 | /5Phos/NNN | RRRYRYR | . . . |
| 0100100 | /5Phos/NNNN | RYRRYRR | . . . |
| 1011011 | /5Phos/NNN | YRYYRYY | . . . |
| 0110011 | /5Phos/NNNN | RYYRRYY | . . . |
| 1001100 | /5Phos/NNN | YRRYYRR | . . . |
| 1100010 | /5Phos/NNNN | YYRRRYR | . . . |
| 0011101 | /5Phos/NNN | RRYYYRY | . . . |
| 1000001 | /5Phos/NNNN | YRRRRRY | . . . |
| 0111110 | /5Phos/NNN | RYYYYYR | . . . |
| 0010000 | /5Phos/NNNN | RRYRRRR | . . . |
| 1101111 | /5Phos/NNN | YYRYYYY | . . . |

TrueSeq forward: AGATCGGAAGAGCACACGTCTGAACTCCAGTCAC (SEQ ID NO: 02)

Unlike other barcode designs, our barcodes themselves have a 128-fold randomization. Additionally, to increase the randomization level, we add positions with four-fold randomization. Ligation requires the presence of a particular base in the read positions at the end of the adapter. If all adapters were of the same length, it would generate only one base in such positions. Our design avoids it by introducing adapters of unequal lengths, with barcodes identifying the length. Extending the length of the fully randomized part of the adapters makes them suitable for studies where low sequence diversity is expected.

synthesis or lack of ligation on one strand of the duplex. DNA damage is the most likely explanation.

We estimated the damage to the double-stranded part of adapter-ligated fragments by counting Twin-seq pairs as a function of the sequenced insert length. However, the damage derived from length-dependence accounts only for 10-20% part of the effect, so there have to be other sources. In our procedure, like others are doing, we size-select ligated fragments when they have single-stranded parts of Y-adapter present on both ends. Single-stranded DNA is much more susceptible to damage than double-stranded DNA due to a different solvent accessibility of bases, which makes procedures that use Y-adapters (prior to and after ligation) likely to be the main contributors to reducing the efficiency of Twin-seq. In particular, the damage induced by electrophoresis, which we described earlier, is highly important, and the above discussed remedies should also improve the efficiency of Twin-seq. Additionally, following the ligation by one cycle of amplification with strand-displacing polymerase will generate fully duplexed DNA, less subject to damage during size selection. Moreover, this single-cycle amplification can be performed with high-fidelity polymerizes at room temperature, reducing the frequency observing the same PCR error multiple times.

The value of almost every sequencing method increases when genomic coverage becomes more uniform. We provide two independent methods to improve the uniformity of coverage.

The first approach deals with non-uniformity resulting from all fragmentation methods having their particular forms of sequence preferences that result in coverage bias when fragments are subjected to size selection. For whatever type of DNA fragmentation, the bias is reduced by performing fragmentation as a series of incremental steps and pooling DNA fragments at each step. For instance, in the case of DFF40 digestion, the aliquots of digested DNA solution are pipetted out from the reaction to the stopping buffer at several time points and pooled. This approach generates a combination of underdigested, optimally digested, and overdigested fragments. These sub-pools have opposite sequence biases with respect to the coverage, so mixing them together improves uniformity.

Another source of non-uniformity of coverage is due to specific secondary structures preventing the amplification, either by PCR or on sequencing flow cell. For instance, G-quadruplexes are known to cause such problems. The purine analogs, such as 7-deazaguanidine, when incorporated into DNA, prevent the formation of G-quadruplexes and other strongly coupled structures, and are compatible with PCR amplification while not inducing replication errors. 7-deazadGTP used as an additive or replacement for dGTP in PCR amplifications should greatly improve the amplification of sequences where such structures form a barrier.

(4) Labeled Adapters

The oligos that were designed using Hamming (7,4) error codes can be annealed with the standard Illumina adapter before using Klenow (exo-) polymerase to create duplexes whose randomized part will be read out and will define the barcode for a particular DNA fragment being amplified. At the same time, these barcodes contain indices corresponding to a particular experiment in which they are used.

We prefer to not purify the randomized oligos by the standard DNA purification methods; as such procedure perturbs random distribution of bases. Additionally, standard purification is monitored with UV light, which undesirable side effect of damaging DNA bases. Since DNA synthesis errors are not random, we designed a procedure that creates fully functional Y adapters based on high affinity tags that preserve randomness of sequence tags. In normal sequencing, damage to Y adapters reduces only the amount of material amplified by PCR, which is typically of no consequence, due to large surplus of starting DNA. In Twin-seq such damage, which is predominantly single-stranded, creates PCR clones without their corresponding mates from other strands. That's why fully functional Y adapters are highly preferable.

Chemical DNA synthesis proceeds one base at a time, starting from 3' end, with errors due to incomplete deprotection accumulating at the 5' end of the oligo. We can introduce a compatible label, such as biotin at 5' end of the standard primer and then, after annealing, select duplexes with biotin binding to streptavidin-coated beads. Biotin can be incorporated at 5' ends by two approaches: additional synthesis step after DNA is synthesized, or, alternatively, by adding biotinylated dT at the end. In the second approach, biotin will be present only in full-length oligos, so selecting by biotin presence will eliminate unwanted side-products of chemical synthesis.

(v 1)
(SEQ ID NO: 03)
5'/biot/AATGATACGGCGACCACCGAGATCTACACTCTTTCCCTACAC GACGCTCTTCCGATCT-3';

(v 2)
(SEQ ID NO: 03)
5'/biotdT/AATGATACGGCGACCACCGAGATCTACACTCTTTCCCTAC ACGACGCTCTTCCGATCT-3'

The randomized oligo is annealed with the standard sequencing adapter to create a substrate for the polymerase that will create a full Y-adapter, e.g. for the adapter 00001111:

(SEQ ID NO: 03)
5'AATGATACGGCGACCACCGAGATCTACACTCTTTCCCTACACGACG CTCTTCCGATCT-3';

(SEQ ID NO: 04)
3'CACTGACCTCAAGTCTGCACACGAGAAGGCTAGAYYYRRRRNNNN/5Phos/

The product of ligating these adapters with DNA inserts is compatible with standard PCR primers and the rest of the sequencing process. The indexing/randomized part will be present at both ends of the insert. These random parts will contain the same chemical reaction identifier, but they will not be related with respect to randomization component. Each end will be sequenced at the start of its corresponding read. That means that total identified randomization will be the product of the number of possible base combinations at each end. Unlike in Illumina indexing, the identification of a chemical reaction tag will be done independently at each end, so even multiple readout or synthesis errors can be corrected. For example: Hamming (7,4) recognizes, but does not correct double errors; however, once recognized, even in the presence of a single error on the other end, the reaction will be properly recognized. For Twin-seq it is essential that the randomization tag is incorporated into normal reads, rather than into the indexing read tag in Illumina procedure. These Illumina tags are created in the single-stranded component of Y adapters, so a random instance added to the indexing read will not be present on a twin copy of DNA.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method of sequencing DNA using a sequencer, comprising:

(a) generating a sequencing library comprising the steps— attaching sequencing adapters to a plurality of DNA fragments to form a plurality of adapter-DNA molecules; and amplifying the adapter-DNA molecules to generate clonal strands of each adapter-DNA molecule;

(b) flowing a plurality of clonal strands over a sequencer flow cell such that multiple clonal strands of adapter-DNA molecules bind to the flow cell;

(c) bridge amplifying the bound strands of adapter-DNA molecules to form one or more polonies;

(d) sequencing the polonies to obtain a preliminary sequence read for each polony, wherein for each polony, sequencing includes—
  obtaining fluorescence intensity measurements for each nucleotide position of the polony; and
  performing a first round of base calling by converting the fluorescence intensity measurements into a probable base call for each nucleotide position of the polony to provide a preliminary sequence read, the preliminary sequence read having a preliminary error probability;
(e) grouping preliminary sequence reads generated from the clonal strands derived from a particular adapter-DNA molecule;
(f) calculating a fluorescence intensity measurement average for each nucleotide position from the grouped preliminary sequence reads; and
(g) performing a second round of base calling for each nucleotide position of the grouped preliminary sequence reads -using the fluorescence intensity measurement averages to provide a sequence read;
(h) wherein an error probability of the sequence read corresponding to the particular adapter-DNA molecule is lower than any one of the preliminary error probabilities of the individual preliminary sequence reads in the group.

2. The method of claim 1 wherein each of the preliminary sequence reads is a composite sequence generated from a plurality of sequencer readouts of each polony.

3. The method of claim 2 wherein a plurality of sequencer readouts of each polony is obtained by paired-end sequencing.

4. The method of claim 1 further comprising the step of identifying one or more correspondences between nucleotide positions along a plurality of sequence reads generated from the clonal strands derived from a particular adapter-DNA molecule by comparing fluorescence intensity measurements at said nucleotide positions.

5. The method of claim 1, further comprising mapping the preliminary sequencing reads to a reference genome, wherein the second round of base calling is on regions corresponding to the reference genome identified in the preliminary sequence reads as suspicious of having a phasing error.

6. The method of claim 5, wherein the regions of the reference genome identified in the preliminary sequence reads correspond to one or more polonies on the flow cell comprising inconsistent fluorescence intensities.

7. The method of claim 5, wherein the regions of the reference genome comprises an inverted repeat.

8. The method of claim 1, further comprising:
identifying a phasing error in a first group of preliminary sequence reads derived from a first adapter-DNA molecule having a first nucleic acid sequence; and
providing a phasing error estimate for a second group of preliminary sequence reads derived from a second adapter-DNA molecule, the second adapter DNA molecule having a second nucleic acid sequence that at least partially overlaps the first nucleic acid sequence.

9. The method of claim 1, further comprising analyzing a first group of preliminary sequence reads corresponding to a first adapter-DNA molecule to identify inconsistencies between individual preliminary sequence reads belonging to the first group.

10. The method of claim 9, wherein the analysis identified no inconsistencies between preliminary sequence reads of the first group and the preliminary sequence reads are determined to be an accurate sequence of the bound strands of the adapter-DNA molecule.

11. The method of claim 1, further comprising comparing one or more sequence reads to a reference sequence to identify a presence of a variant.

12. The method of claim 1, wherein, following the second round of base-calling, the method further comprises comparing a first sequence read derived from a first strand of a particular adapter-DNA molecule and a second sequence read derived from a second strand of the same adapter-DNA molecule to identify one or more inconsistencies.

13. The method of claim 12, wherein the inconsistencies are identified as amplification errors.

14. The method of claim 1, wherein, following the second round of base-calling, the method further comprises detecting an error when a sequence read derived from a particular adapter-DNA molecule has one or more inconsistent base calls, and wherein the error is identified as an amplification error.

15. The method of claim 1, wherein, following the second round of base-calling, the method further comprises detecting an error when a sequence reads derived from an original DNA fragment has one or more inconsistent base calls when compared to a second sequence reads derived from the same original DNA fragment, and wherein the error is identified as a chemical base alteration occurring prior to the bridge amplification step.

16. The method of claim 1, wherein one or more probable DNA base calls is identified as an incorrect base call, and wherein the method further comprises correcting the probable base call in the second round of base calling.

17. The method of claim 1, wherein for a plurality of sequence reads, the method further comprises identifying a sequence-specific desynchronization event.

18. The method of claim 17, wherein the sequence-specific-desynchronization event is identified by a steep cumulative Q-value decrease along the plurality of sequence reads.

19. The method of claim 18, wherein the plurality of sequence reads having the sequence-specific desynchronization event comprises one or more of high GC content, two GGC triplets, and a secondary structure formation.

* * * * *